US008152719B2

United States Patent
Tenger et al.

(10) Patent No.: US 8,152,719 B2
(45) Date of Patent: *Apr. 10, 2012

(54) LARYNGOSCOPE AND METHOD OF USE

(75) Inventors: James P. Tenger, Carlsbad, CA (US); Leslie A. Tenger, Carlsbad, CA (US); John R. Hick, Carlsbad, CA (US); Todd McKinney, Rancho Santa Fe, CA (US)

(73) Assignee: Intubrite, LLC, Vista, CA (US)

( * ) Notice: Subject to any disclaimer, the term of this patent is extended or adjusted under 35 U.S.C. 154(b) by 327 days.

This patent is subject to a terminal disclaimer.

(21) Appl. No.: 12/698,467

(22) Filed: Feb. 2, 2010

(65) Prior Publication Data

US 2010/0152541 A1 Jun. 17, 2010

Related U.S. Application Data

(63) Continuation-in-part of application No. 12/368,952, filed on Feb. 10, 2009, now abandoned, which is a continuation-in-part of application No. 12/173,961, filed on Jul. 16, 2008, now Pat. No. 8,012,087, which is a continuation-in-part of application No. 12/144,147, filed on Jun. 23, 2008, application No. 12/698,467, which is a continuation-in-part of application No. 29/346,594, filed on Nov. 3, 2009, now Pat. No. Des. 632,787.

(60) Provisional application No. 61/288,779, filed on Dec. 21, 2009.

(51) Int. Cl.
*A61B 1/267* (2006.01)

(52) U.S. Cl. ........................................ 600/199; 600/185

(58) Field of Classification Search .......... 600/185–199, 600/234, 245
See application file for complete search history.

(56) References Cited

U.S. PATENT DOCUMENTS

D185,398 S 6/1959 Todt
(Continued)

FOREIGN PATENT DOCUMENTS

KR 1020070044379 4/2007
(Continued)

OTHER PUBLICATIONS

Notification, International Search Report and Written Opinion dated Oct. 5, 2010 for PCT/US2010/023194.

(Continued)

*Primary Examiner* — Eduardo C Robert
*Assistant Examiner* — Nicholas Plionis
(74) *Attorney, Agent, or Firm* — Stephen C. Beuerle; Procopio Cory Hargreaves & Savitch LLP

(57) ABSTRACT

A laryngoscope blade for use in viewing the vocal cords of a patient in performance of an endotracheal intubation includes a laryngoscope blade portion connectable to a laryngoscope handle to lift the patient's tongue and mandible for viewing the vocal cords and aid in the insertion of an endotracheal tube, the blade portion includes a proximal portion and a distal portion; a white light source carried by the blade portion; a black light source carried by the blade portion to prompt the visible effects of fluorescence and phosphorescence with respect to the patient's vocal cords for viewing the vocal cords and passing of the endotracheal tube there between during endotracheal intubation, the black light source located closer to the distal portion and the white light located to the proximal portion, and the black light source emitting electromagnetic radiation having a wavelength in the range of 300 to 450 nm.

17 Claims, 50 Drawing Sheets

U.S. PATENT DOCUMENTS

| | | |
|---|---|---|
| D271,135 S | 10/1983 | Greenblatt |
| D297,363 S | 8/1988 | Salerno et al. |
| 4,782,819 A | 11/1988 | Adair |
| 4,827,910 A | 5/1989 | Mathews, III |
| D337,384 S | 7/1993 | Schucman |
| D449,499 S | 10/2001 | Voges |
| 6,459,919 B1 | 10/2002 | Lys et al. |
| 6,569,089 B1 | 5/2003 | Covington et al. |
| D491,267 S | 6/2004 | Ashraf |
| 6,809,499 B2 | 10/2004 | Solingen |
| 6,876,446 B2 | 4/2005 | Taylor et al. |
| D512,778 S | 12/2005 | Ashraf |
| 7,052,456 B2 | 5/2006 | Simon |
| D541,937 S | 5/2007 | Yee |
| D547,449 S | 7/2007 | Ashraf |
| D550,841 S | 9/2007 | Berci et al. |
| D554,255 S | 10/2007 | Iqbal |
| 7,308,296 B2 | 12/2007 | Lys et al. |
| D559,982 S | 1/2008 | Iqbal |
| D581,532 S | 11/2008 | Cranton et al. |
| 2003/0191459 A1 | 10/2003 | Ganz et al. |
| 2003/0195390 A1 | 10/2003 | Graumann |
| 2006/0069314 A1 | 3/2006 | Farr |
| 2007/0156022 A1 | 7/2007 | Patel |
| 2007/0276185 A1 | 11/2007 | Gono et al. |
| 2007/0276191 A1 | 11/2007 | Selover et al. |
| 2008/0015560 A1 | 1/2008 | Gowda et al. |
| 2008/0045800 A2 | 2/2008 | Farr |

FOREIGN PATENT DOCUMENTS

| | | |
|---|---|---|
| WO | WO93/01170 | 6/1993 |

OTHER PUBLICATIONS

International Search Report and Written Opinion for PCT/US08/074878 dated Mar. 19, 2009, 10 pages.

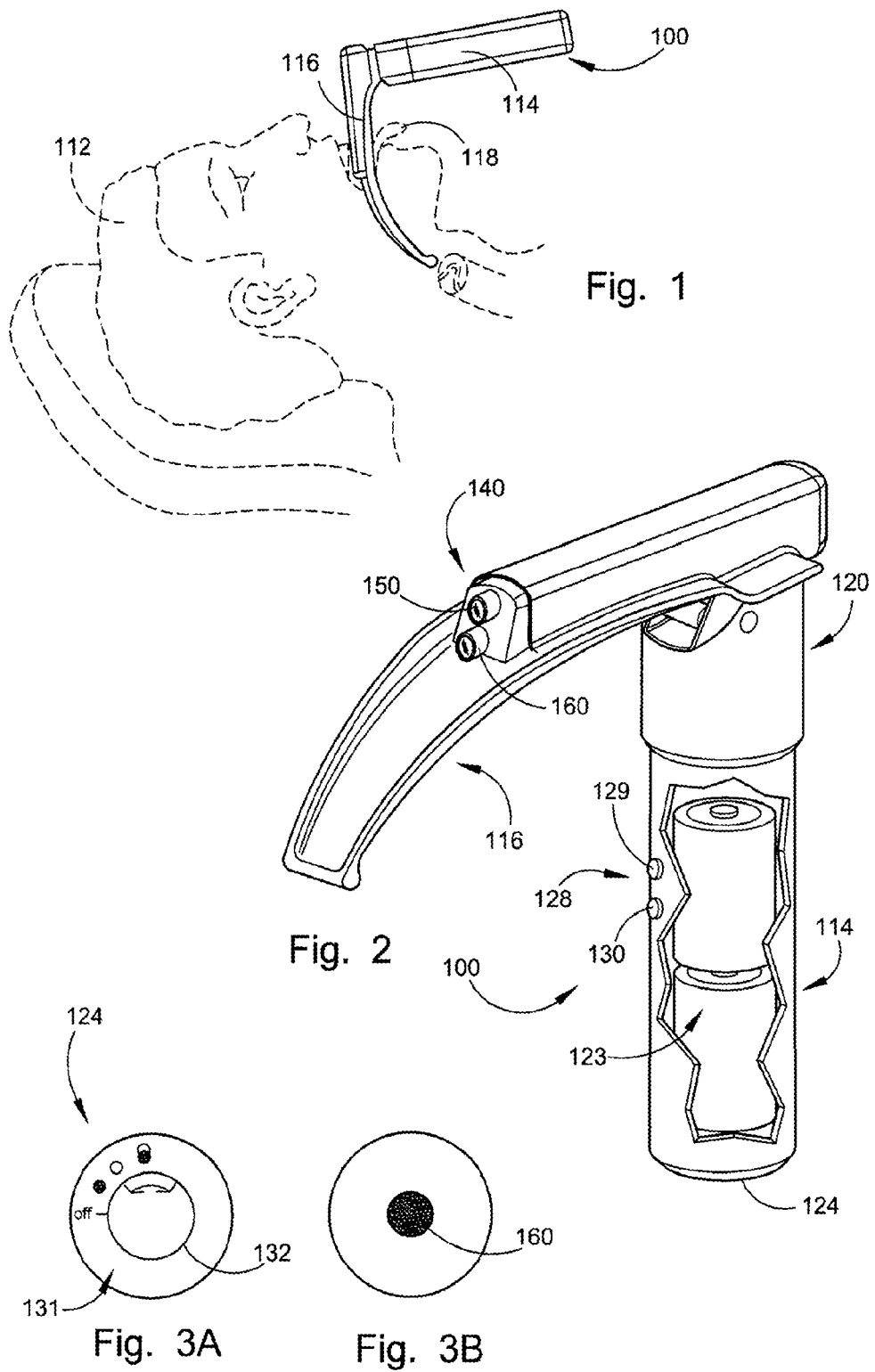

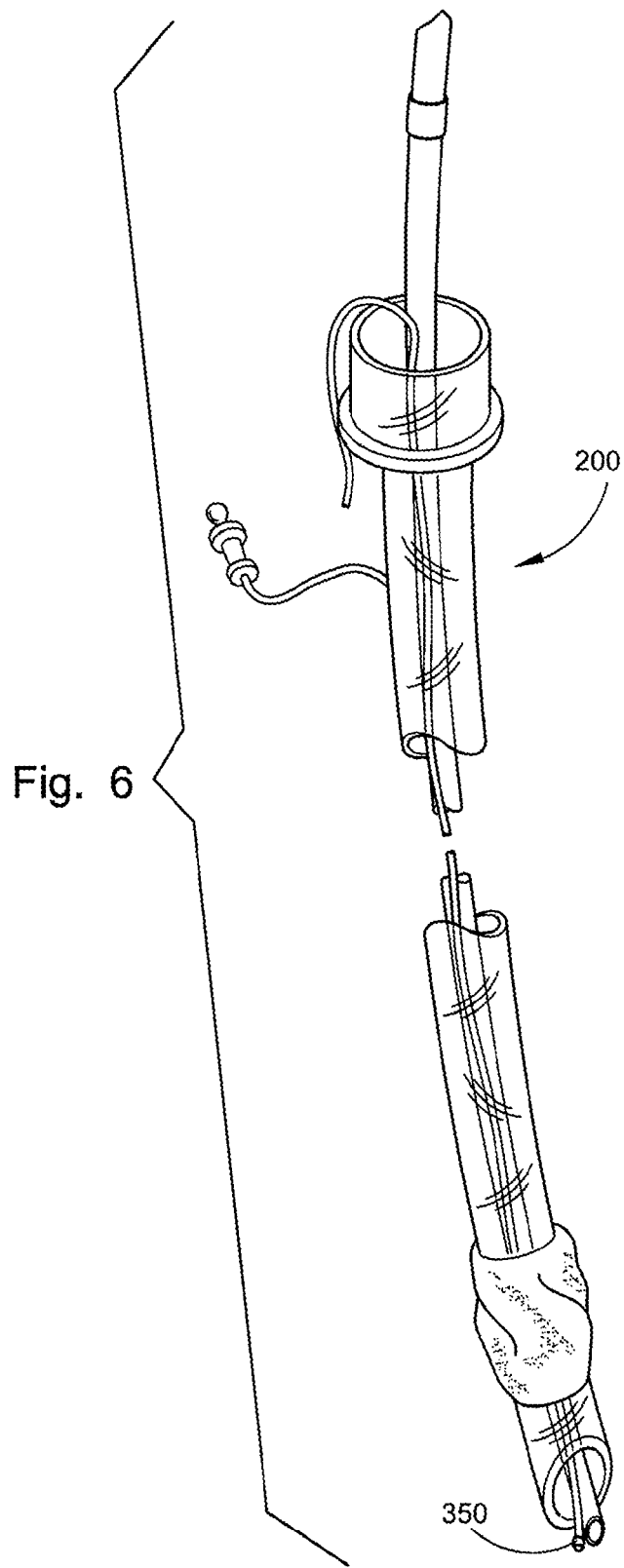

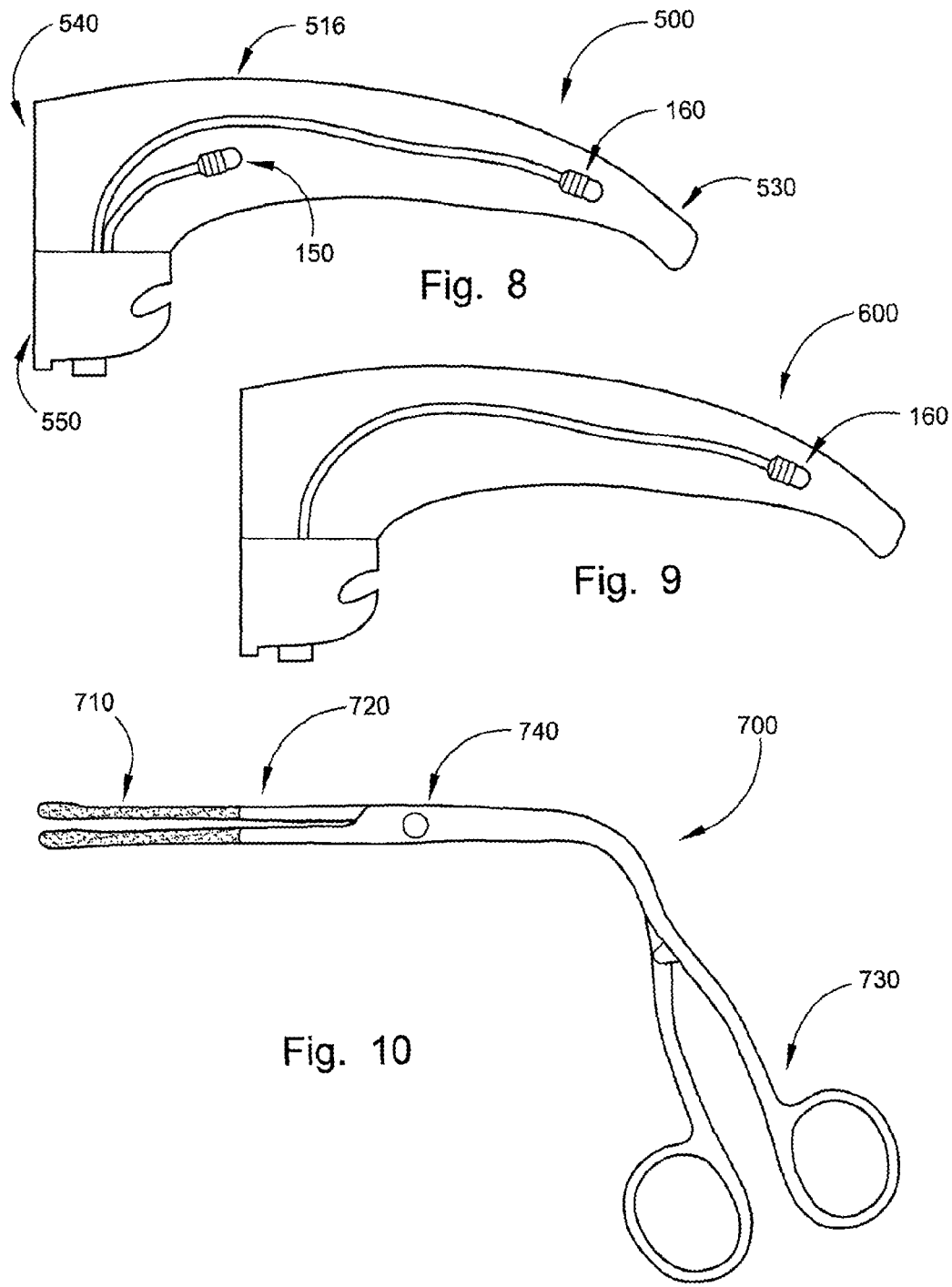

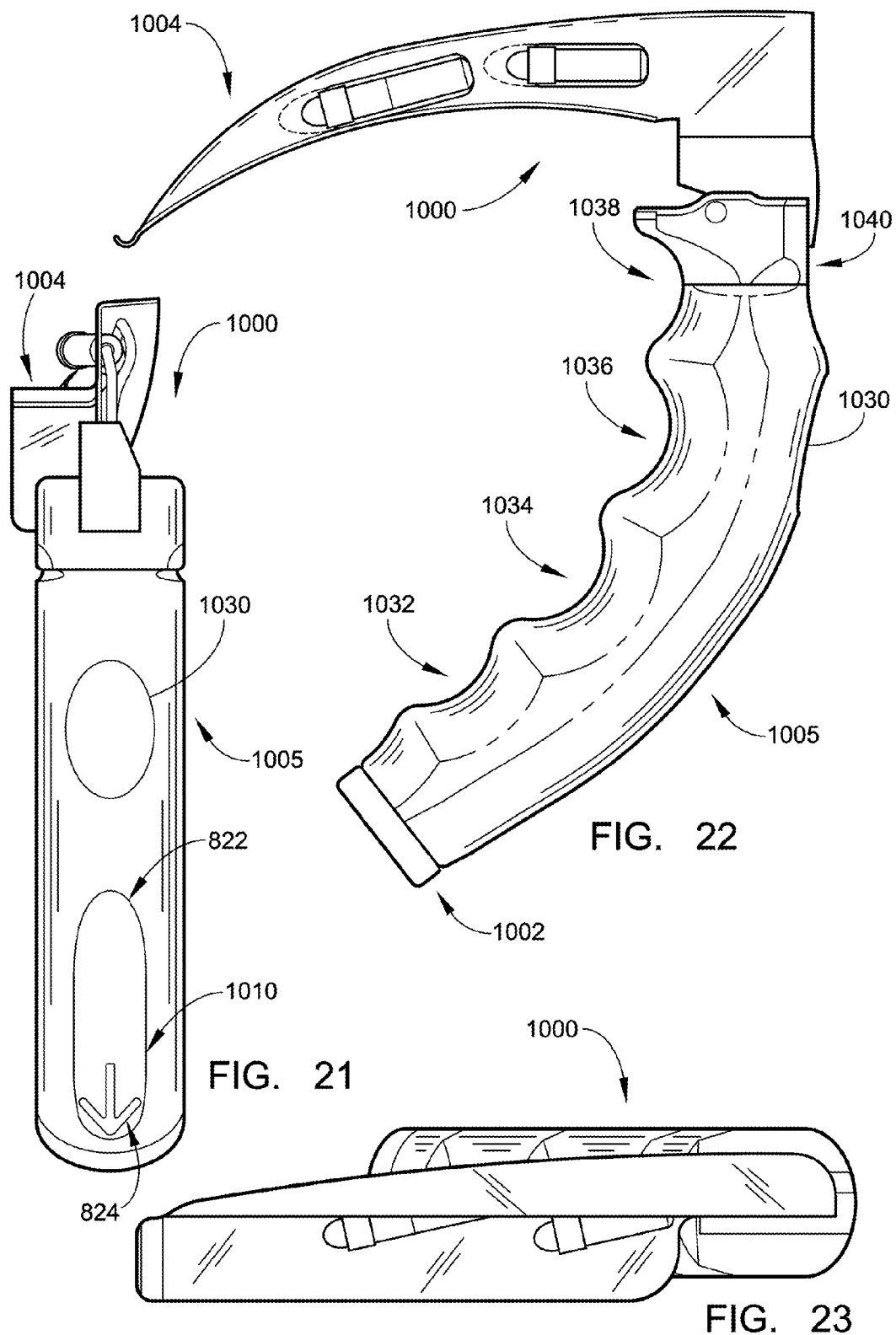

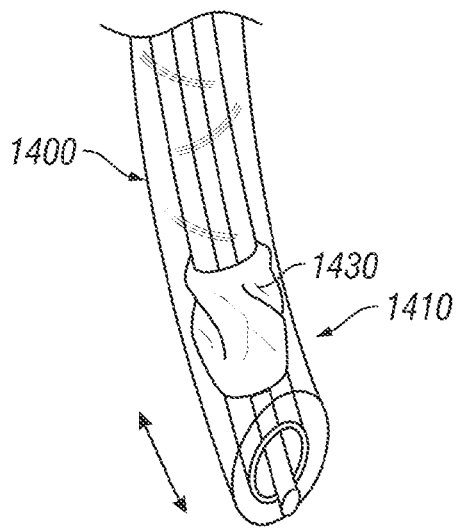
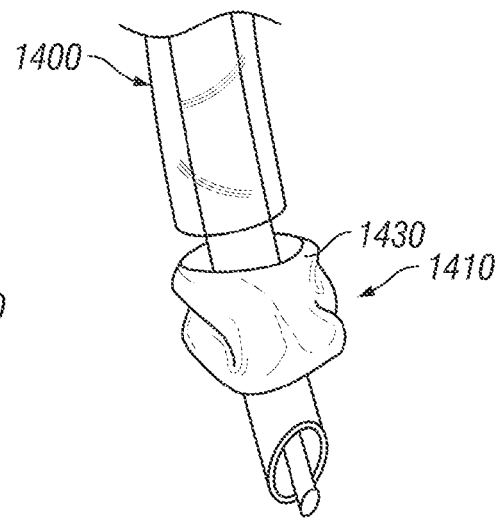
FIG. 37A  FIG. 37B
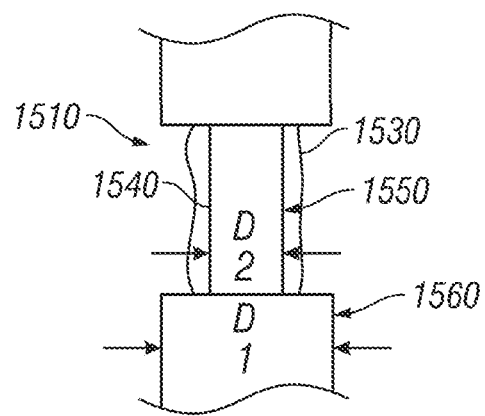
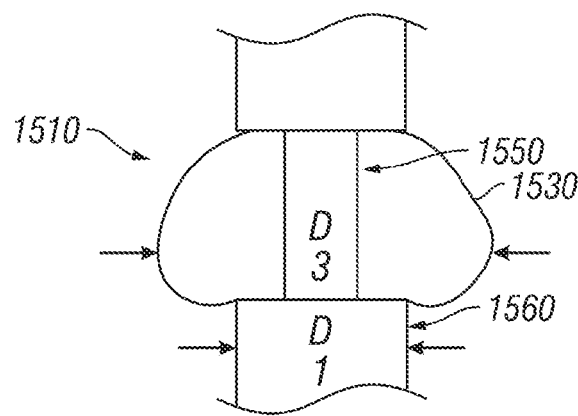
FIG. 38A  FIG. 38B

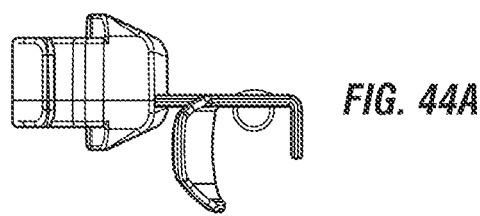
FIG. 44A
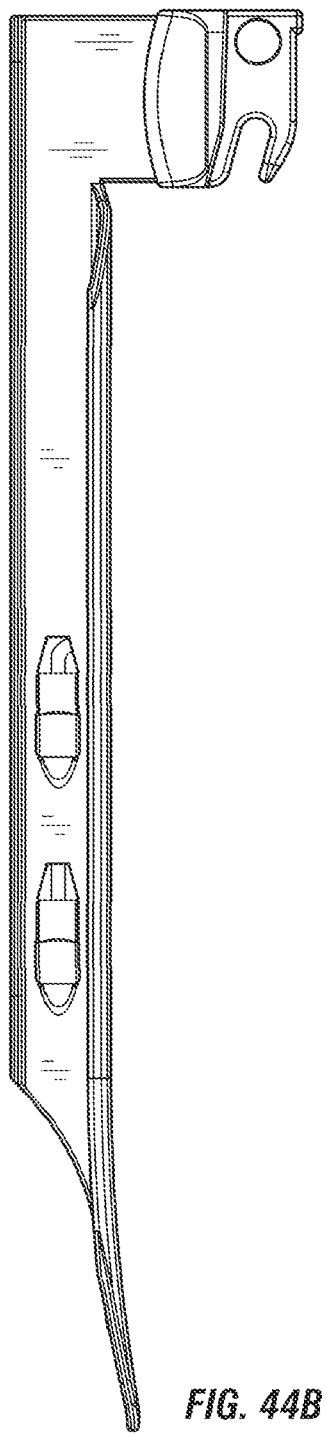
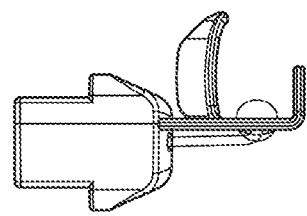
FIG. 44C
FIG. 44B

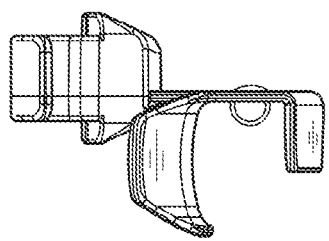
*FIG. 45A*
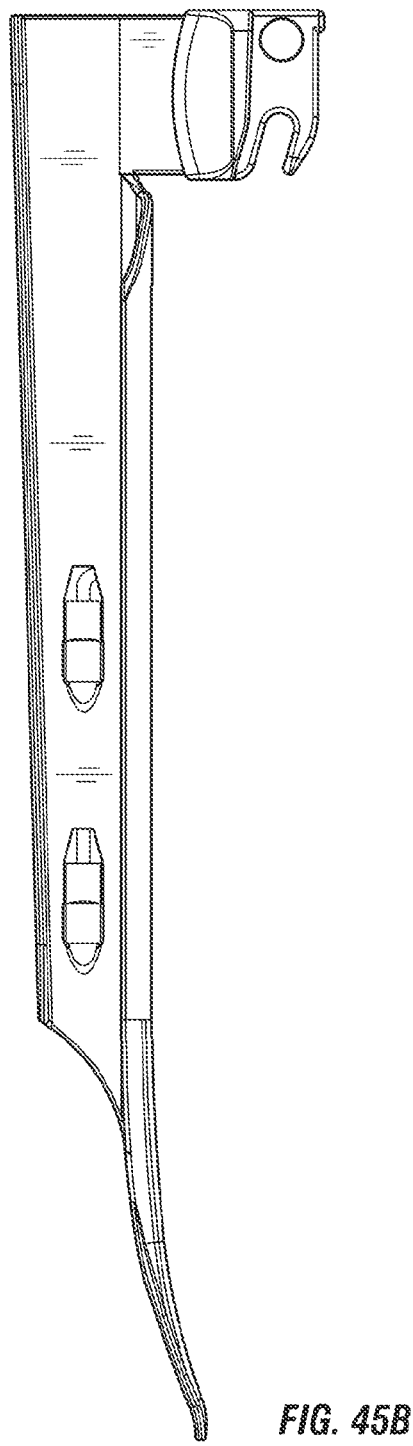
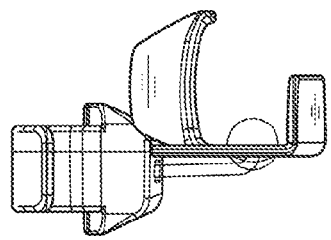
*FIG. 45C*
*FIG. 45B*

LARYNGOSCOPE AND METHOD OF USE

CROSS-REFERENCE TO RELATED APPLICATIONS

This application is a continuation-in-part of U.S. patent application Ser. No. 12/368,952 filed on Feb. 10, 2009, which is a continuation-in-part of U.S. patent application Ser. No. 12/173,961 filed on Jul. 16, 2008, which is a continuation-in-part of U.S. patent application Ser. No. 12/144,147, filed on Jun. 23, 2008. This application is also a continuation-in-part of U.S. patent application Ser. No. 29/346,594 filed on Nov. 3, 2009. This application also claims priority under 35 U.S.C. 119(e) to U.S. provisional patent application 61/288,779 filed Dec. 21, 2009. The contents of each and all of the above patent applications are incorporated herein by reference in their entirety.

FIELD OF THE INVENTION

The field of this invention relates to laryngoscopes and the laryngoscopy procedure.

BACKGROUND OF THE INVENTION

Health care providers perform direct laryngoscopy to either clear a patient's airway of debris, or place an endotracheal tube into a patient's trachea to assist or replace a patient's ability to oxygenate his/her system. The laryngoscope utilizes either a lighted straight or curved blade that allows visualization of the vocal cords, indicating the opening of the trachea. This lighted blade is used to keep the tongue from obstructing the medical provider's view of the vocal cords. The tip of the blade lifts the epiglottis, thereby providing a direct view into the patient's trachea, and reducing the risk of intubating the esophagus instead. Laryngoscopes in the past have used halogen or LED bulbs to provide a white light source on the laryngoscope blade to illuminate the vocal cords during laryngoscopy. Even with a light source on the laryngoscope blade, viewing of the vocal cords has still proven difficult during laryngoscopy. Accordingly, without the ability to view the vocal cords, many possible laryngoscopy procedures are not performed successfully, resulting in additional harm or death for the patient.

SUMMARY OF THE INVENTION

To solve these problems and others, an aspect of present invention involves a laryngoscope including an improved light source. The laryngoscope blade carries a black light source that emits a black light during laryngoscopy. The black light enhances visualization of the vocal cords so that visualization of the endotracheal tube passing through the vocal cords is enhanced. The black light emitted from the laryngoscope enhances colors that are white and/or contain phosphors in the region of the vocal cords, enhancing visualization of the target vocal cords. In another implementation of the laryngoscope, the laryngoscope blade carries a black light source and a white light source. A switch on the laryngoscope enables the health care provide to actuate the black light source, the white light source, or to activate both light sources.

An additional aspect of the invention involves a laryngoscope for use in viewing the vocal cords of a patient in performance of an endotracheal intubation. The laryngoscope includes a handle to be gripped by a medical professional in performing the endotracheal intubation; a blade portion extending from the handle to lift the patient's tongue and mandible for viewing the vocal cords and aid in the insertion of an endotracheal tube; a power source; and a black light source powered by the power source and carried by the blade portion to prompt the visible effects of fluorescence and phosphorescence with respect to the patient's vocal cords for viewing the vocal cords and passing of the endotracheal tube there between during endotracheal intubation.

Another aspect of the invention involves an endotracheal intubation system for performing an endotracheal intubation including the laryngoscope described immediately above; and an endotracheal tube insertable into the patient's mouth, between the patient's vocal cords into the patient's larynx, and into the patient's trachea for opening the patient's airway.

A further aspect of the invention involves a method of performing an endotracheal intubation including using the laryngoscope described immediately above to lift the patient's tongue and mandible for viewing the vocal cords and aid in the insertion of an endotracheal tube; illuminating the patient's vocal cords with the black light source to prompt the visible effects of fluorescence and phosphorescence with respect to the patient's vocal cords for viewing the vocal cords; and simultaneously visualizing the patient's vocal cords with the black light source and sliding the endotracheal tube between the patient's vocal cords and into the patient's larynx and trachea.

A still further aspect of the invention involves a laryngoscope blade for use in viewing the vocal cords of a patient in performance of an endotracheal intubation. The laryngoscope blade includes a laryngoscope blade portion connectable to a laryngoscope handle to lift the patient's tongue and mandible for viewing the vocal cords and aid in the insertion of an endotracheal tube; and a black light source carried by the blade portion to prompt the visible effects of fluorescence and phosphorescence with respect to the patient's vocal cords for viewing the vocal cords and passing of the endotracheal tube there between during endotracheal intubation.

According to another embodiment, a laryngoscope for use in viewing the vocal cords of a patient in performance of an endotracheal intubation includes a handle to be gripped by a medical professional in performing the endotracheal intubation, and a blade portion pivotally connected to a first/upper end of the handle and extending from the handle to lift the patient's tongue and mandible for viewing the vocal cords and for aiding in the insertion of an endotracheal tube. The handle is of an ergonomically curved or angled overall shape, and has an inner surface with a series of arcuate finger grip indents. In one embodiment, an outwardly projecting blade stop is formed integrally on the inner surface of the handle adjacent the upper end, and prevents the blade from touching the handle. The handle may be curved continuously along all or most of its length in an ergonomic shape for comfortable gripping by the user. Alternatively, the handle may have a first end portion extending from one end up to an angled bend, and a second end portion extending from the bend at an angle to the first portion.

Another aspect of the invention involves a laryngoscope handle of a laryngoscope for use in viewing the vocal cords of a patient in performance of an endotracheal intubation, the laryngoscope including a laryngoscope blade connectable to the handle to lift the patient's tongue and mandible for viewing the vocal cords and aid in the insertion of an endotracheal tube. The laryngoscope handle includes a first end; a second end; an inner surface which faces towards a patient during use; and an outer surface, wherein the inner surface of the handle having a plurality of spaced finger grip indents along at least part of the length of the handle between the first and second ends.

One or more implementations of the aspect of the invention described immediately above includes one or more of the following: the handle is at least one of angled and curved to direct the second end towards the blade, when the blade is connected to the handle; the outer surface of the handle includes a convex surface with a radius of curvature in the range of 3 to 5 inches; the outer surface of the handle includes a thumb engaging section with a thumb location for engaging the laryngoscope handle with one's thumb; the thumb engaging section includes an elongated recessed section; the thumb engaging section includes an indicia to indicate proper orientation of the laryngoscope handle; the thumb location is located near the second end of the laryngoscope handle, and further including a second thumb location near the first end of the laryngoscope handle; the plurality of spaced finger grip indents include four spaced finger grip indents; the four spaced finger grip indents include a first finger grip indent that receives an index finger, a second finger grip indent that receives a middle finger, a third finger grip indent that receives a third finger, and a fourth finger grip indent that receives a little finger; the plurality of spaced finger grip indents include three spaced finger grip indents; the three spaced finger grip indents include a first finger grip indent that receives a middle finger, a second finger grip indent that receives a third finger, and a third finger grip indent that receives a little finger; the laryngoscope blade is connected to the second end of the laryngoscope handle, the laryngoscope blade carrying a black light source to prompt the visible effects of fluorescence and phosphorescence with respect to the patient's vocal cords for viewing the vocal cords, providing visible definition of the other structures, and passing of the endotracheal tube there between during endotracheal intubation, the black light source emitting electromagnetic radiation having a wavelength in the range of 300 to 450 nm; the laryngoscope blade includes a proximal portion, a distal portion, and a white light source, and the black light source is located closer to the distal portion and the white light is located closer to the proximal portion; the handle has a bend which separates the handle into a first end portion and a second end portion which is bent at an angle in the range from 40 to 60 degrees relative to the first end portion; and/or the blade is pivotally connectable to the handle and the inner surface of the handle has a blade stop projection extending towards the blade, when the blade is pivotally connected to the handle, which restricts contact between the handle and blade, when the blade is pivoted towards the handle.

A further aspect of the invention involves a laryngoscope handle of a laryngoscope for use in viewing the vocal cords of a patient in performance of an endotracheal intubation, the laryngoscope including a laryngoscope blade connectable to the handle to lift the patient's tongue and mandible for viewing the vocal cords and aid in the insertion of an endotracheal tube. The laryngoscope handle includes a first end; a second end; an inner surface which faces towards a patient during use; and an outer surface, wherein the handle is at least one of angled and curved to direct the second end towards the blade, when the blade is connected to the handle.

One or more implementations of the aspect of the invention described immediately above includes one or more of the following: the inner surface of the handle having a plurality of spaced finger grip indents along at least part of the length of the handle between the first and second ends; the outer surface of the handle includes a convex surface with a radius of curvature in the range of 3 to 5 inches; the outer surface of the handle includes a thumb engaging section with a thumb location for engaging the laryngoscope handle with one's thumb; the thumb engaging section includes an elongated recessed section; the thumb engaging section includes an indicia to indicate proper orientation of the laryngoscope handle; the thumb location is located near the second end of the laryngoscope handle, and further including a second thumb location near the first end of the laryngoscope handle; the plurality of spaced finger grip indents include four spaced finger grip indents; the four spaced finger grip indents include a first finger grip indent that receives an index finger, a second finger grip indent that receives a middle finger, a third finger grip indent that receives a third finger, and a fourth finger grip indent that receives a little finger; the plurality of spaced finger grip indents include three spaced finger grip indents; the three spaced finger grip indents include a first finger grip indent that receives a middle finger, a second finger grip indent that receives a third finger, and a third finger grip indent that receives a little finger; the laryngoscope blade is connected to the second end of the laryngoscope handle, the laryngoscope blade carrying a black light source to prompt the visible effects of fluorescence and phosphorescence with respect to the patient's vocal cords for viewing the vocal cords, providing visible definition of the other structures, and passing of the endotracheal tube there between during endotracheal intubation, the black light source emitting electromagnetic radiation having a wavelength in the range of 300 to 450 nm; the laryngoscope blade includes a proximal portion, a distal portion, and a white light source, and the black light source is located closer to the distal portion and the white light is located closer to the proximal portion; the handle has a bend which separates the handle into a first end portion and a second end portion which is bent at an angle in the range from 40 to 60 degrees relative to the first end portion; and/or the blade is pivotally connectable to the handle and the inner surface of the handle has a blade stop projection extending towards the blade, when the blade is pivotally connected to the handle, which restricts contact between the handle and blade, when the blade is pivoted towards the handle.

An additional aspect of the invention involves a laryngoscope blade for use in viewing the vocal cords of a patient in performance of an endotracheal intubation. The laryngoscope blade includes a laryngoscope blade portion connectable to a laryngoscope handle to lift the patient's tongue and mandible for viewing the vocal cords and aid in the insertion of an endotracheal tube, the laryngoscope blade portion includes a proximal portion and a distal portion; a white light source carried by the laryngoscope blade portion; a black light source carried by the blade portion to prompt the visible effects of fluorescence and phosphorescence with respect to the patient's vocal cords for viewing the vocal cords, providing visible definition of the other structures, and passing of the endotracheal tube there between during endotracheal intubation, the black light source located closer to the distal portion and the white light located to the proximal portion, and the black light source emitting electromagnetic radiation having a wavelength in the range of 300 to 450 nm.

One or more implementations of the aspect of the invention described immediately above includes one or more of the following: the black light source emits electromagnetic radiation having a wavelength in the range of 385 to 395 nm; the white light source is a cool white LED with a mcd rating of 100-10,000 millicandela (mcd); an electrical circuit including the white light source and a 150 ohm resistor associated with the white light source to provide 5 ma at 2.9 volts; an electrical circuit including the black light source and a 13 ohm resistor so that the distal black light source is at 49-50 ma at 3.6 volts; an electrical circuit including a 4.5 volt power source; an endotracheal intubation system for performing an endotracheal intubation, including a laryngoscope including the laryngoscope blade described in the aspect of the invention described immediately above; and an endotracheal tube insertable into the patient's mouth, between the patient's vocal cords into the patient's larynx, and into the patient's trachea for opening the patient's airway, the endotracheal tube includes a distal portion and an expandable body near the distal portion, the distal portion includes a dimension, and the expandable body includes a dimension less than the dimension of the distal portion of the expandable body during intubation and a dimension greater than the dimension of the distal portion of the expandable body to secure the endotracheal tube in place in the trachea; the distal portion includes a recessed section that carries the expandable body, and the expandable body is recessed in the recessed section so that the expandable body includes a dimension less than the dimension of the distal portion of the expandable body during intubation and so that the expandable body expands to a dimension outside of the recessed section, greater than the dimension of the distal portion, to secure the endotracheal tube in place in the trachea; the distal portion includes a movable sheath that covers the expandable body during intubation and is movable to uncover the expandable body so that the expandable body is expandable to a dimension greater than the dimension of the distal portion, to secure the endotracheal tube in place in the trachea; the distal portion includes at least one of a fluorescent and phosphorescent material that is at least one of enhanced by and reacts to the black light source to aid in visibility and positioning of the endotracheal during intubation; an endotracheal intubation system for performing an endotracheal intubation, including a laryngoscope including the laryngoscope blade of the aspect of the invention described immediately above; an endotracheal tube insertable into the patient's mouth, between the patient's vocal cords into the patient's larynx, and into the patient's trachea for opening the patient's airway; and a stylet for the endotracheal tube, the stylet including at least one of a fluorescent and phosphorescent material that is at least one of enhanced by and reacts to the black light source to aid in visibility and positioning of at least one of the stylet and the endotracheal tube; and/or an endotracheal intubation system for performing an endotracheal intubation, including a laryngoscope including the laryngoscope blade of the aspect of the invention described immediately above; an endotracheal tube insertable into the patient's mouth, between the patient's vocal cords into the patient's larynx, and into the patient's trachea for opening the patient's airway; an endotracheal tube introducer including at least one of a fluorescent and phosphorescent material that is at least one of enhanced by and reacts to the black light source to aid in visibility and positioning of at least one of the endotracheal tube introducer and the endotracheal tube.

A further aspect of the invention involves an introducer including a distal portion, an intermediate portion, and a proximal portion, wherein one or more of the distal portion, the intermediate portion, and the proximal portion including at least one of a fluorescent and phosphorescent material that is at least one of enhanced by and reacts to the black light source to aid in visibility and positioning of the introducer.

One or more implementations of the aspect of the invention described immediately above include one or more of the following: the introducer includes a polyethylene body; the introducer is at least one of an endotracheal tube introducer and an orotracheal intubation introducer; the introducer includes smooth outer ends; and/or the introducer includes a length of 50-70 cm.

A still further aspect of the invention involves an endotracheal intubation tube for performing an endotracheal intubation, the endotracheal intubation tube insertable into the patient's mouth, between the patient's vocal cords into the patient's larynx, and into the patient's trachea for opening the patient's airway. The endotracheal intubation tube includes an endotracheal tube body; a distal portion; and an expandable body near the distal portion, wherein the distal portion includes a dimension, and the expandable body includes a dimension less than the dimension of the distal portion of the expandable body during intubation and a dimension greater than the dimension of the distal portion of the expandable body to secure the endotracheal tube in place in the trachea.

One or more implementations of the aspect of the invention described immediately above includes one or more of the following: the distal portion includes a recessed section that carries the expandable body, and the expandable body is recessed in the recessed section so that the expandable body includes a dimension less than the dimension of the distal portion of the expandable body during intubation and so that the expandable body expands to a dimension outside of the recessed section, greater than the dimension of the distal portion, to secure the endotracheal tube in place in the trachea; the distal portion includes a movable sheath that covers the expandable body during intubation and is movable to uncover the expandable body so that the expandable body is expandable to a dimension greater than the dimension of the distal portion, to secure the endotracheal tube in place in the trachea; and/or a stylet for the endotracheal tube, the stylet including at least one of a fluorescent and phosphorescent material that is at least one of enhanced by and reacts to the black light source to aid in visibility and positioning of at least one of the stylet and the endotracheal tube.

Another aspect of the invention involves a removable sheath to cover a distal portion of an endotracheal tube and protect an expandable body thereon, the removable sheath removable prior to insertion of the endotracheal tube into the patient's mouth.

One or more implementations of the aspect of the invention described immediately above includes one or more of the following: the removable sheath includes a substantially tubular portion that covers the distal portion of the endotracheal tube and protect the expandable body; the removable sheath includes a finger portion engageable by a user's finger to facilitate removal of the removable sheath from the distal portion of the endotracheal tube; the finger portion includes a finger hole engageable by a user's finger to facilitate removal of the removable sheath from the distal portion of the endotracheal tube; and/or the removable sheath carries a lubricant for lubricating the distal portion and the expandable body of the endotracheal tube.

Further objects and advantages will be apparent to those skilled in the art after a review of the drawings and the detailed description of the preferred embodiments set forth below.

BRIEF DESCRIPTION OF THE DRAWINGS

FIG. 1 is a schematic depiction of a laryngoscope being used to view a patient's larynx;

FIG. 2 is a perspective view of a laryngoscope in accordance with an embodiment of the present invention;

FIG. 3A is a bottom plan view of the laryngoscope of FIG. 2, and illustrates an embodiment of a switch that may be used with the of the laryngoscope of FIG. 2;

FIG. 3B is a bottom plan view of an alternative embodiment of a laryngoscope, and illustrates an embodiment of a black light source on the bottom of the laryngoscope;

FIG. 6 is an alternative embodiment of an endotracheal tube that may be used with the laryngoscope of FIGS. 1-3 or a standard laryngoscope.

FIG. 8 is a side-elevational view of a separate laryngoscope blade in accordance with an embodiment of the present invention;

FIG. 9 is a side-elevational view of a separate laryngoscope blade in accordance with another embodiment of the present invention;

FIG. 10 is a side-elevational view of an embodiment of a pair of forceps;

FIG. 21 is a left elevational view of the laryngoscope illustrated in FIG. 17.

FIG. 22 is a rear elevational view of the laryngoscope illustrated in FIG. 17.

FIG. 23 is a top plan view of the laryngoscope illustrated in FIG. 17.

FIG. 37A is a partial perspective view of another embodiment of an endotracheal tube with a balloon and movable cuff sheath and shows the distal portion of the endotracheal tube with the movable cuff sheath in an extended position where it covers the balloon.

FIG. 37B is a partial perspective view of the endotracheal tube of FIG. 37A and shows the distal portion of the endotracheal tube with the movable cuff sheath in a retracted position where the balloon is not covered and is in an expanded configuration.

FIG. 38A is a partial front elevational view of a further embodiment of an endotracheal tube with a balloon shown in a collapsed, low-profile position.

FIG. 38B is a partial front elevational view of the endotracheal tube of FIG. 38A and shows the balloon in an expanded configuration.

FIGS. 44A, 44B, 44C, 44D, 44E, 44F, and 44G are right side elevational, rear elevational, left side elevational, perspective, front elevational, bottom plan, and top plan views of an additional embodiment of a laryngoscope blade.

FIGS. 45A, 45B, 45C, 45D, 45E, 45F, and 45G are right side elevational, rear elevational, left side elevational, perspective, front elevational, bottom plan, and top plan views of another embodiment of a laryngoscope blade.

FIGS. 49A, 48B, 49C, 49D, 49E, 49F, and 49G are right side elevational, rear elevational, left side elevational, perspective, front elevational, bottom plan, and top plan views of a yet further embodiment of a laryngoscope blade.

DETAILED DESCRIPTION OF PREFERRED EMBODIMENTS

Figure 4:
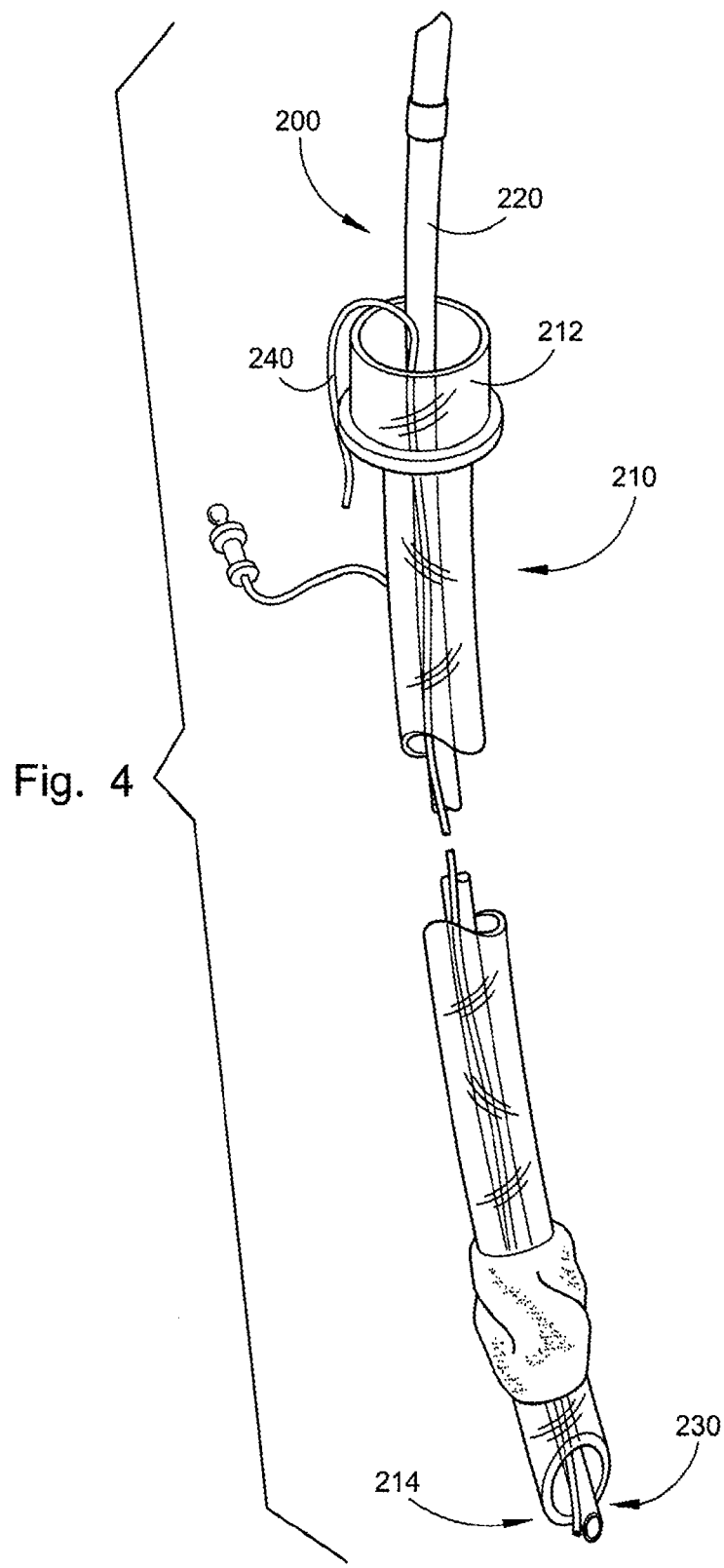
FIG. 4 is an embodiment of an endotracheal tube that may be used with the laryngoscope of FIGS. 1-3.

With reference to FIGS. 1 and 2, a laryngoscope 100 constructed in accordance with an embodiment of the invention will be described. In FIG. 1, the laryngoscope 100 is shown placed in the mouth of a patient 112 for viewing the vocal cords adjacent the larynx and to aid in the insertion of an endotracheal tube 200 (FIG. 4) past the vocal cords. The laryngoscope 100 includes a handle or handgrip 114 and a blade portion 116, the latter being used to lift the tongue and mandible 118 out of the way for viewing the vocal cords.

As shown in FIG. 2, the blade portion 116 is pivotally connected to a handle cap 120. The blade portion 116, the handle cap 120, and the handle 114 can be readily assembled together for use. In the embodiment shown, when assembled, a white light source 150 and a black light source 160 are automatically actuated. In an alternative embodiment, the blade portion 116 is directly connected to a top of the handle 114 (i.e., there is no handle cap). The handle 114 is essentially a hollow tube having a closed lower or outer end 124 (FIG. 3) and an open upper end. The handle cap 120 is removably secured to an open upper end of the handle 114. A power source 123 (e.g., one or more dry cell batteries) is located within the handle cavity to provide power for light source(s) to be described.

A side of the handle 114 includes a switch 128 in the form of two pressure/push buttons 129, 130 interconnected with the power source 123, the white light source 150, and the black light source 160 that, when pressed (e.g., by a user's thumb), deactivate the respective light sources 150, 160. When the laryngoscope 100 is clicked together/assembled, both light sources 150, 160 are placed in electrical communication with the power source 123 and are automatically turned on. In the embodiment shown, push button ("white light button") 129 controls the white light source 150 so that pushing on the white light button 129 turns off the white light source 150 and push button ("black light button") 130 controls the black light source 160 so that pushing on the black light button 130 turns off the black light source 160. Thus, by applying pressure to the push buttons 129, 130, the respective light sources 150, 160 are turned off. Removing the pressure to the push buttons 129, 130 causes the respective light sources 150, 160 to be turned back on. Accordingly, the switch 128 enables the laryngoscope 100 to be switched between at least a "both on" condition where both black light is emitted from the black light source 160 and white light is emitted from the white light source 150, a black light condition where black light is emitted from the black light source 160 and the white light source 150 is off, and a white light condition where white light is emitted from the white light source 150 and the black light source 160 is off.

With reference to FIG. 3, an alternative embodiment of a switch 131 located on a bottom 124 of the handle 114 is shown. The switch 131 cooperates with electronics in the laryngoscope 100 for switching between an "off" condition, a black light condition, a white light condition, and a "both on" condition. In the embodiment shown, the switch 131 is a rotating switch with a rotating knob 132 that rotates between different positions to actuate the above conditions.

In alternative embodiments, other types of switches may be used (e.g., push-button switch, a toggle switch) on the bottom 124 of the handle 114 (or at other locations on the laryngoscope 100) to switch between an "off" condition and one or more of a black light condition, a white light condition, and a "both on" condition. In alternative embodiments, the switch 128, 131 may switch between conditions in addition to or other than an "off" condition, a black light condition, a white light condition, and a "both on" condition. For example, in an alternative embodiment, where the laryngoscope 100 includes only a black light source 160, the switch 128, 131 may switch the laryngoscope 100 between an "off" condition and a black light condition.

One or more light sources 140 are interconnected with the power source 123 in the handle 114. In the embodiment shown, as discussed above, the one or more light sources 140 include two light sources: 1) a white light source 150, and 2) a black light source 160. Example white light sources 150 include, but not by way of limitation, a white halogen light, a white incandescent light, and a white LED. The black light source 160 emits long wave UVA radiation and very little visible light. The black light source is a lamp emitting electromagnetic radiation that is almost exclusively in the soft near ultraviolet range. The black light source 160 prompts the visible effects of fluorescence and phosphorescence with respect to the patient's vocal cords and the glottis, which is the space between the vocal cords, during laryngoscopy. The black light source 160 may be a Wood's light made using Wood's glass, which is a nickel-oxide-doped glass, which blocks substantially all visible light above 400 nanometers. In alternative embodiments, other black light sources 160 (e.g., LED(s)) may be used. In one embodiment, the black light source 160 emits electromagnetic radiation including a wavelength in the range of 315 to 400 nm, with out emitting substantial electromagnetic radiation including a wavelength outside of the range of 315 to 400 nm. In another embodiment, the black light source 160 includes a wavelength of 385-395 nm.

In the embodiment shown, the blade portion 116 is a curved Macintosh blade; however, in alternative embodiments, other types of blades (e.g., straight Miller/Robertshaw blade) may be used. The blade portion 116 carries the one or more light sources 140. Although the one or more light sources 140 are shown on a top of the blade portion 116, in alternative embodiments, the one or more light sources 140 are disposed at one or more of the following locations: a side of the blade portion 116, a bottom of the blade portion 116, a top of the blade portion 116, a distal tip of the blade portion 116, and other locations on or relative to the blade portion 116.

With reference to FIG. 3B, in a further embodiment, in addition to or instead of the one or more light sources 140 being carried by the blade portion 116, a black light source (e.g., black light source 160) is carried by the bottom 124 of the handle 114 for emitting black light from the bottom 124 of the handle 114. In such an embodiment, a switch (e.g., switch 128) for controlling the black light source on the bottom 124 of the handle 114 is preferably located in a location other than the bottom 124 of the handle 114.

With reference to FIG. 4, an embodiment of an endotracheal tube 200 that may be used with the laryngoscope 100 (as part of an endotracheal intubation system) in performing endotracheal intubation will be described. The endotracheal tube 200 includes a clear plastic intubation tube 210 with an elongated central lumen. The intubation tube 210 includes a larger-diameter open upper end 212, which may include a cap, and a pointed open lower end or tip 214. An elongated scope (e.g., a fiberoptic scope) 220 may be received within the lumen of the intubation tube 210. The scope 220 includes a distal viewing tip 230. A plastic transparent holding sheath may cover the scope 220. A longitudinally built-in narrow malleable metal intubation stylet 240, which is a narrow piece of flat metal, may be built into the holding sheath and adhered to an outer wall of the holding sheath for controlling the geometry/shape of the scope 220/endotracheal tube 200 to match the physiology/anatomy of the patient during endotracheal intubation.

In an alternative embodiment, one or more of the intubation tube 210 and the stylet 240 include a fluorescent color or other color/substance that is enhanced by the black light or that reacts to the black light (on the entire tube 210/stylet 240 or a portion and/or component there of).

For example, but not by way of limitation, in one or more embodiments, the intubation tube 200 includes a fluorescent striping on the body of the ET tube 210, fluorescent coloring of the balloon/cuff shown near the distal end of the tube 200, and/or on the BVM connector near proximal end of tube 200 causes device to naturally phosphoresce under black light, clearly identifying ET tube tracking through the vocal cords into the trachea.

A method of performing endotracheal intubation using the laryngoscope 100 and the endotracheal tube 200 will be described. The black light source 160 of the laryngoscope 100 is activated (e.g., when the laryngoscope 100 is clicked together/assembled). The blade portion 160 of the laryngoscope 100 is inserted into the patient's mouth and behind the patient's tongue and mandible 118. By gripping the handle 114 with one's hand, the tongue and mandible 118 are lifted for viewing the vocal cords adjacent the larynx and to aid in the insertion of the endotracheal tube 200 past the vocal cords. The black light emitted from the laryngoscope 100 prompts the visible effects of fluorescence and phosphorescence with respect to the patient's vocal cords and the glottis, making the patient's vocal cords and the glottis visible either directly by the eyes of the medical provider or via the scope 220 of the endotracheal tube 200. The endotracheal tube 200 is inserted into the patient's mouth, between the patient's visible vocal cords into the larynx, and then into the trachea of the patient in a usual manner. The stylet 200 of the endotracheal tube 200 may be used to shape the scope 220/endotracheal tube 200 to the individual anatomy/pathology of the patient.

As discussed above, in the embodiment of the laryngoscope 100 shown in FIG. 1, applying pressure to the push buttons 129, 130 causes the respective light sources 150, 160 to be deactivated and removing the pressure to the push buttons 129, 130 causes the respective light sources 150, 160 to be re-activated. The medical provider operates the push buttons 129, 130 of the switch 128 (e.g., to cause only black light to be emitted, only white light to be emitted, or both types of light to be emitted) so that optimal viewing of the vocal cords occurs. The medical provider may prefer to use the black light condition and/or the white light condition, depending on external lighting conditions, the individual anatomy/pathology of the patient, the patient's condition, and other factors.

Figure 5:
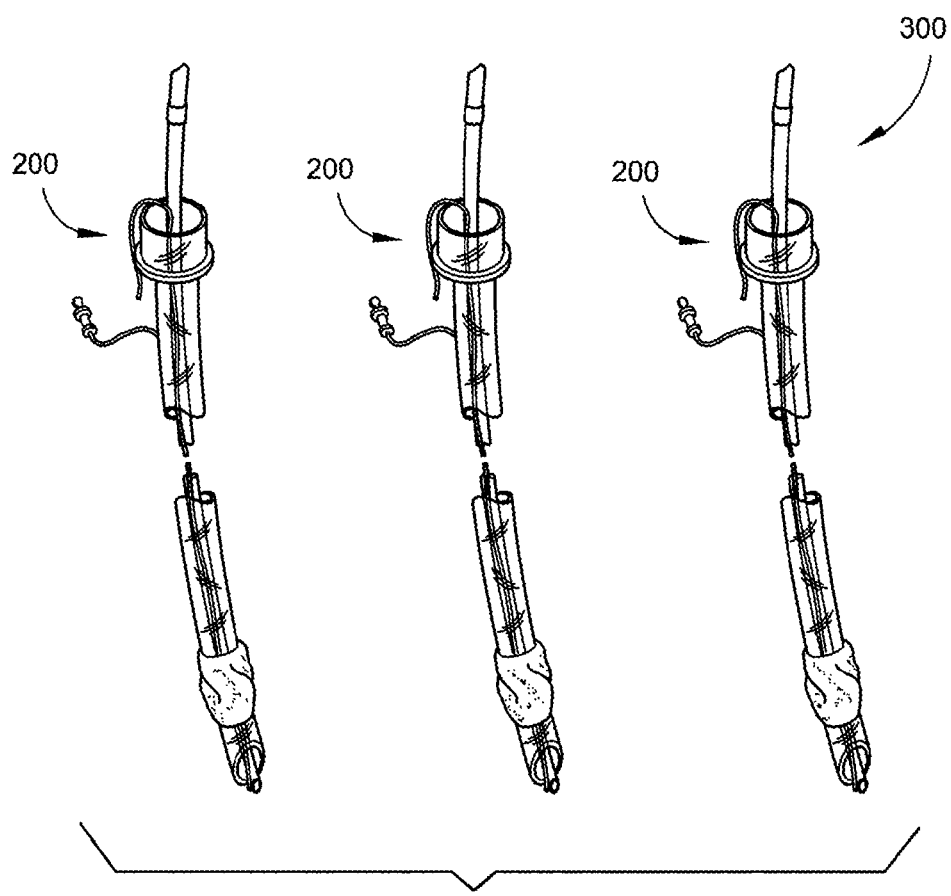
FIG. 5 is an embodiment of a kit of endotracheal tubes that may be used with the laryngoscope of FIGS. 1-3.

With reference to FIG. 5, in another embodiment of the above endotracheal tube 200, a kit 300 of endotracheal tubes 200, intubation tubes 210, and/or stylets 240 of different sizes (e.g., different weight, height, and/or depth; adult version, pediatric version) are color-coded with different fluorescent colors or other color/substance that is enhanced by the black light or that reacts to the black light. For example, but not by way of limitation, the intubation tube 210 of each different endotracheal tube 200 is coated with a unique fluorescent colored material or other color/substance that is enhanced by the black light or that reacts to the black light. The entire endotracheal tube 200 may include a fluorescent color or one or more portions of the endotracheal tube 200 may include one or more fluorescent colors (or other color/substance that is enhanced by the black light or that reacts to the black light). For example, but not by way of limitation, a cap of the endotracheal tube 200 may include a unique fluorescent color (or other color/substance), the intubation tube 210 may include a unique fluorescent color (or other color/substance), and/or the stylet 240 may include a unique fluorescent color (or other color/substance) for identifying the proper size endotracheal tube 200, intubation tube 210, and/or stylet 240, and for improving visualization of the endotracheal tube 200, intubation tube 210, and/or stylet 240 during endotracheal intubation. Using the black light source 160 of the laryngoscope 100, one may easily identify the correct-sized endotracheal tube 200, intubation tube 210, and/or stylet 240 by shining black light on the kit of endotracheal tubes 200, intubation tubes 210, and/or stylets 240 identified by different fluorescent colors (or other color/substance) so that the proper-sized endotracheal tube 200, intubation tube 210, and/or stylet 240 for the patient/application is selected. The different-size/fluorescent-color endotracheal tubes 200, intubation tubes 210, and/or stylets 240 are easy to identify with a black light source, especially in no-light, low-light, or dark conditions. Further, the fluorescent (or other color/substance) endotracheal tube 200, intubation tube 210, and/or stylet 240, in combination with the black light laryngoscope 100, improves visualization of the endotracheal tube 200, intubation tube 210, and/or stylet 240 passing the vocal cords during endotracheal intubation.

With reference to FIG. 6, in another embodiment, the stylet 240 and/or the endotracheal tube 200 includes a black light source 350 that emits black light to enhance visualization of the vocal cords during endotracheal intubation. For example, the stylet 240 and/or the endotracheal tube 200 with black light source 250 may be used in conjunction with the laryngoscope 100 discussed above with respect to FIGS. 1-3, or in conjunction with a normal laryngoscope that does not have a black light source 150.

Figure 7:
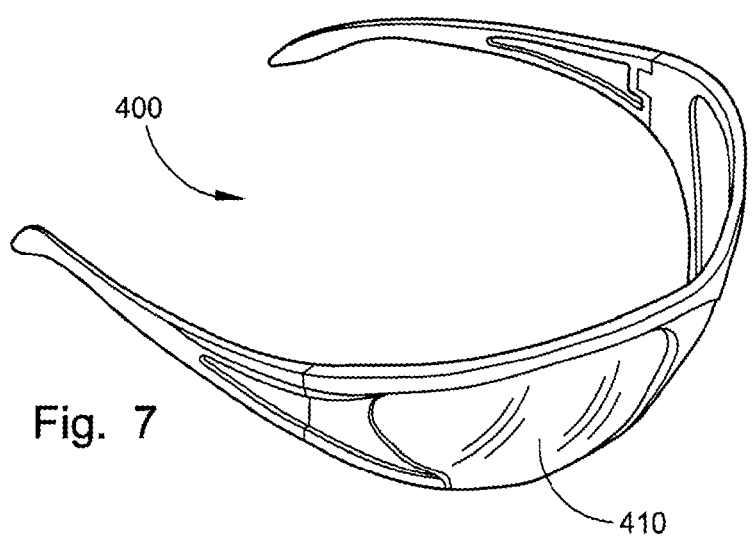
FIG. 7 is an embodiment of a pair of protection intubation glasses that may be used with the laryngoscope of FIGS. 1-3 and/or the endotracheal tube(s) of FIGS. 4-6.

With reference to FIG. 7, an embodiment of a pair of protection intubation glasses 400 includes lenses 410 configured (e.g., tinted to a particular shade) so that when used in conjunction with the black light sources described above during endotracheal intubation, the visibility of the vocal cords is intensified/enhanced.

With reference to FIG. 8, an embodiment of a separate laryngoscope blade 500 that may be detachably connected to a separate laryngoscope handle (e.g., handle 114) will be described. In the embodiment shown, the blade 500 is a curved Macintosh blade; however, in alternative embodiments, other types of blades (e.g., straight Miller/Robertshaw blade) may be used.

The blade 500 may be made of stainless steel, plastic, or a combination of stainless steel and plastic. In other embodiments, other materials are used.

The blade 500 includes a blade portion 516 with a distal portion 530 and a proximal portion 540. The blade portion 516 carries a white light source 150 and a black light source 160. The black light source 160 is located distally of (i.e., closer to the distal portion 530 relative to) the white light source 150 on the blade portion 516. The advantage of locating the black light source 160 distally of the white light source 150 is that, in use, the proximal white light source 150 provides general illumination (e.g., of the interior of the mouth and back of the patient's throat) while the distal black light source 160, which is disposed closer to the patient's vocal cords and the glottis, provides directed black light illumination of the patient's vocal cords and the glottis, prompting the visible effects of fluorescence and phosphorescence with respect to the patient's vocal cords and the glottis. In another embodiment (FIGS. 17-23), the distal black light source 160 is disposed 1.5 to 2.0 inches in front of proximal white light source 150. In alternative embodiments, the white light source 150 and/or the black light source 160 are located at other positions/locations/relative distances than those shown.

The blade 500 includes a connection section 550 for mechanically coupling the blade 500 to a top of the separate laryngoscope handle and electrically coupling the white light source 150 and the black light source 160 to a power source in the laryngoscope handle. Alternatively, the blade 500 carries its own power source for powering the white light source 150 and the black light source 160. When the blade 500 is connected to the laryngoscope handle, the connection section 550 is configured so that both the white light source 150 and the black light source 160 are automatically activated and when the blade 500 is disconnected to the laryngoscope handle, the white light source 150 and the black light source 160 are automatically deactivated. This automatic activation/deactivation may be achieved by electrical connectors and/or switch(es) (e.g., an electrically conductive ball contact on connection portion of handle and a cooperating electrically conductive ball contact on connection portion of blade 500 that contact each other to close the circuit when the blade 500 and the handle are connected and lose contact with each other to open the circuit when the blade 500 and the handle of disconnected). For example, the mechanical connection between the connection section 550 and the laryngoscope handle may put the power source in the handle in electrical communication with the white light source 150 and the black light source 160 or may cause a switch at the interface of the connection section 550 and the laryngoscope handle to be closed. In an alternative embodiment, the blade 500 and/or laryngoscope handle carries a user controllable switch to control activation/deactivation of the white light source 150 and the black light source 160 (e.g., both on, both off, one on and one off).

FIG. 9 illustrates another embodiment of a separate laryngoscope blade 600 that is the same as the blade 500, except the blade 600 includes only a black light source 160 instead of both a white light source 150 and a black light source 160.

With reference to FIG. 10, an embodiment of a pair of stainless steel disposable forceps 700 including distal portions 710 of jaws 720 coated with (e.g., dipped in) a fluorescent colored material/substance (or other color/substance) that is enhanced by the black light or that reacts to the black light is shown. In an alternative embodiment, the forceps 700 are made of a plastic material including the fluorescent colored material/substance (or other color/substance) that is enhanced by the black light or that reacts to the black light.

The forceps 700 include a handle 730 at a proximal end and the distal jaws 720 at an opposite end for gripping an object. The forceps 700 pivot about a pivot section 740. In use, the forceps 700 are used to grip an object (e.g., to remove an object from the patient's body). Black light (e.g., from any of the black light devices described above and shown herein) is directed at the object and the jaws 720 of the forceps 700. The fluorescent colored material/substance is enhanced by the black light, allowing the user to see exactly where to grab the object and, most importantly, not cause damage to surrounding tissue. The user then grabs the object with the jaws 720 of the forceps 700 and, if appropriate, removes the object from the patient's body. Although the forceps 700 in the embodiment shown are Magill-type forceps, in alternative embodiments, other types of forceps with jaws 720 coated with a fluorescent material/substance may be used.

FIGS. 11 to 14 illustrate another embodiment of a laryngoscope 800 having an ergonomically shaped handle 802 and a blade 804 pivotally connected to a first/upper end of the handle via pivot pin 805. In one embodiment, a connection portion 820 of the blade pivots into latching engagement with a suitable conventional latching or click-lock mechanism (not illustrated) at the top of the handle when in the operative position shown in the drawings. In the embodiment shown, the blade is a curved Macintosh blade; however, in alternative embodiments, other types of blades (e.g., straight Miller/Robertshaw blade) may be used. The blade 804 carries one or more light sources (not illustrated) as illustrated and described above in connection with the embodiments of FIGS. 1 to 10, such as light sources 140 on a top surface of the blade as illustrated in FIG. 2. As described in connection with the previous embodiments, the one or more light sources may be a white light source, a black light source, or a black light source and a white light source. The one or more light sources may alternatively be disposed at one or more of the following locations: a side of the blade, a bottom of the blade, a top of the blade, a distal tip of the blade, and other locations on or relative to the blade. The light sources may be any of the alternative types of light sources as described above in connection with the preceding embodiments.

Figure 14:
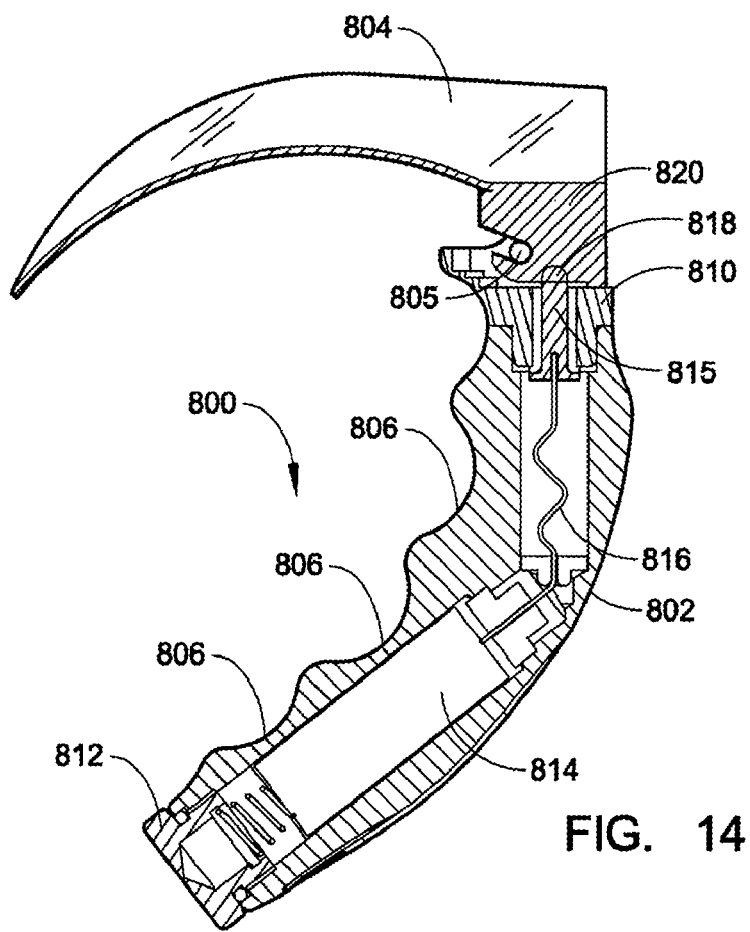
FIG. 14 is a cross-sectional view of the laryngoscope on the lines 14-14 of FIG. 11.

In this embodiment, handle 802 is of a continuously curved, ergonomic shape with a series of four finger grip indents 806 on its inner, concave surface. A projecting blade stop 808 is also located on the inner surface adjacent the first/upper end of the handle. The blade stop 808 may be formed in a first/upper end cap 810 which incorporates the blade pivot mount, as illustrated in FIG. 14. In an alternative embodiment, the blade 804 is directly connected to the first/upper end of the handle 802, eliminating the separate end cap 810 and replacing it with an integrally formed first/upper end portion of the handle 802 of similar shape to end cap 810, including blade stop 808. The handle 802 may be made of any suitable rigid and lightweight material such as metal or plastic.

The first/upper end cap 810 or end portion of the handle 802 is pivotally assembled with the blade 804 in a similar or identical manner to the previous embodiments, and a second/lower end cap 812 is threadably engaged with a lower second/open end of the handle for access to a battery cavity containing a power source 814 (e.g. one or more dry cell batteries such as a lithium battery, single 4.5 volt battery powering a white light source and a black light source carried by the blade 804 in a manner similar to that shown in FIG. 8) which supplies power to the light source or sources, as best illustrated in FIG. 14. As illustrated in FIG. 14, the battery is connected to contact pin 815 in end cap 810 via spring loaded connector wire 816. Contact pin 815 projects into a contact recess 818 in the pivotally mounted portion 820 of the blade. Although not shown in the drawings, it will be understood that the contact in recess 818 is suitably connected to a light source or sources (not illustrated) mounted on the blade 804 in a conventional manner, so that the light source or sources are automatically placed in communication with the power source when the blade 804 is assembled or clicked together with the upper part of the handle 802 in the operative condition of FIGS. 11 to 14, and are automatically turned off when the blade is released or disassembled from the upper part of the handle for storage when not in use, for example when the blade is released from the conventional click lock or latching mechanism (not illustrated) at the first/upper end of the handle and pivoted down towards the handle. The blade stop 808 prevents the blade 804 from contacting the handle when pivoted.

As in the previous embodiments, in alternative embodiments of the laryngoscope 800, other types of switches may be used (e.g., push-button switch, a toggle switch) on the bottom of the handle (or at other locations on the laryngoscope 800) to switch between an "off" condition and one or more of a black light condition, a white light condition, and a "both on" condition. In alternative embodiments, the switch may switch between conditions in addition to or other than an "off" condition, a black light condition, a white light condition, and a "both on" condition.

Figure 11:
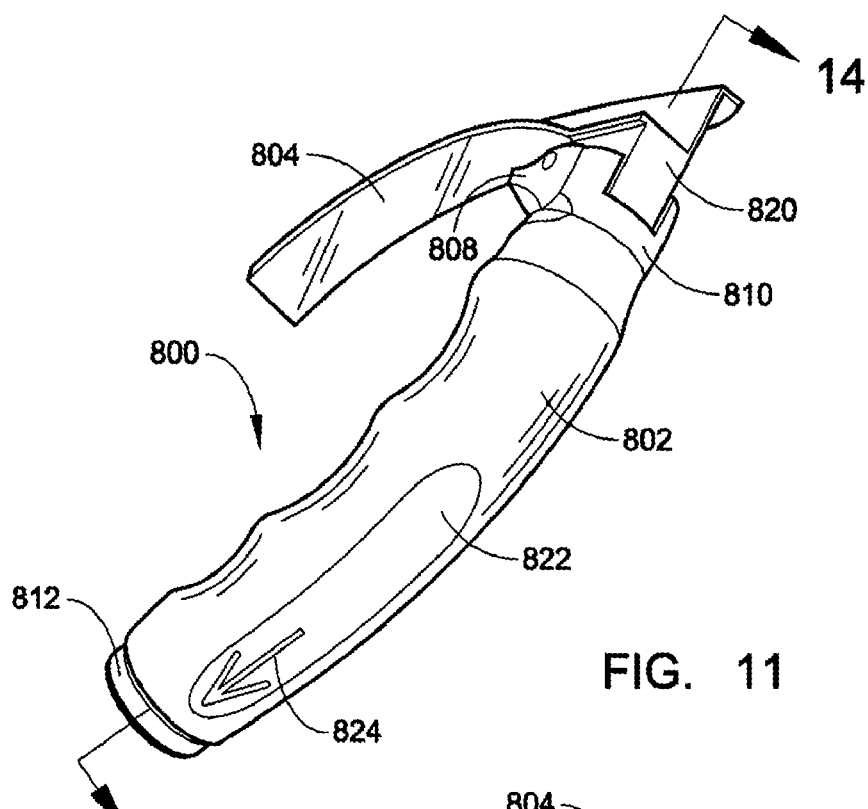
FIG. 11 is a rear perspective view of an alternative embodiment of a laryngoscope with an ergonomically shaped handle.
Figure 12:
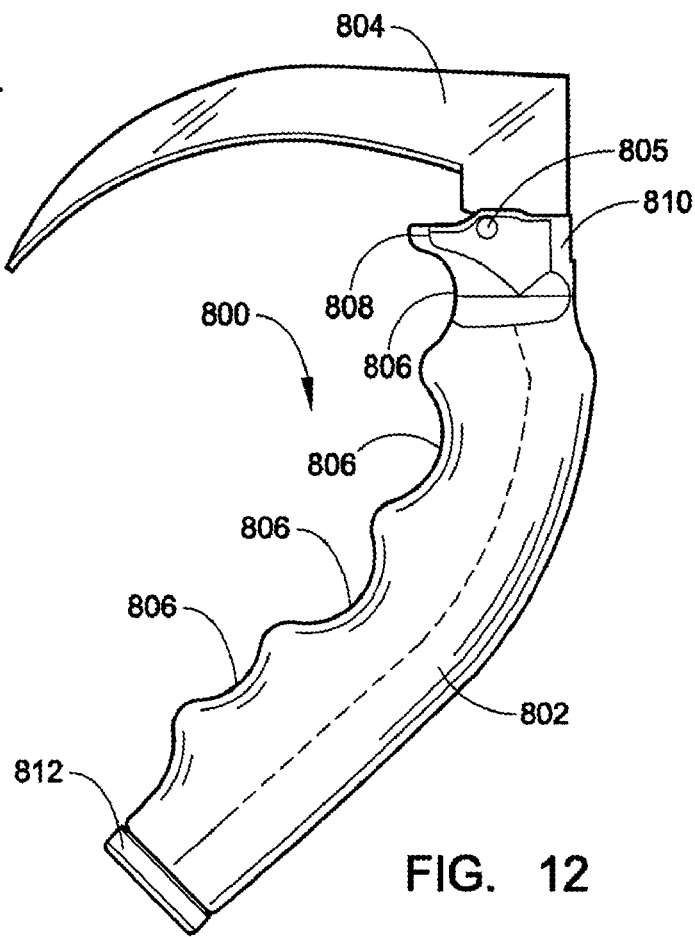
FIG. 12 is a side elevation view of the laryngoscope of FIG. 11.
Figure 13:
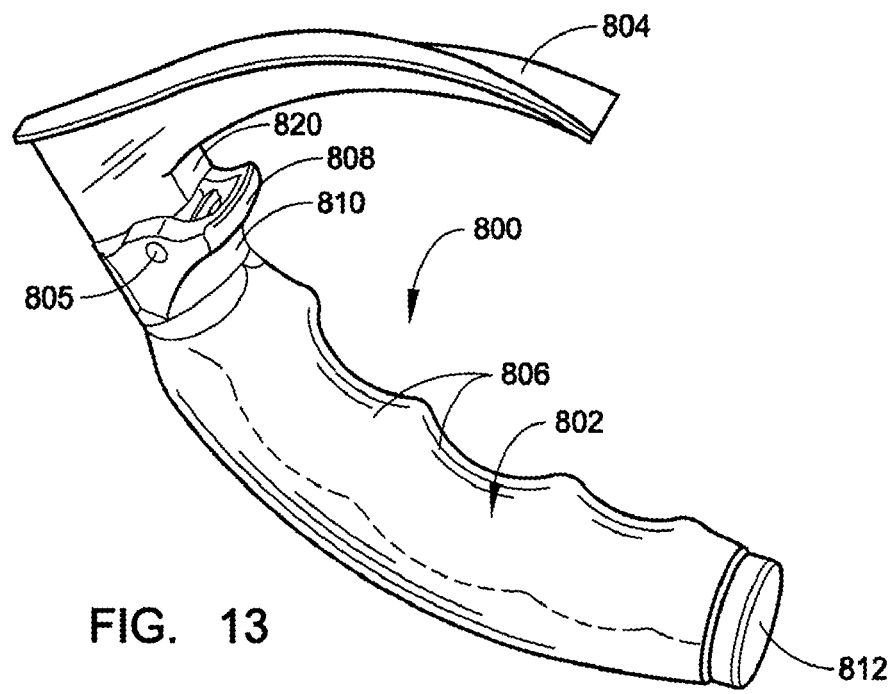
FIG. 13 is a front perspective view of the laryngoscope of FIGS. 11 and 12.

The continuously curved handle along with the finger grips 806 which are gripped by the health care provider during intubation provides an ergonomic design which is easier and more comfortable to use and which is angled more efficiently for proper actuation. As illustrated in FIGS. 11 and 12, the outer, convex surface of the handle is smoothly curved apart from an elongate recessed region 822 in which an arrow sign 824 pointing to the second/lower end of the handle is provided. The arrow 824 provides an indication of the direction of use or manipulation of the handle in order to perform the procedure. The finger grips help the health care provider to hold the device securely and reduce the risk of the handle slipping out of the health care provider's hand.

The handle curvature may be a continuous curve of constant radius of curvature, or may be of varying curvature along at least part of its length. Due to the handle curvature, when the blade 804 is inserted into a patient's mouth as in FIG. 1, the second/lower end portion of the handle 802 bends down rather than upwardly as is the case with straight handle 114 of FIG. 1, making it easier and more efficient for the health care provider to manipulate and position the blade 804 while viewing the patient's trachea during the procedure. The radius of curvature of the outside surface of the handles (FIGS. 11-14, 17-23, and 39) is 4.1 inches. In a preferred embodiment, the radius of curvature of the outside surface of the laryngoscope handle is in the range from 3 to 5 inches. The second/lower end portion of the handle may be bent or curved through an angle of around 40 to 60 degrees relative to the first/upper end of the handle which is attached to the blade.

Figure 15:
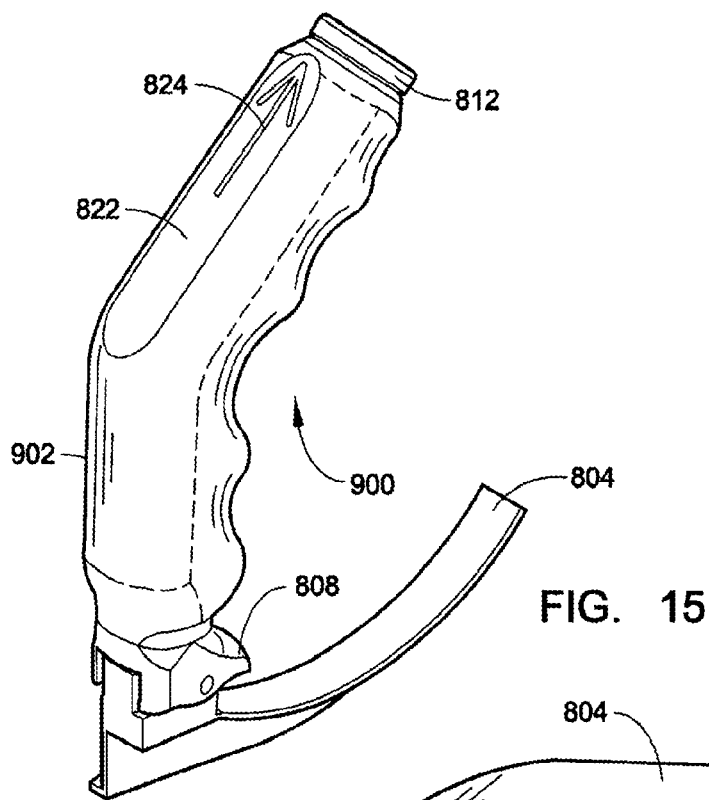
FIG. 15 is a rear perspective view of another embodiment of a laryngoscope with a shaped handle.
Figure 16:
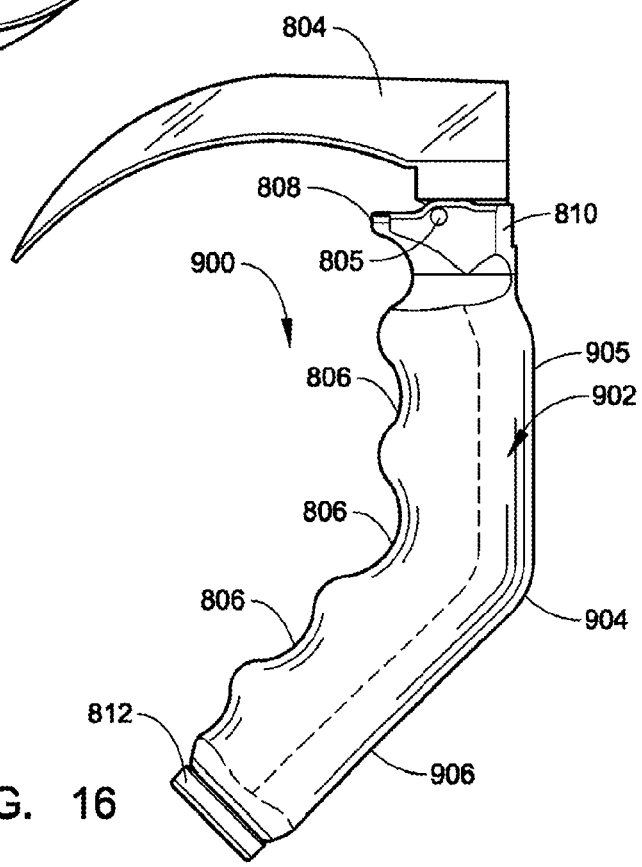
FIG. 16 is a side elevation view of the laryngoscope of FIG. 15.
Figure 17:
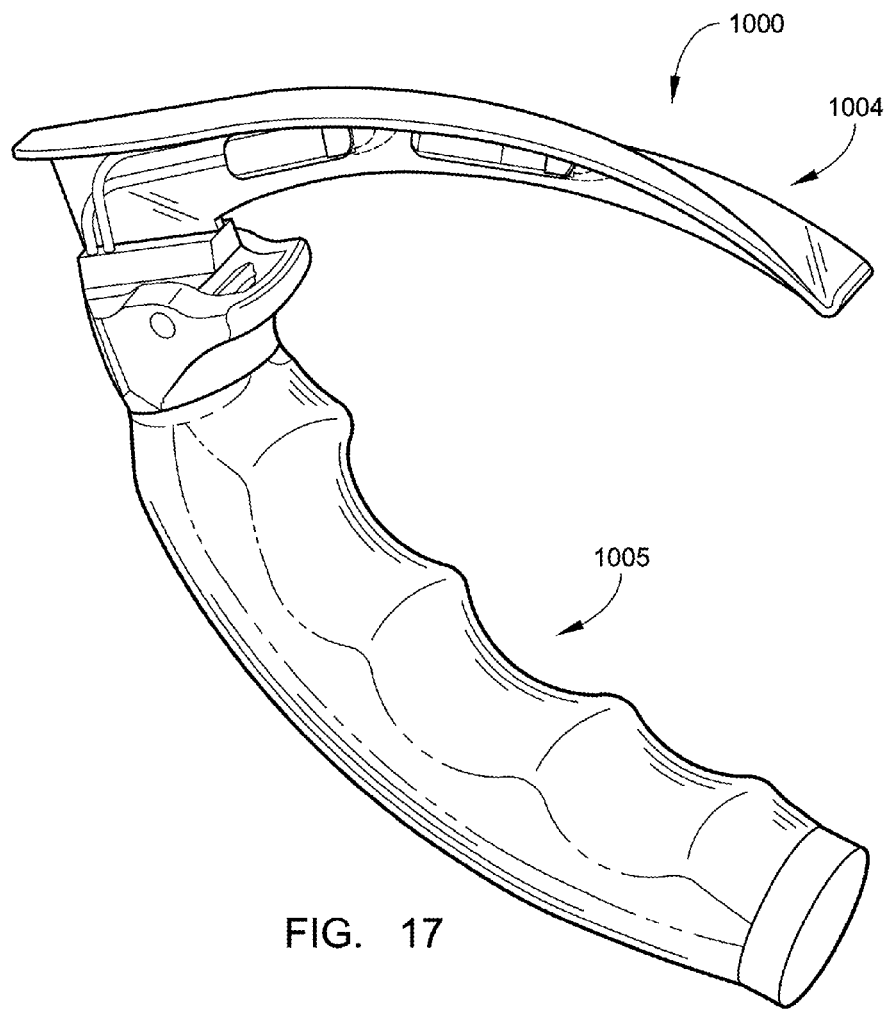
FIG. 17 is a perspective view of another embodiment of a laryngoscope.
Figure 18:
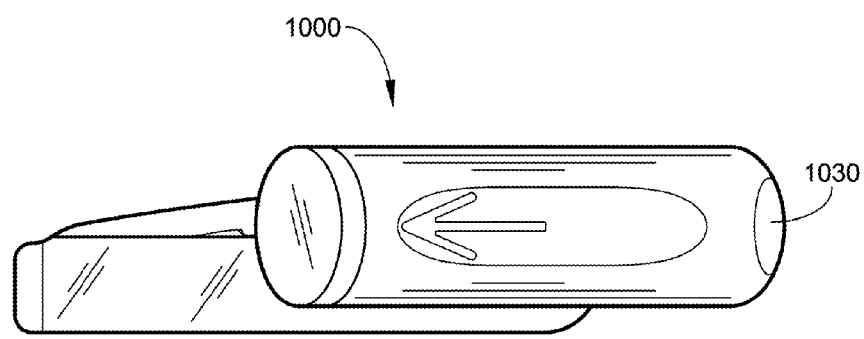
FIG. 18 is a bottom plan view of the laryngoscope illustrated in FIG. 17.
Figure 19:
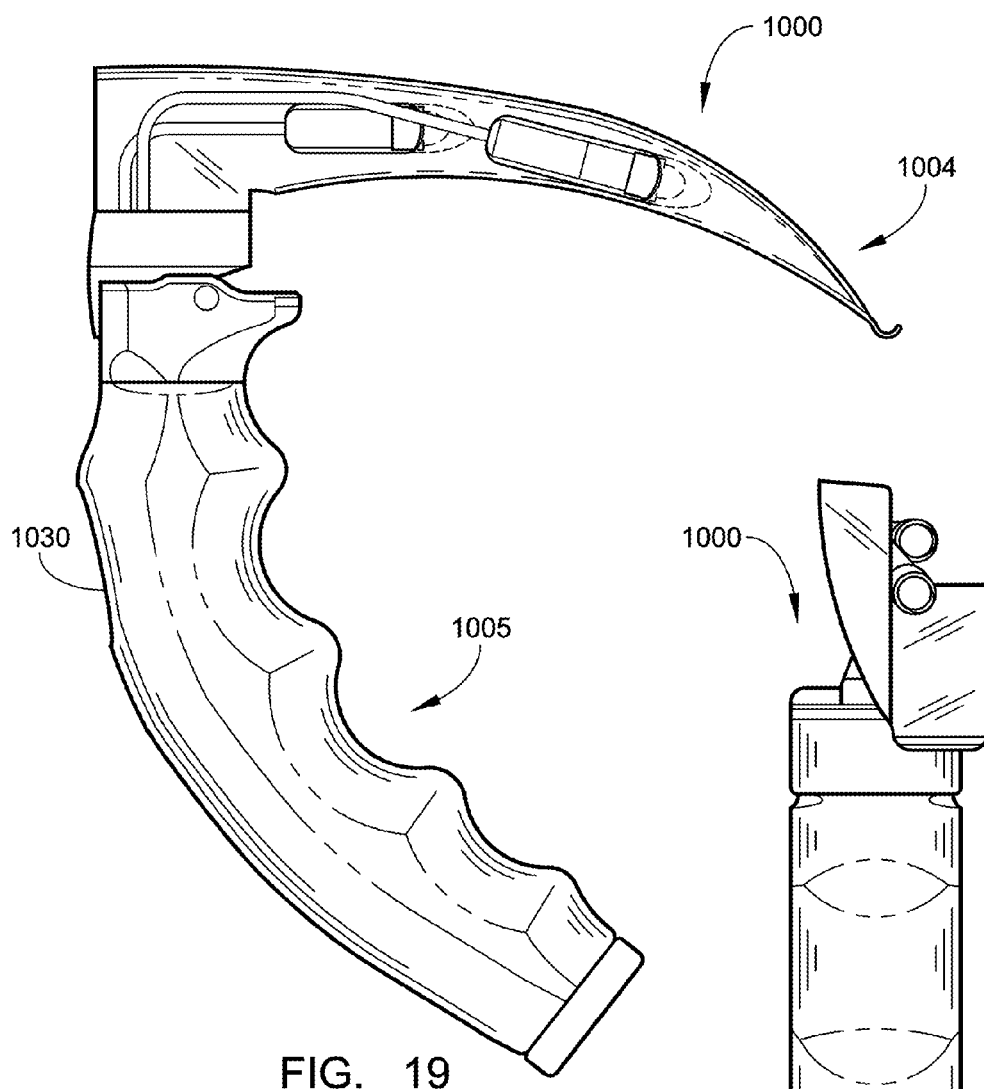
FIG. 19 is a front elevational view of the laryngoscope illustrated in FIG. 17.
Figure 20:
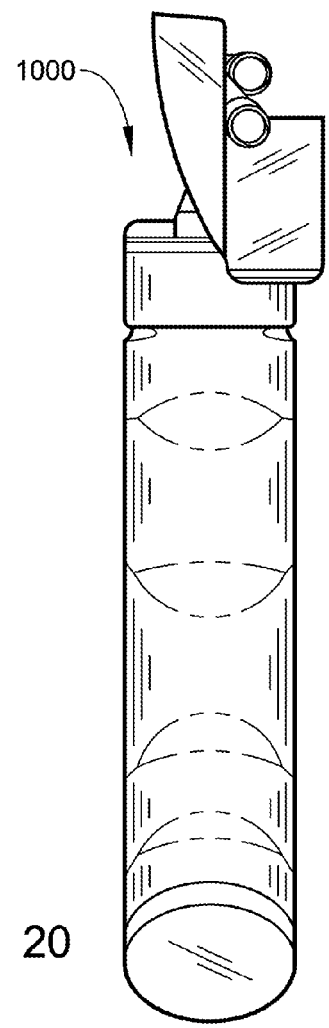
FIG. 20 is a right side elevational view of the laryngoscope illustrated in FIG. 17.

FIGS. 15 and 16 illustrate a modified laryngoscope 900 in which the handle 902 has an angled bend 904 at approximately the mid-point in its length, separating it into an upper, straight portion 905 and a lower straight portion 906 which is bent at an angle to the first/upper end portion. The angle between the upper portion 905 and lower portion 906 may be of the order of 40 to 60 degrees, for example 45 degrees. Apart from the handle being bent at an angle rather than continuously curved as in the embodiment of FIGS. 11 to 14, other parts of the laryngoscope of FIGS. 15 and 16 are identical to those of the previous embodiment, and like reference numerals are used for like parts as appropriate. As in the previous embodiment, the handle 902 has finger grip indents 806 and a blade stop 808 on its inner surface, facing the blade 804. The finger grip indents 822 allow the health care provider to grip the handle 902 more comfortably and securely, while the angled end portion allows the health care provider to position the blade 804 more efficiently during the procedure.

FIGS. 17-23 illustrate another embodiment of a laryngoscope 1000 that is generally similar to the laryngoscope 800 discussion above with respect to FIGS. 11-14, which is incorporated herein, but includes a distal black light source that is disposed 1.5 to 2.0 inches in front of a proximal white light source. In alternative embodiments, the distance between the distal black light source and the white light source is a distance other than 1.5 to 2.0 inches. Portions of the distal black light source and the proximal white light source are disposed through lateral holes in a curved vertical wall of laryngoscope blade (e.g., distal/bulb ends of black light source and white light source are disposed on one side of vertical wall and proximal ends of black light source and white light source are disposed on an opposite side of vertical wall). The laryngoscope 1000, and handle 1005, in particular, increases the effectiveness of blade insertion and placement through an improved ergonomic design. The laryngoscope 1000 and handle 1005 improve entry angle and handle control (to allow more effective tongue sweep and mandible lift). The laryngoscope 1000 and handle 1005 enable instinctive lift-direction to help avoid oral cavity damage. The laryngoscope 1000 limits "fulcruming" of blade/handle unit, which often leads to dental damage. In the past, the laryngoscopes used handle devices consisting of straight "flashlight-like" tubes that were non-ergonomic, difficult to control, and may promote use that can injure structures in the oral cavity.

The laryngoscope handle 1005 in FIGS. 17-23 is a four-finger-grip-indented handle 1005 made of machined aluminum and includes an ergonomic "pistol-grip" design that provides a proper angle for mandible lift and tongue sweep used in laryngoscopy, and provides ergonomical shape and design to prevent fulcruming and breaking teeth.

In the four-finger-grip-indented handle 1005 shown and described with respect to FIGS. 17-23, the laryngoscope is oriented in an opposite manner than that shown in FIG. 22 (i.e., second/lower end 1002 of handle 1005 oriented up and blade 1004 oriented down). A user grips handle 1005 by holding the handle 1005 in the palm of one's hand and presses one's thumb against the arrow 824 (FIGS. 19, 21, 22) in a first thumb location 1010, with the arrow 824 facing up (second/lower end 1002 oriented up) for proper orientation of the handle 100 during normal laryngoscopic use as shown in FIG. 1. The first thumb location 1010 is located in the elongate recessed region 822, near the first/upper end of handle 1005. In this position, the user's thumb is collinear with and longitudinally aligned with the elongated recessed region 822 and the handle 1005. The handle 1000 includes a second thumb location 1030 near a first/upper end 1032 of the laryngoscope handle 1005 that is engaged by the user's thumb during pediatric laryngoscopy. In this position, the user's thumb is substantially perpendicular with the handle 1005, giving the user a more delicate hold on the handle 1000 to help ensure that the child/toddler/baby is not injured during the pediatric laryngoscopy procedure.

In the laryngoscope orientation described above, the user wraps four fingers around and in four finger grip indents 1032, 1034, 1036, 1038. The user's index finger wraps around and in a first finger grip indent 1032 closest to second/lower end 1002 of handle 1005, the user's middle finger wraps around and in a second finger grip indent 1034 next closest to second/lower end 1002 of handle 1005, the third finger wraps around and in a third finger grip indent 1036 next closest to second/lower end 1002 of handle 1005, and the little finger wraps around and in a finger grip indent 1038 closest to first/upper end 1032 of handle 1005 (closest to where blade 1040 connects to the handle 1005). This design is an ergonomic design that provides a proper angle for mandible lift and tongue sweep used in adult laryngoscopy, and helps to ensure the right amount of torque/leverage in adult laryngoscopy to prevent fulcruming and breaking teeth.

With reference to laryngoscope handle 1045 shown in FIGS. 39A-39G, the description of the handles shown and described with respect to FIGS. 11-14 and 17-23 is incorporated herein. The laryngoscope handle 1045 is made of machined aluminum and includes an ergonomic "pistol-grip" design that provides a proper angle for mandible lift and tongue sweep used in pediatric laryngoscopy, and provides ergonomical shape and design to prevent fulcruming and breaking teeth. Although the laryngoscope handle 1045 shown in FIGS. 39A-39G is designed for pediatric laryngoscopy use, in alternative embodiments, the laryngoscope handle 1045 may be used for adult laryngoscopy. A main difference between the laryngoscope handle 1045 shown in FIGS. 39A-39G and the handles shown and described with respect to FIGS. 11-14 and 17-23 is that the laryngoscope handle 1045 shown in FIGS. 39A-39G includes a series of three finger grip indents on its inner, concave surface instead of a series of four finger grip indents 806 on its inner, concave surface (FIGS. 11-14 and 17-23).

Figure 39A:
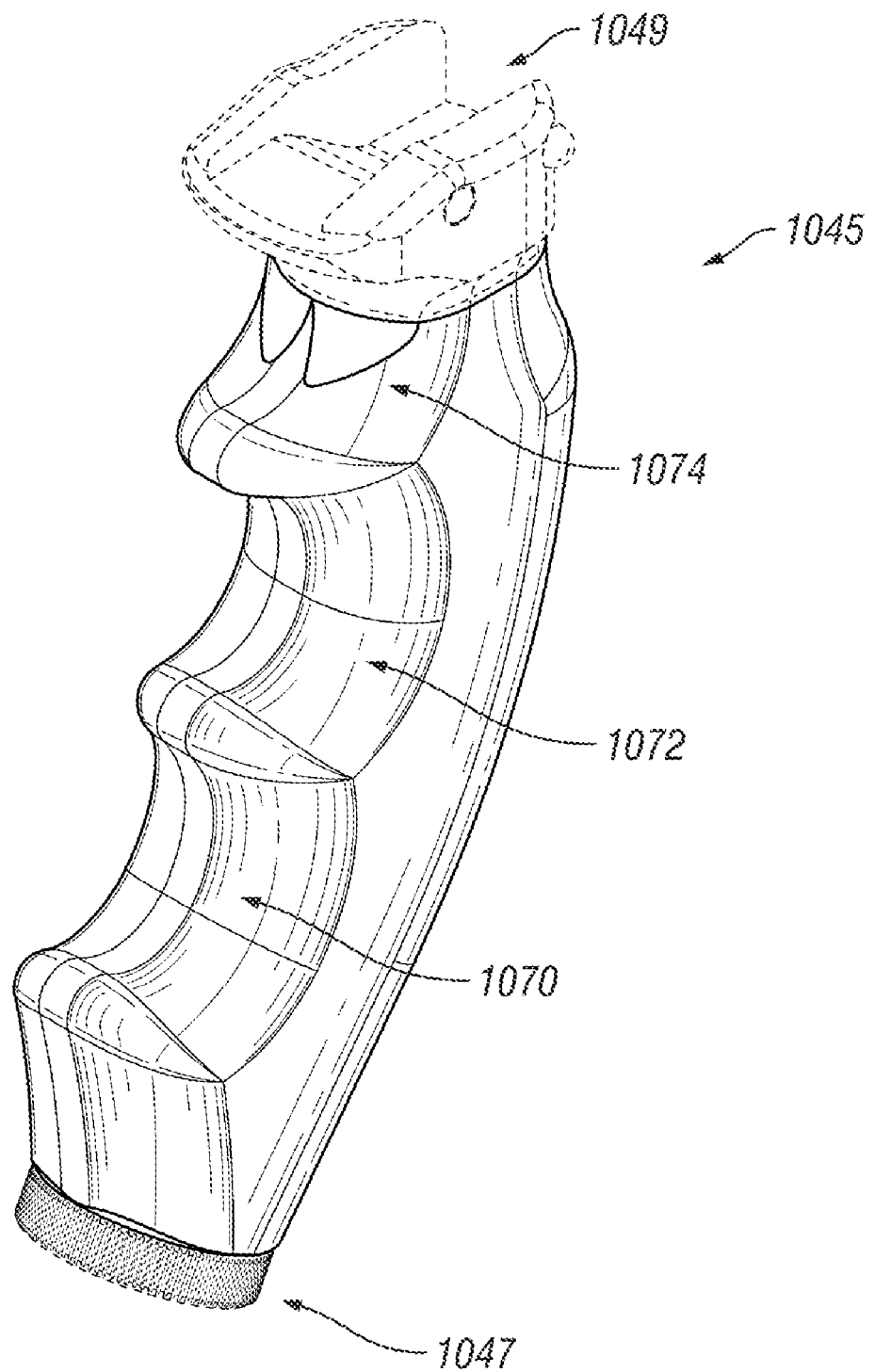
FIGS. 39A, 39B, 39C, 39D, 39E, 39F, 39G are perspective, left side elevational, right side elevational, rear elevational, front elevational, top plan, and bottom plan views of another embodiment of a laryngoscope handle.
Figure 39B:
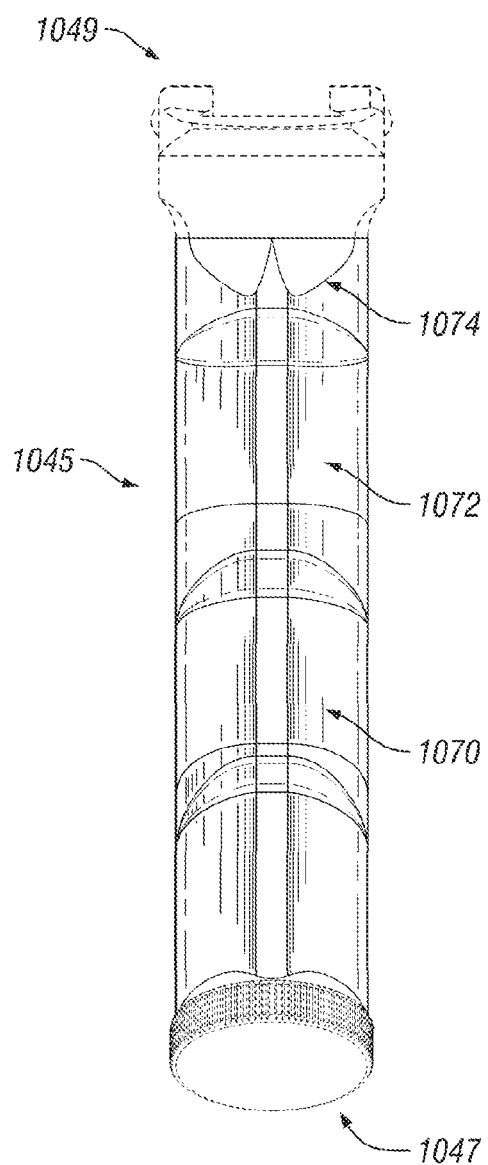
Figure 39C:
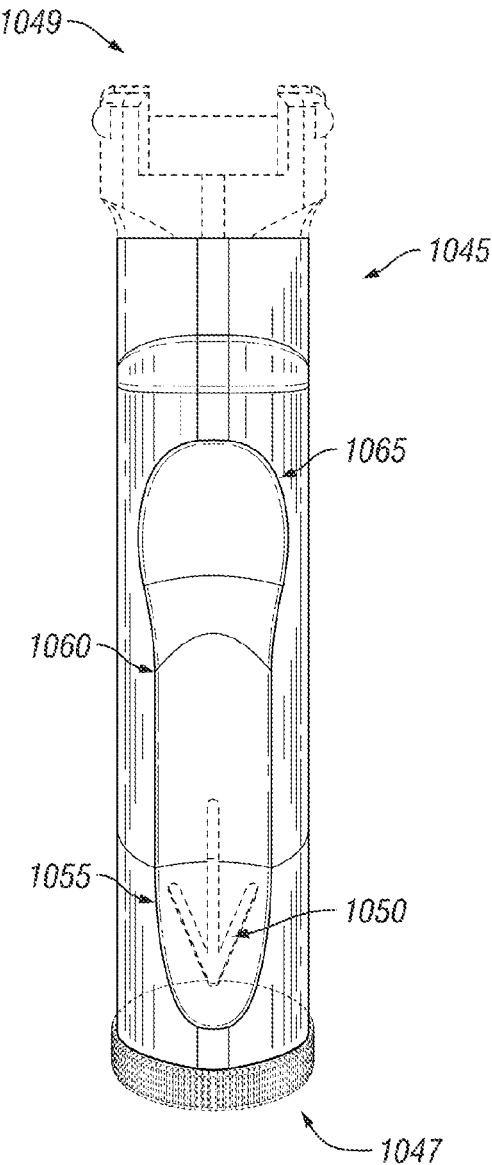
Figure 39D:
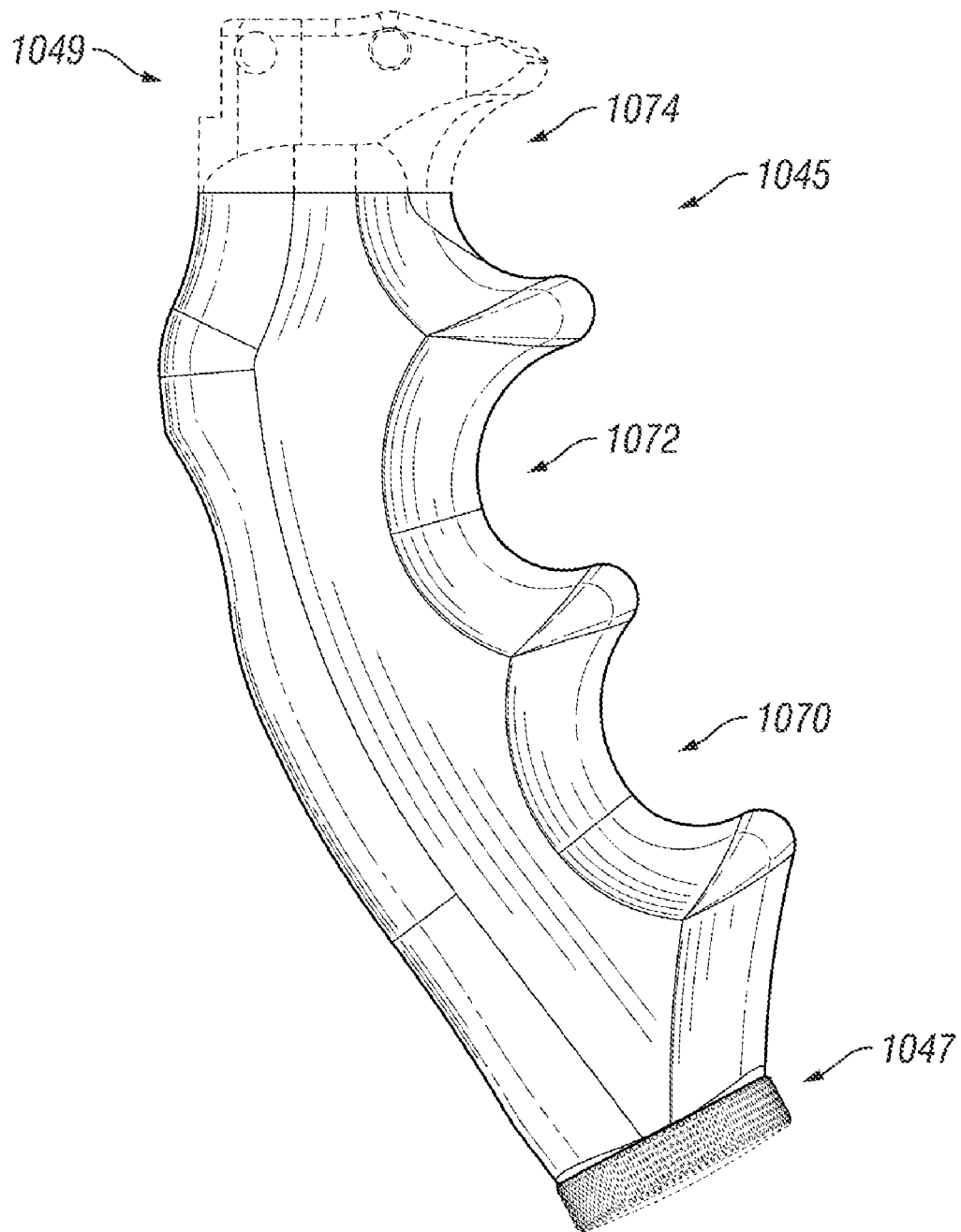
Figure 39E:
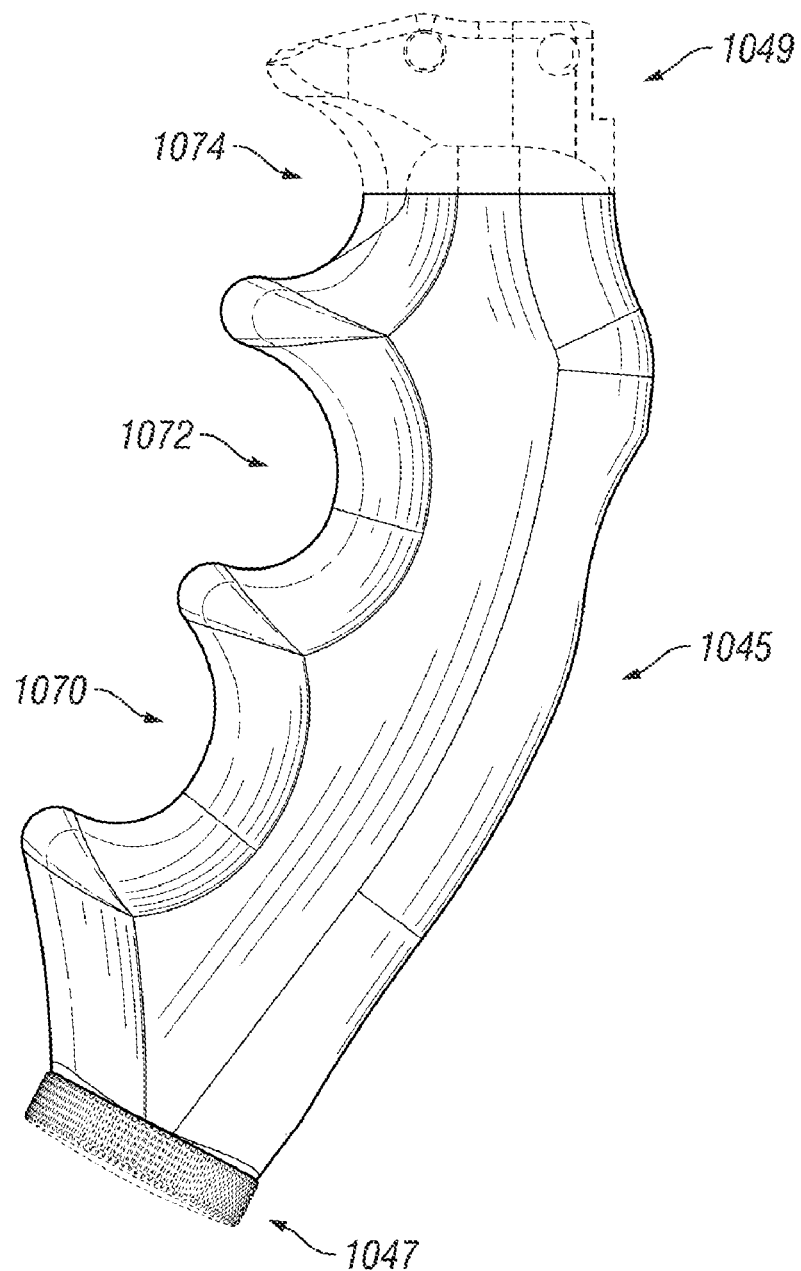
Figure 39F:
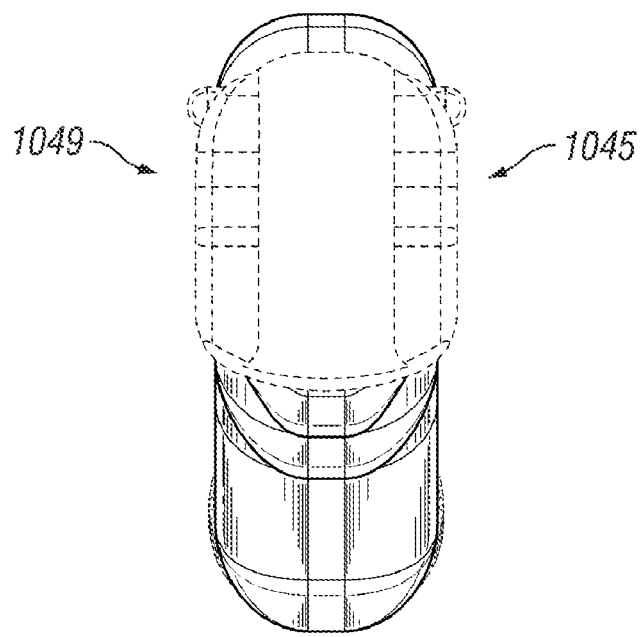
Figure 39G:
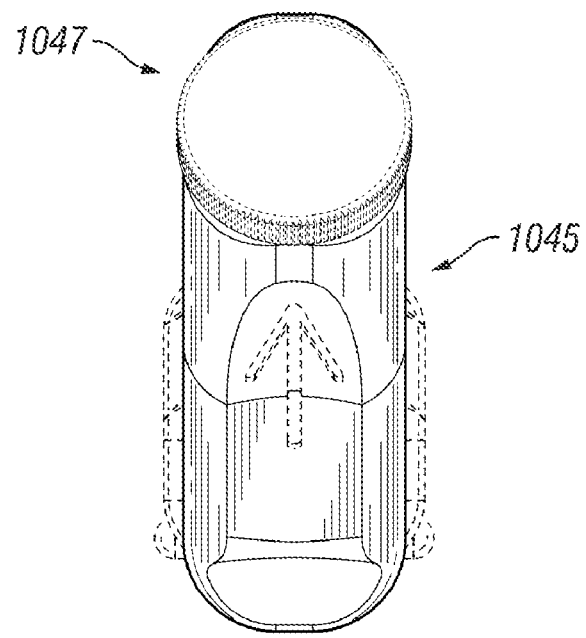
Figure 40B:
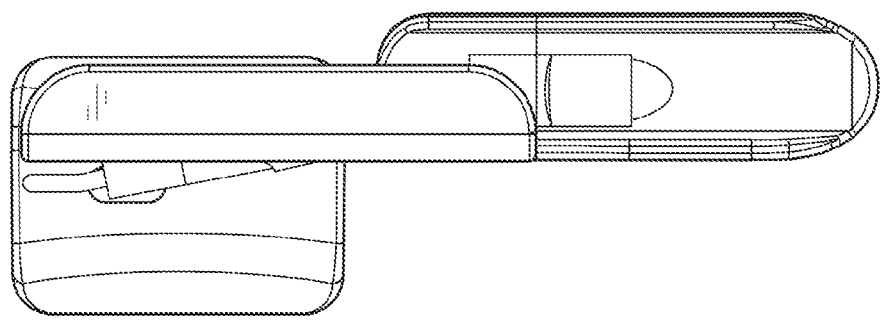
FIGS. 40A, 40B, 40C, 40D, 40E, and 40F are front elevational, top plan, rear elevational, bottom plan, right side elevational, and left side elevational views of another embodiment of a laryngoscope blade.
Figure 40A:
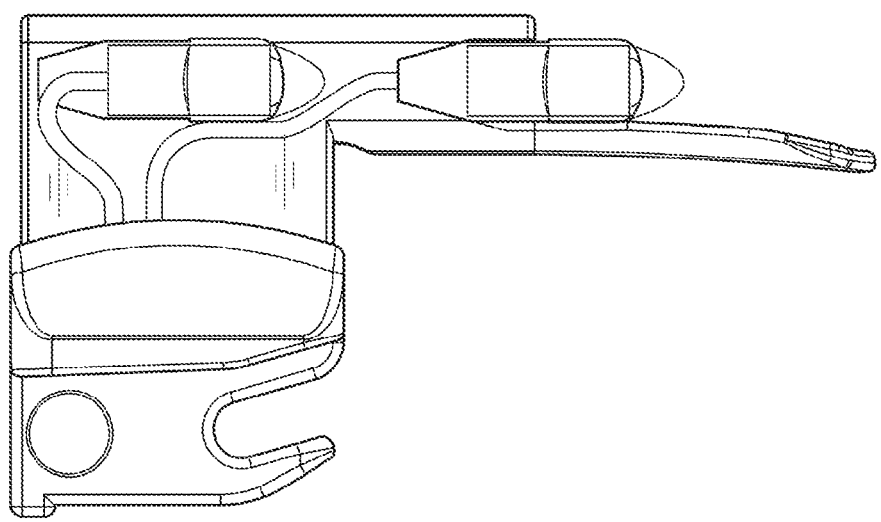
Figure 40D:
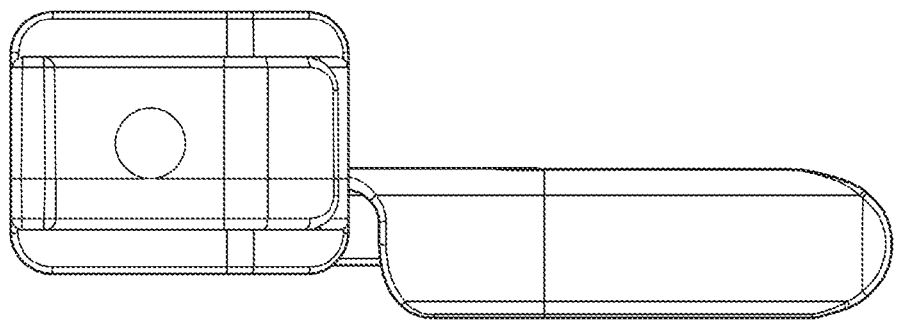
Figure 40C:
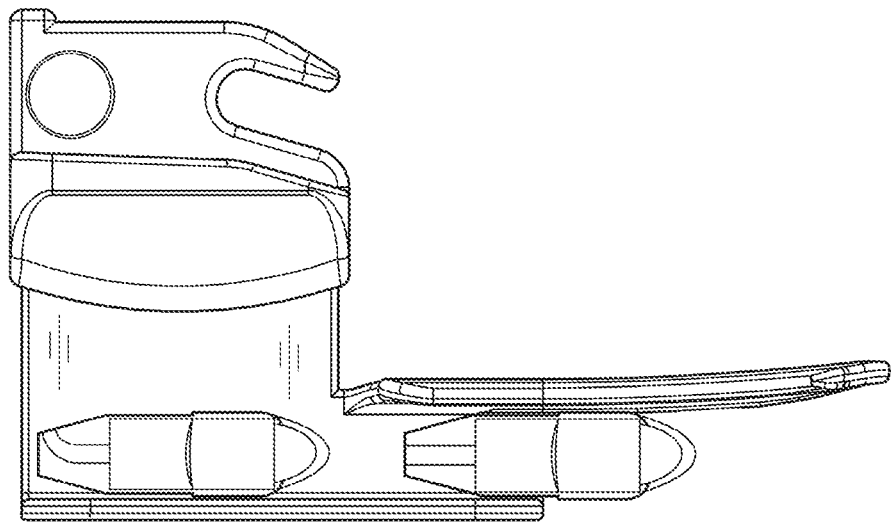
Figure 40E:
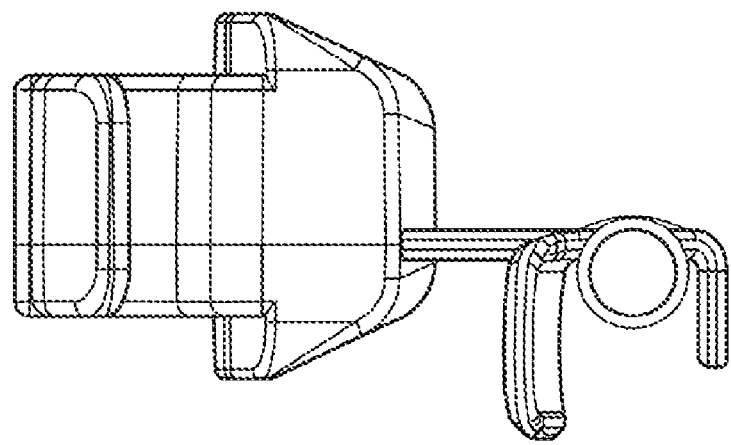
Figure 40F:
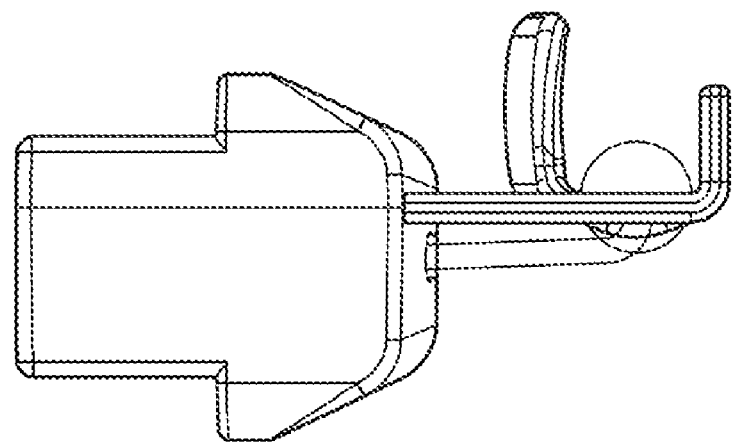
Figure 41A:
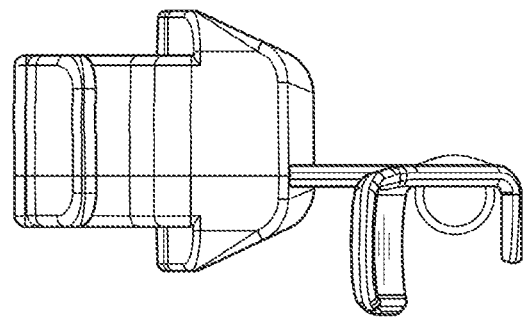
FIGS. 41A, 41B, 41C, 41D, 41E, and 41F are right side elevational, rear elevational, left side elevational, front elevational, bottom plan, and top plan views of an additional embodiment of a laryngoscope blade.
Figure 41B:
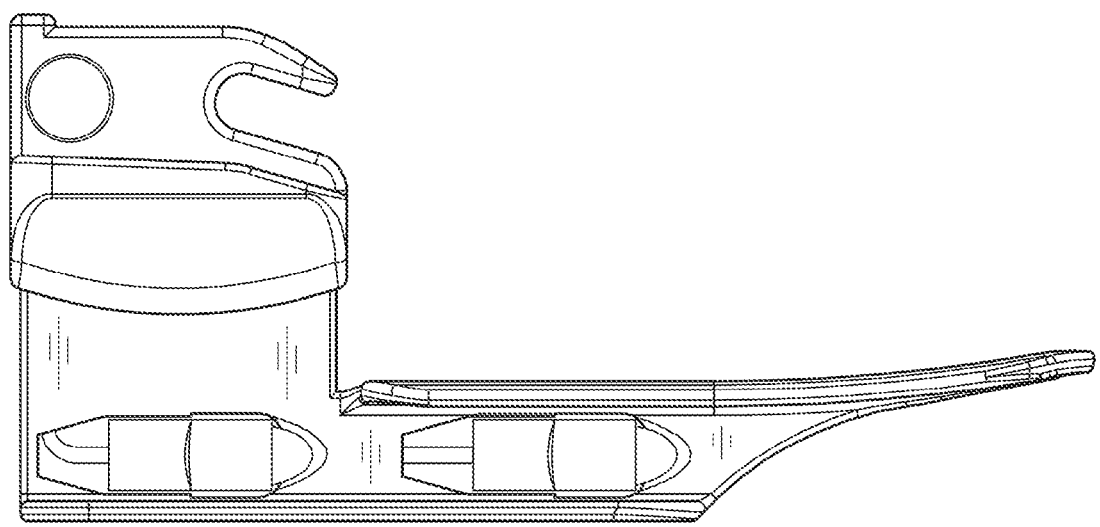
Figure 41C:
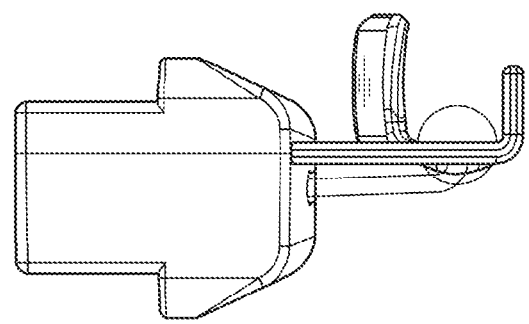
Figure 41D:
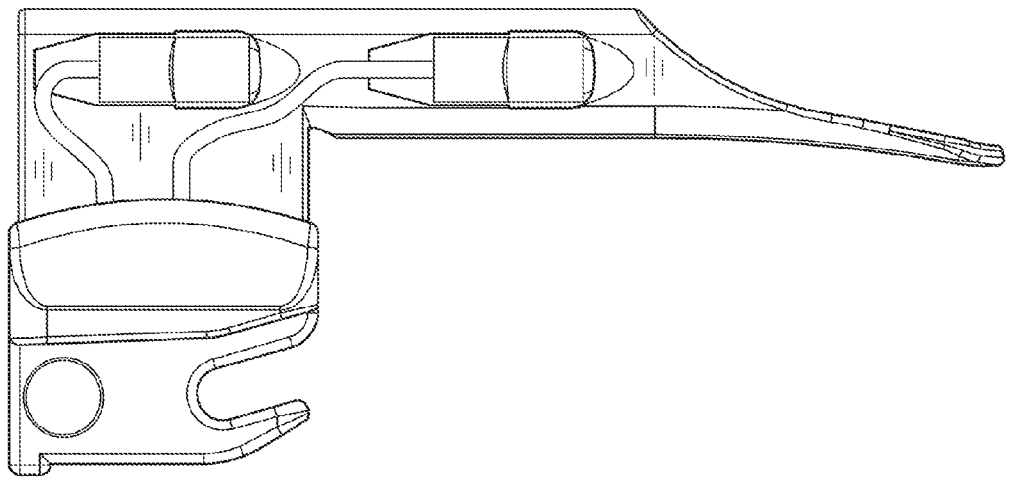
Figure 41E:
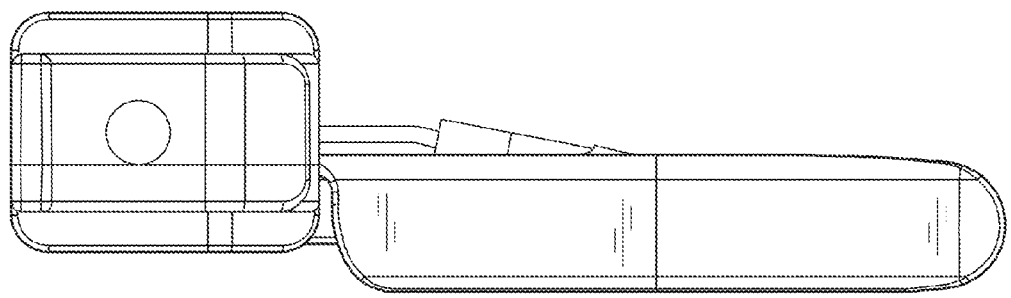
Figure 41F:
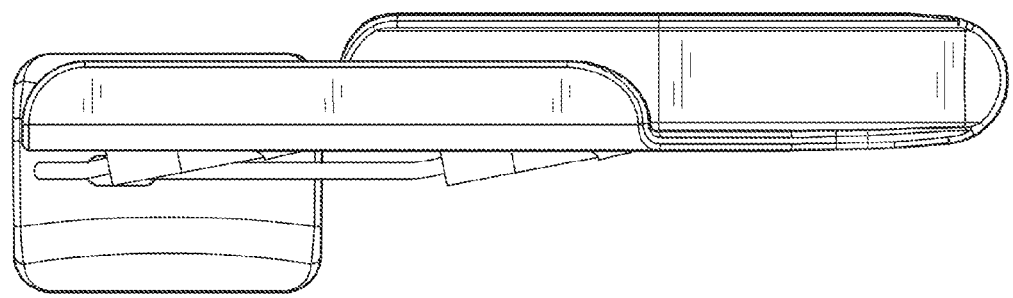
Figure 42A:
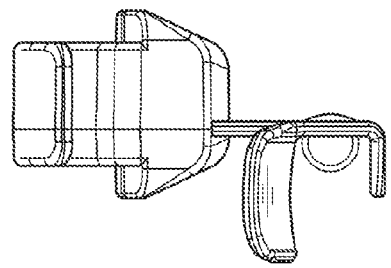
FIGS. 42A, 42B, 42C, 42D, 42E, 42F, and 42G are right side elevational, rear elevational, left side elevational, front elevational, bottom plan, perspective, and top plan views of a further embodiment of a laryngoscope blade.
Figure 42B:
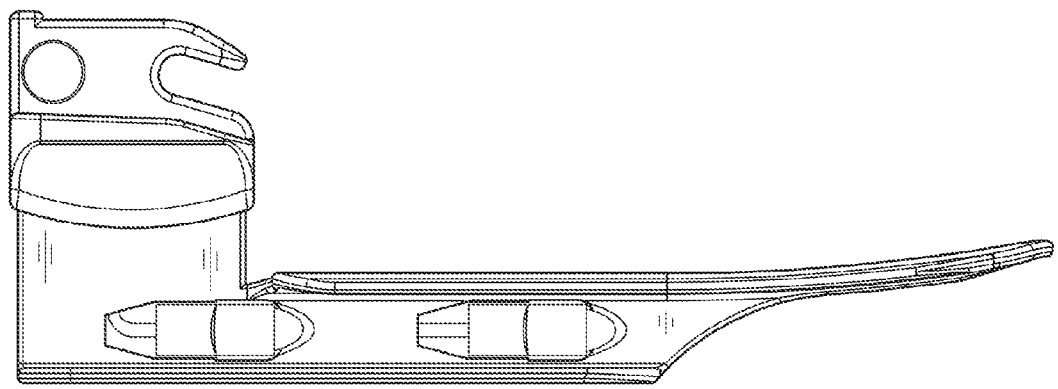
Figure 42C:
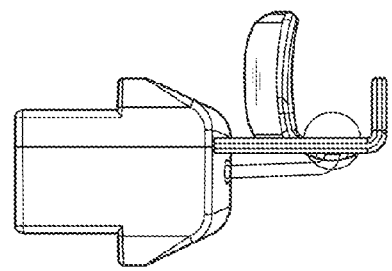
Figure 42D:
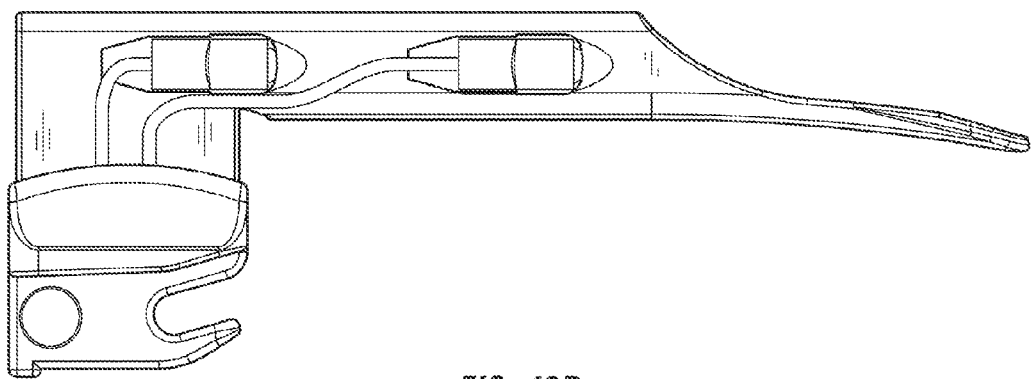
Figure 42E:
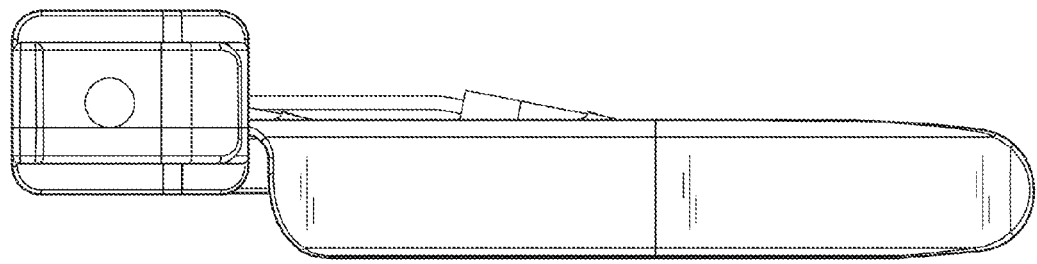
Figure 42F:
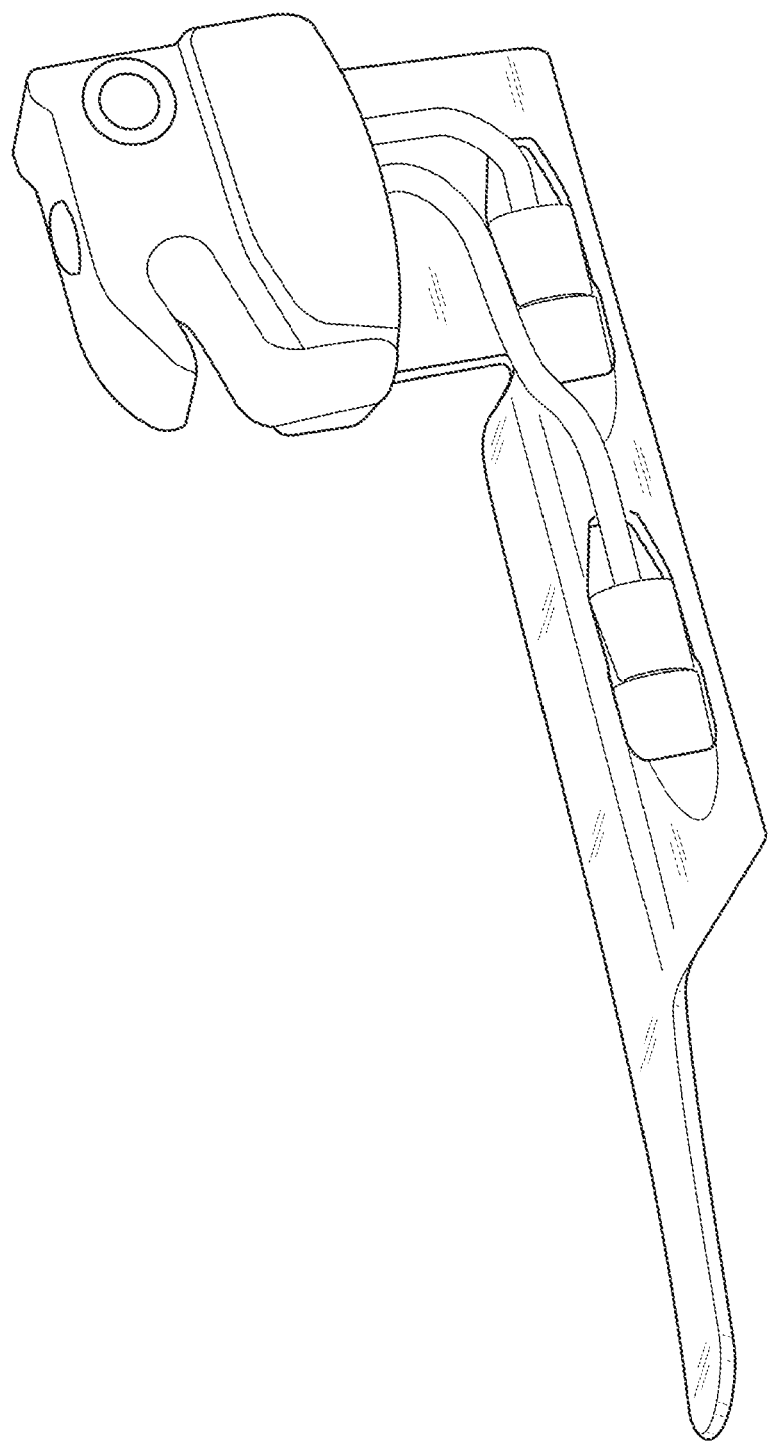
Figure 42G:
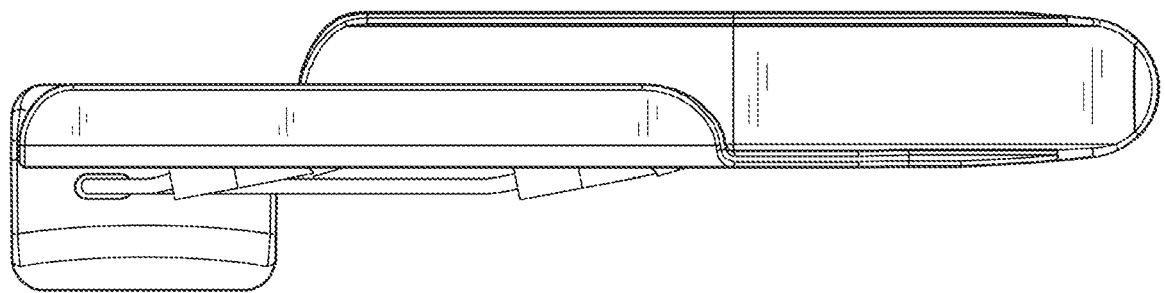
Figure 43A:
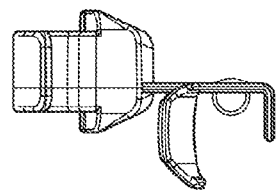
FIGS. 43A, 43B, 43C, 43D, 43E, and 43F are right side elevational, rear elevational, left side elevational, front elevational, bottom plan, and top plan views of a still further embodiment of a laryngoscope blade.
Figure 43B:
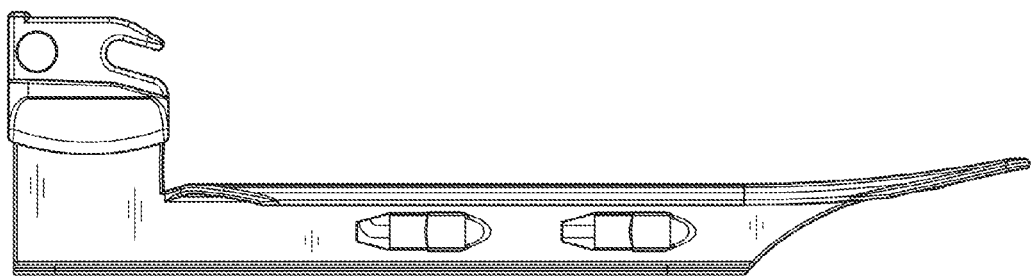
Figure 43C:
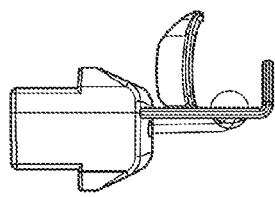
Figure 43D:
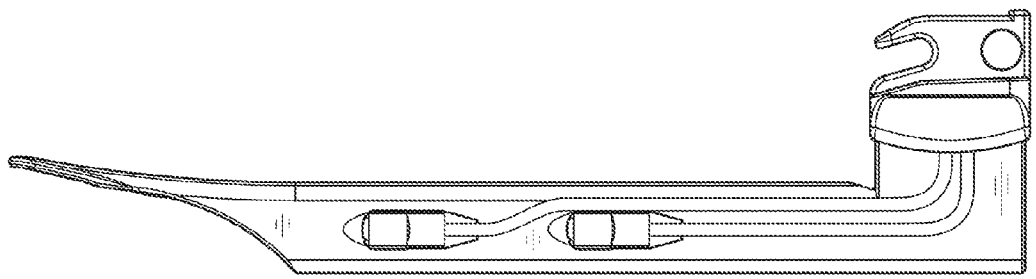
Figure 43E:
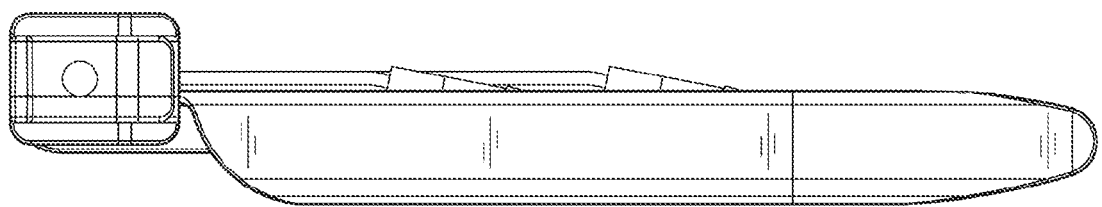
Figure 43F:
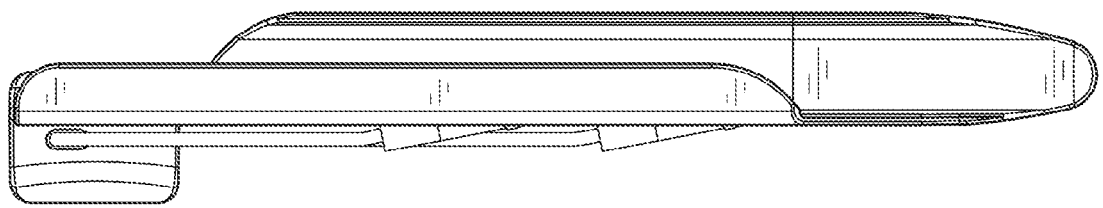
Figure 44D:
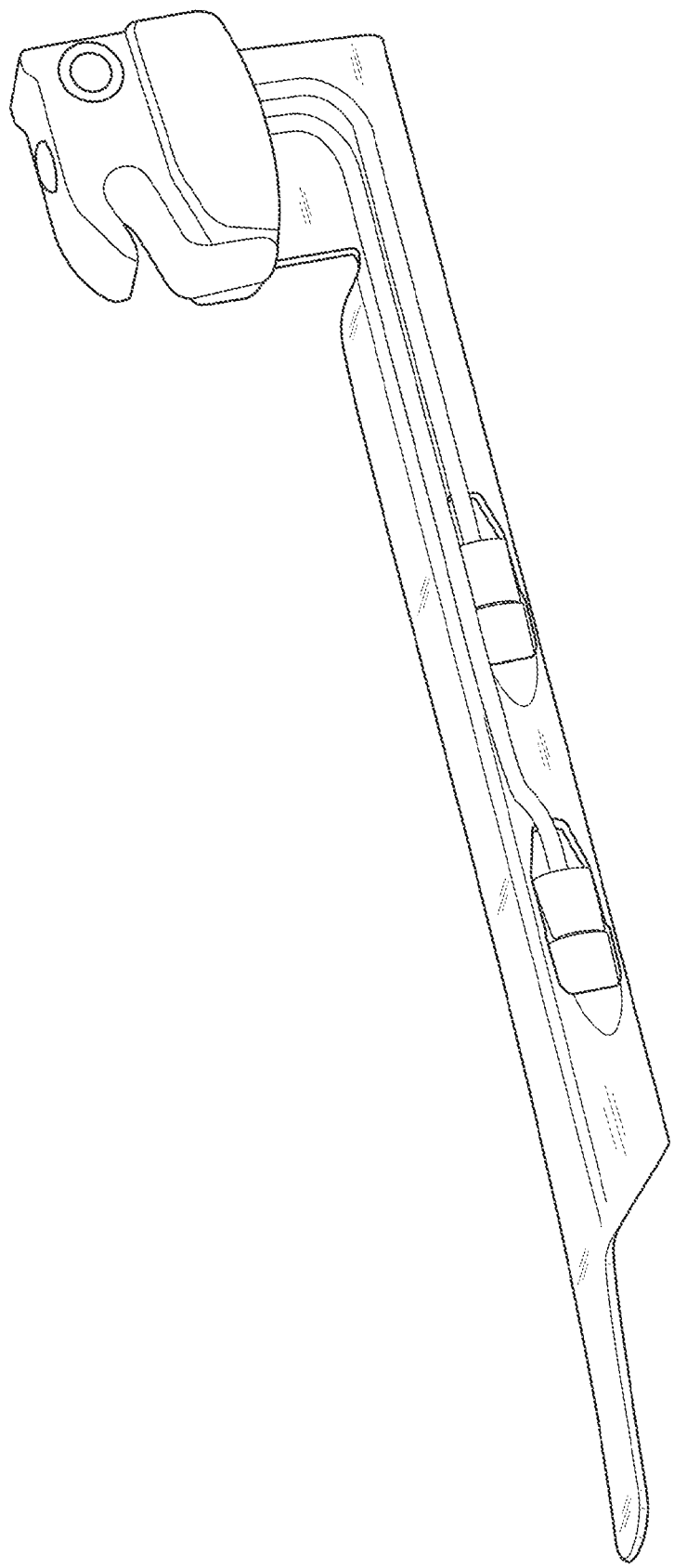
Figure 44E:
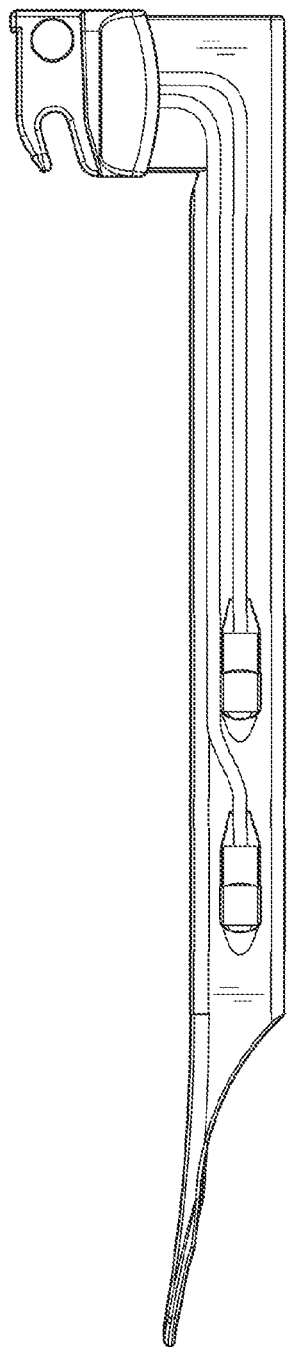
Figure 44F:
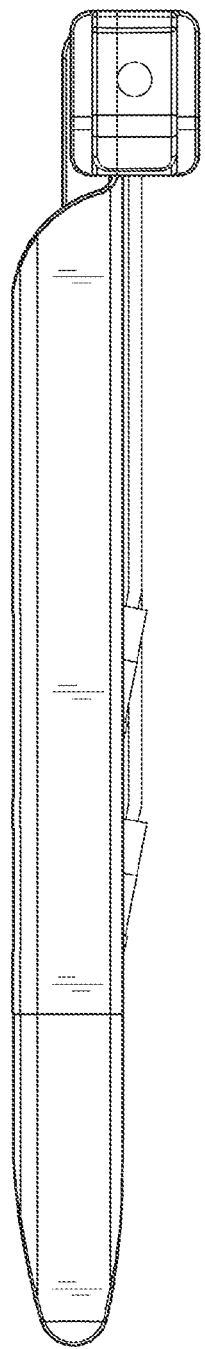
Figure 44G:
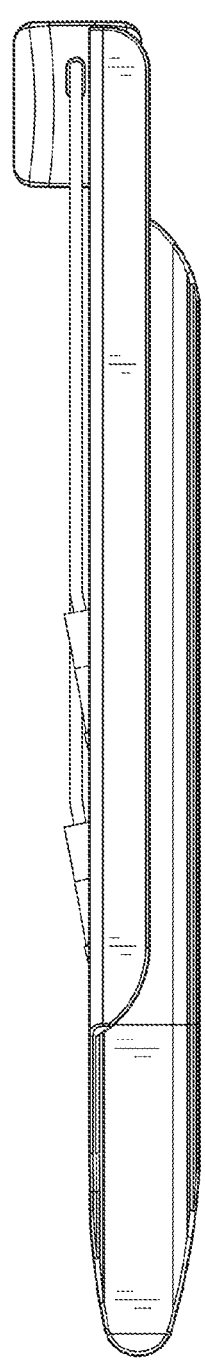
Figure 45D:
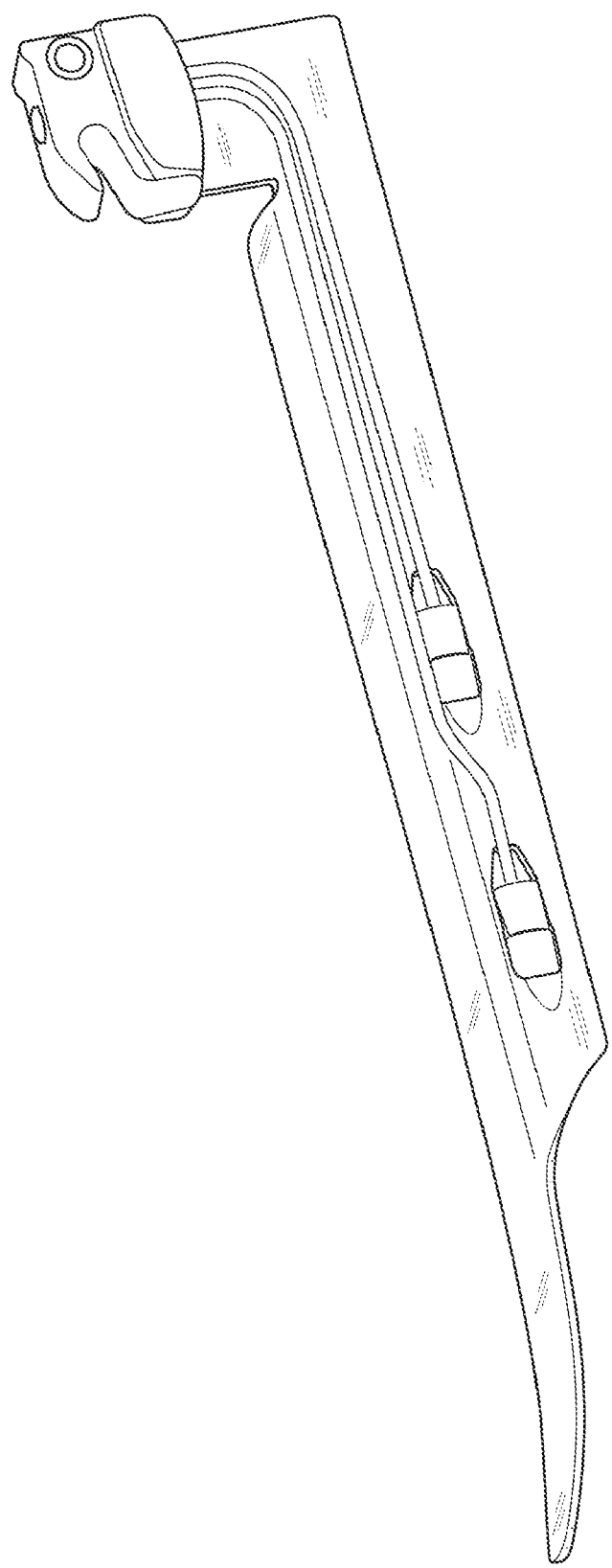
Figure 45E:
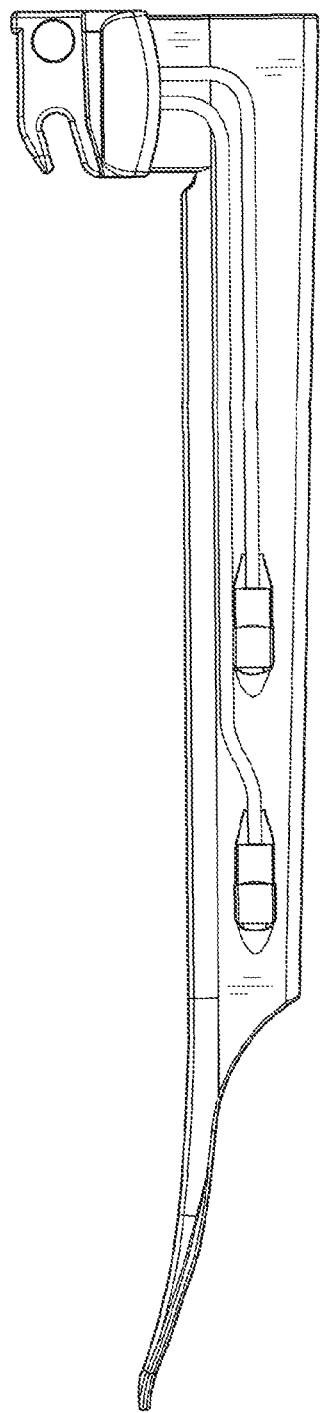
Figure 45F:
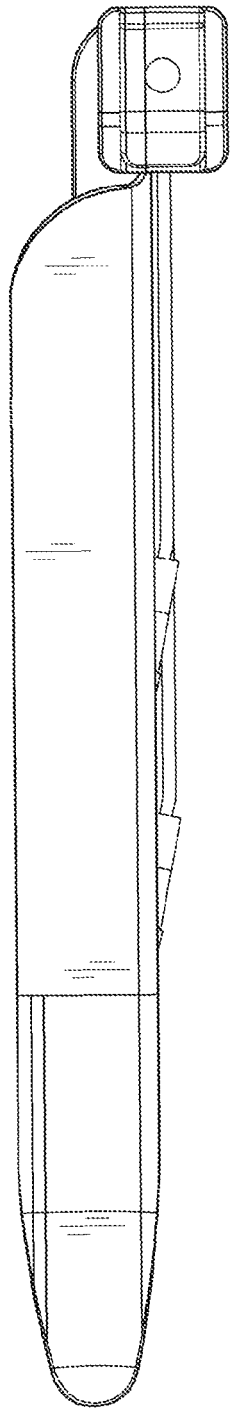
Figure 45G:
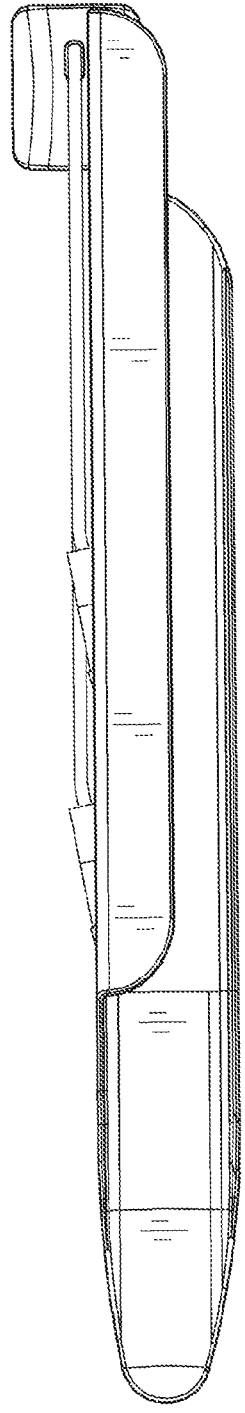
Figure 46A:
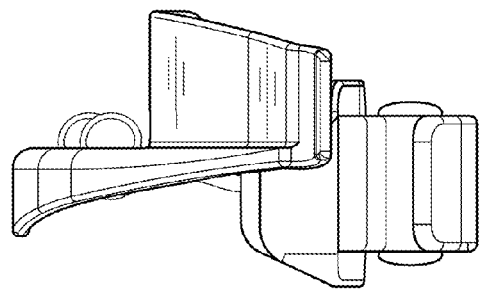
FIGS. 46A, 46B, 46C, 46D, 46E, and 46F are right side elevational, rear elevational, left side elevational, front elevational, bottom plan, and top plan views of a further embodiment of a laryngoscope blade.
Figure 46B:
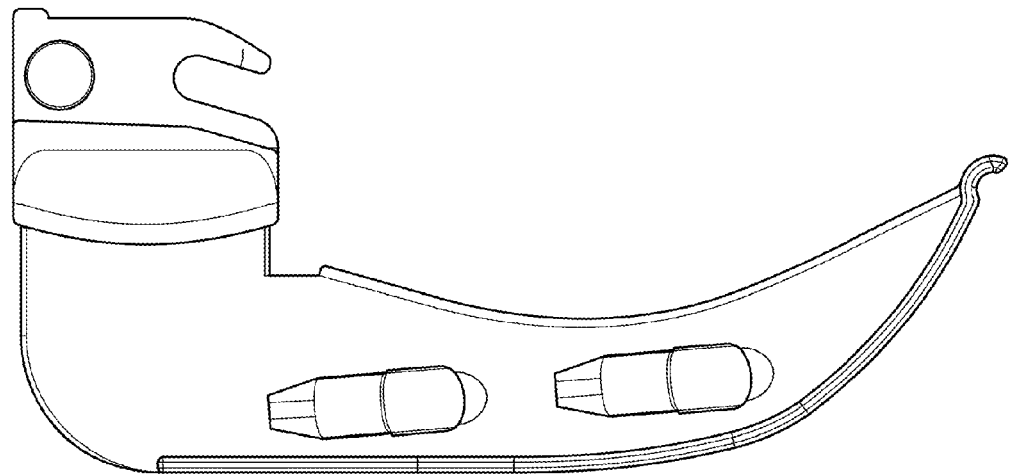
Figure 46C:
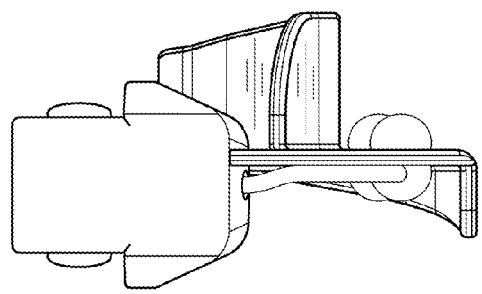
Figure 46D:
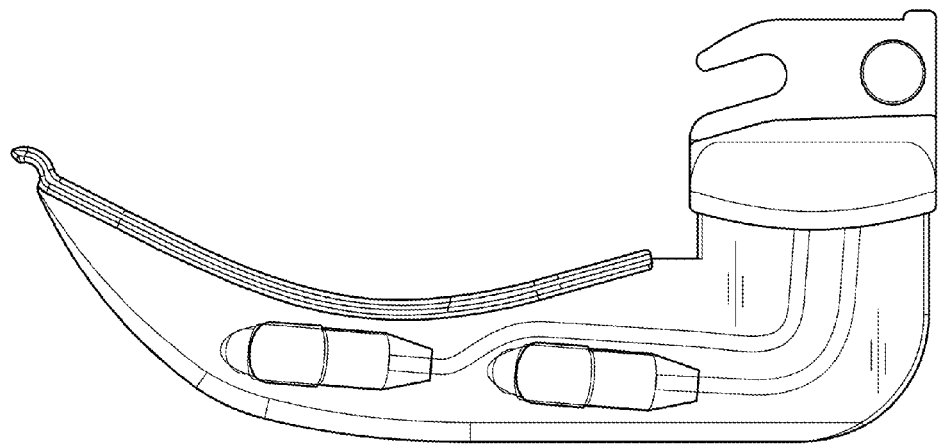
Figure 46E:
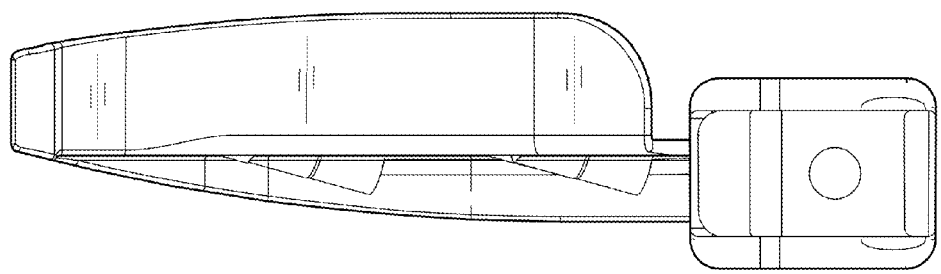
Figure 46F:
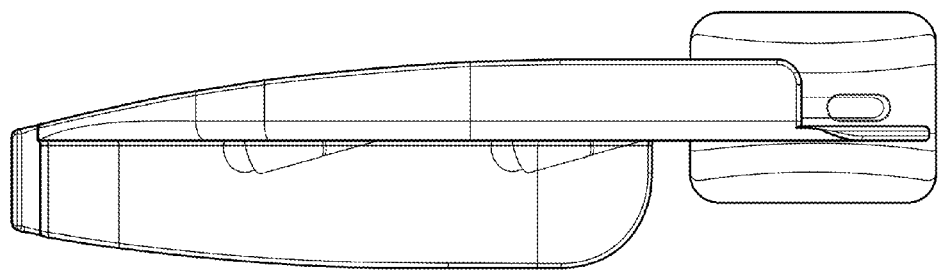
Figure 47A:
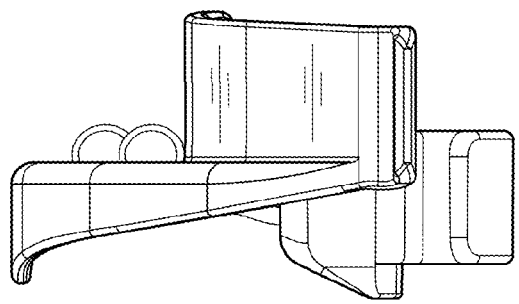
FIGS. 47A, 47B, 47C, 47D, 47E, and 47F are right side elevational, rear elevational, left side elevational, front elevational, bottom plan, and top plan views of a further embodiment of a laryngoscope blade.
Figure 47B:
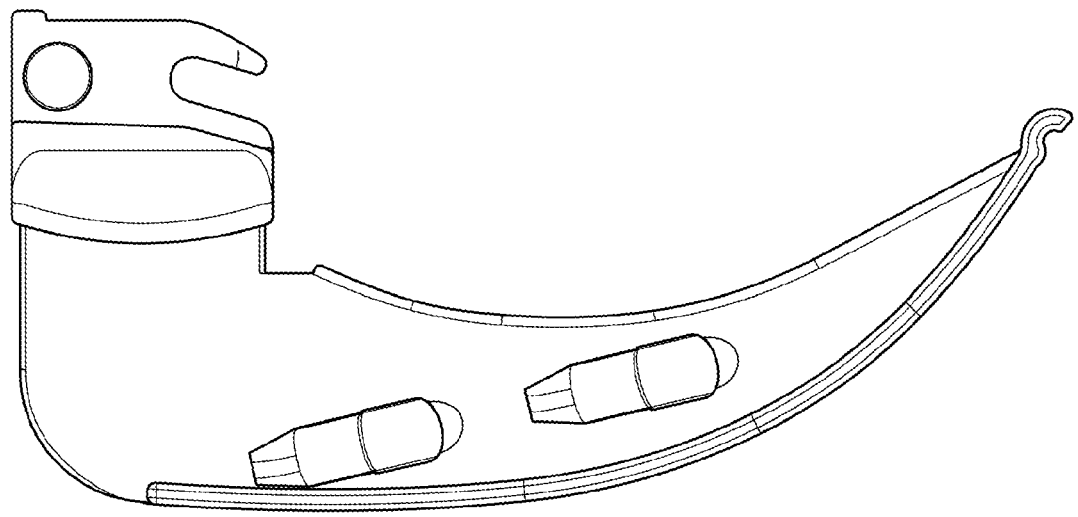
Figure 47C:
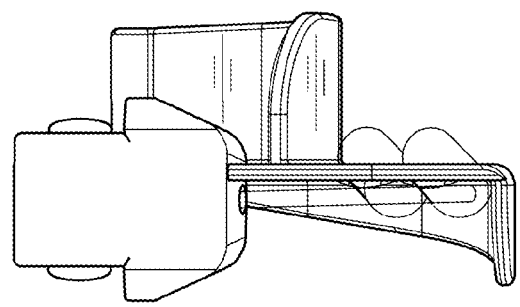
Figure 47D:
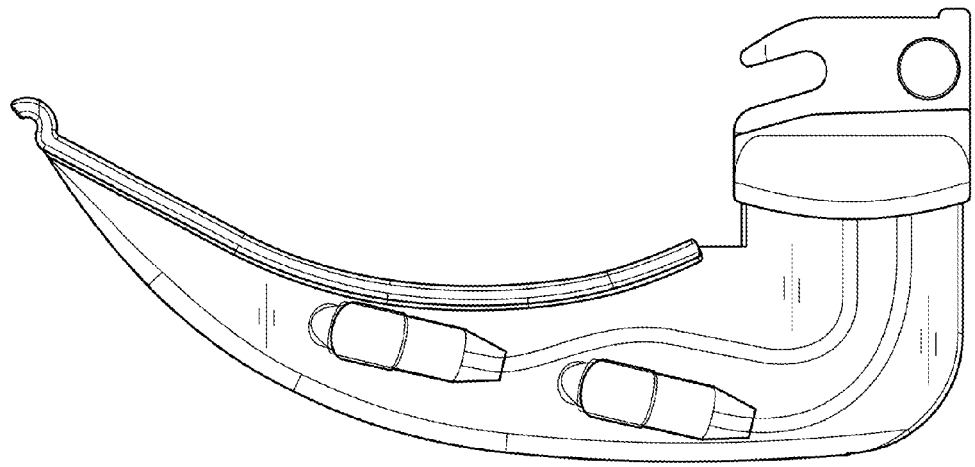
Figure 47E:
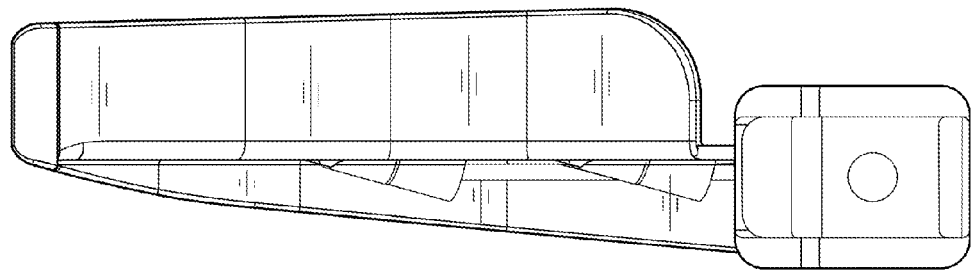
Figure 47F:
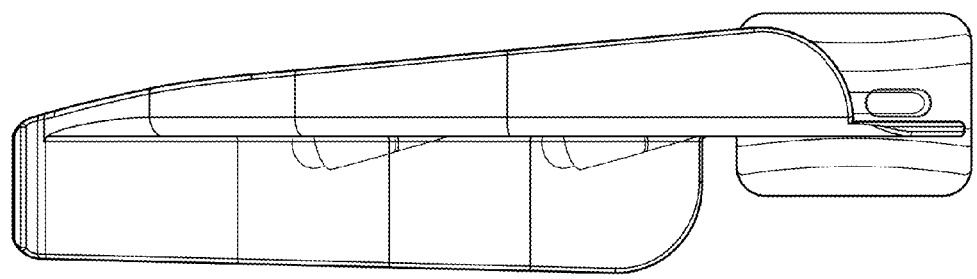
Figure 48A:
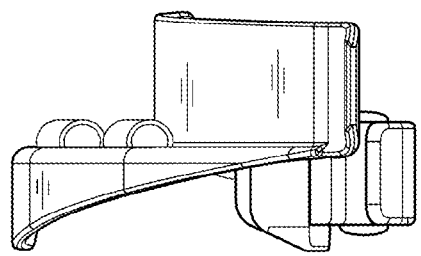
FIGS. 48A, 48B, 48C, 48D, 48E, and 48F are right side elevational, rear elevational, left side elevational, front elevational, bottom plan, and top plan views of a still further embodiment of a laryngoscope blade.
Figure 48B:
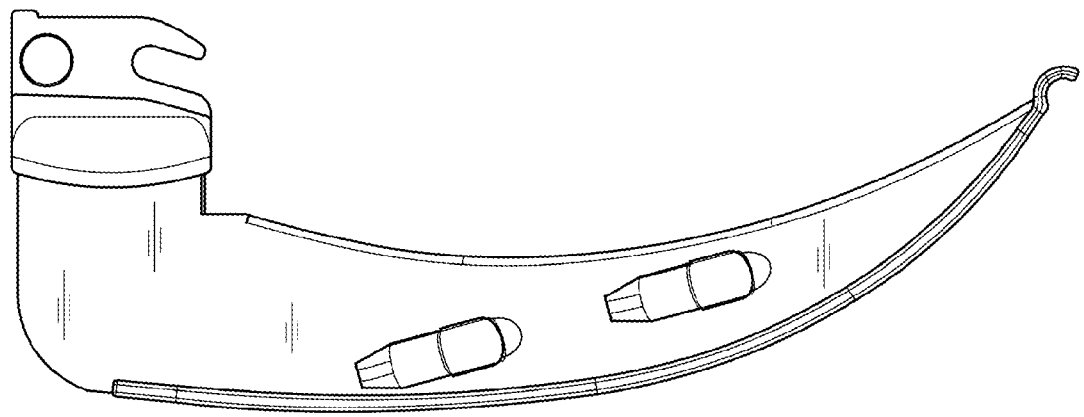
Figure 48C:
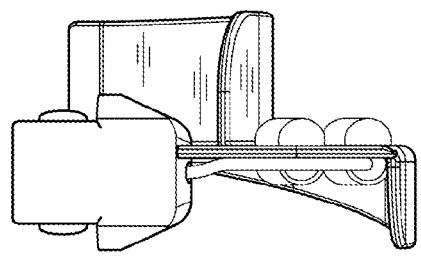
Figure 48D:
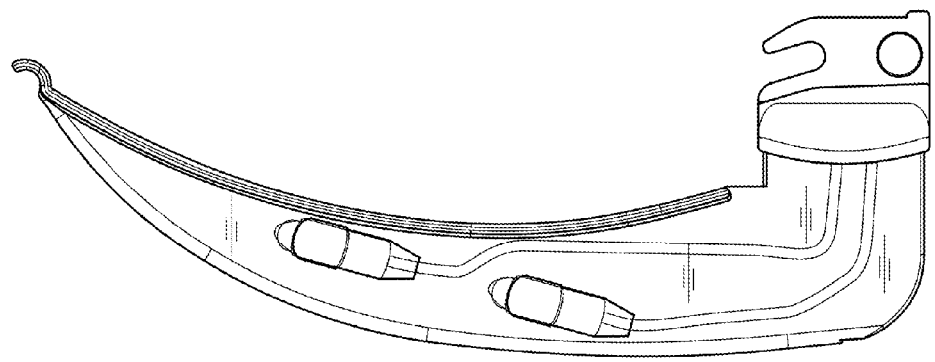
Figure 48E:
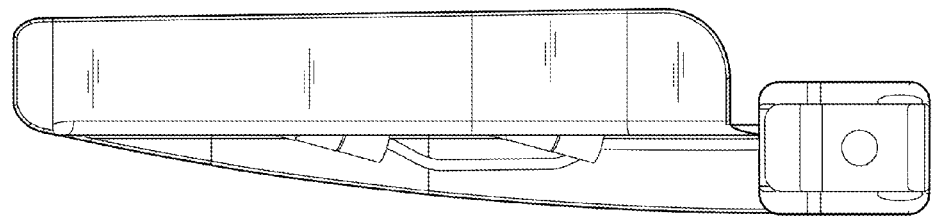
Figure 48F:
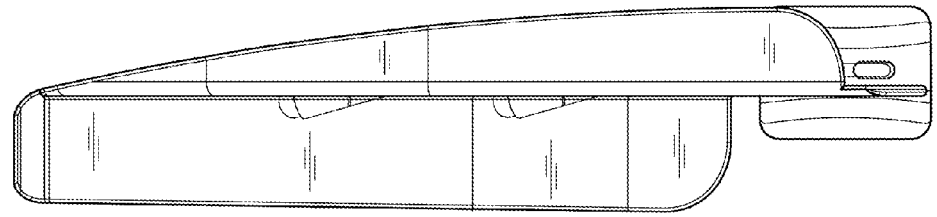
Figure 49A:
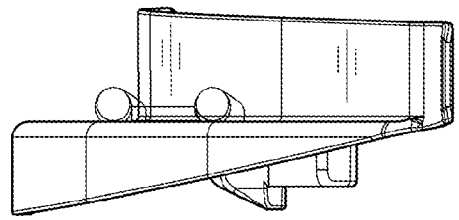
Figure 49B:
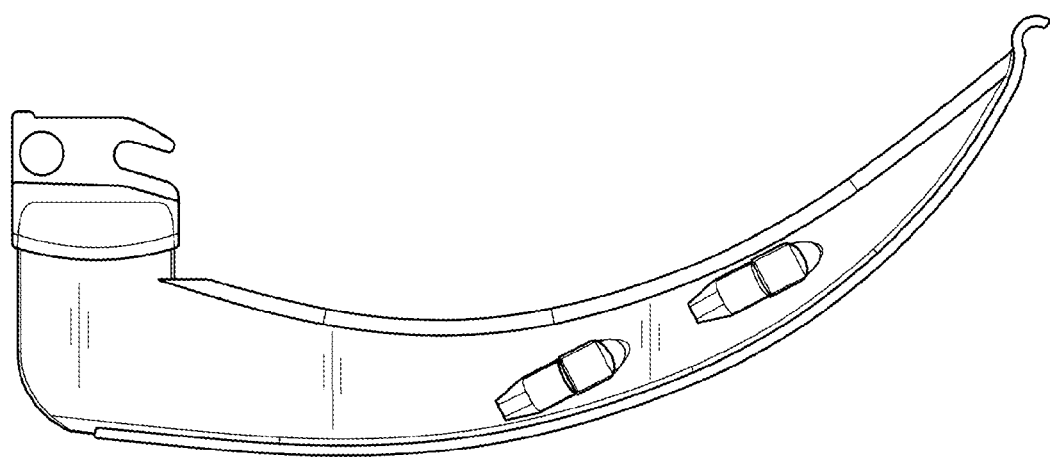
Figure 49C:
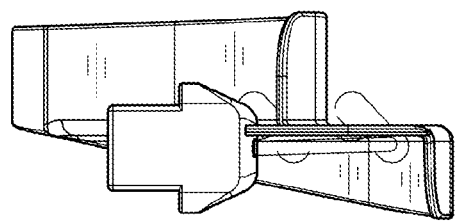
Figure 49D:
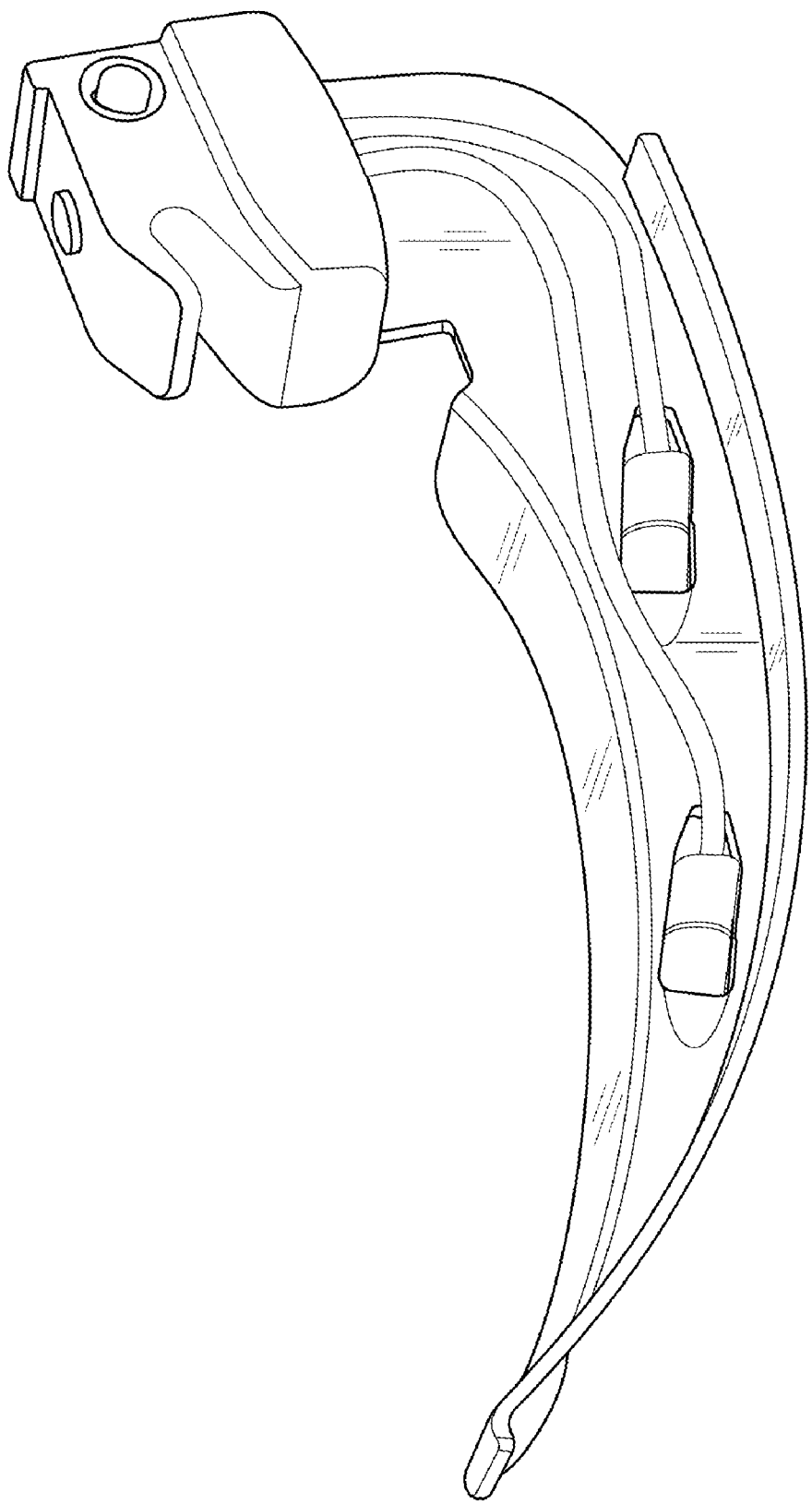
Figure 49E:
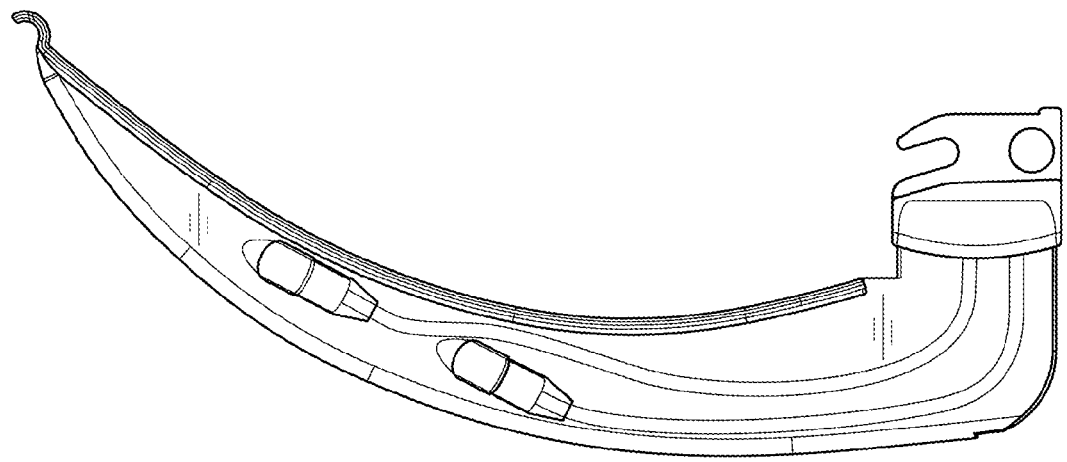
Figure 49F:
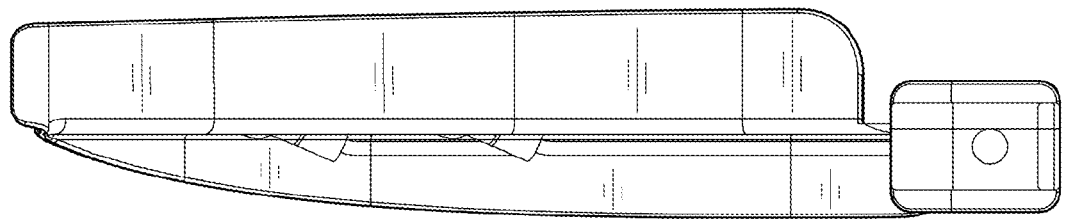
Figure 49G:
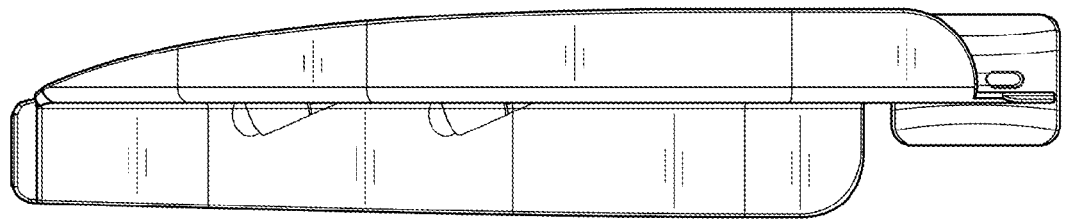

In the three-finger-grip-indented handle 1045 shown with respect to FIGS. 39A-39G, the laryngoscope/handle 1045 is oriented in an opposite manner than that shown in FIG. 39A (i.e., second/lower end 1047 of handle 1045 oriented up and first/upper end 1049 of handle 1045 oriented down). A user grips handle 1045 by holding the handle 1045 in the palm of one's hand and presses one's thumb against arrow 1050 (with second/lower end 1047/arrow 1050 facing up) for proper orientation of the handle 1045 during normal laryngoscopic use as shown in FIG. 1. The first thumb location 1055 is located in elongate recessed region 1060, near second/lower end 1047 of handle 1045. In this position, the user's thumb is collinear with and longitudinally aligned with the elongated recessed region 1060 and the handle 1045. The handle 1045 includes a second thumb location 1065 at an opposite end of the elongate recessed region 1060, near a first/upper end 1049 of the laryngoscope handle 1045, which is engaged by the user's thumb during more-delicate pediatric laryngoscopy. In this position, the user's thumb is substantially perpendicular with the handle 1045, giving the user a more delicate hold on the handle 1045 to help ensure that the child/toddler/baby is not injured during this more-delicate pediatric laryngoscopy procedure.

In the first laryngoscope orientation, the user wraps three fingers (one's middle finger, third finger, and little finger) around and in three finger grip indents 1070, 1072, 1074. The middle finger wraps around and in a first finger grip indent 1070 closest to second/lower end 1047 of handle 1045, the third finger wraps around and in a second middle finger grip indent 1072 next closest to second/lower end 1047 of handle 1045, and the little finger wraps around and in a third finger grip indent 1074 closest to first/upper end 1049 of handle 1045 (closest to where the blade connects to the handle 1045). Because the user only grips the handle 1045 with three fingers (compared to gripping the handle 1005 of FIGS. 17-23 with four fingers), the user has a more delicate hold/grip on the handle 1045 and automatically provides less torque/leverage, which is appropriate for pediatric use. Thus, the handle 1045 shown in FIGS. 39A-39G includes an ergonomic design that provides a proper angle for mandible lift and tongue sweep used in pediatric laryngoscopy, and helps to ensure the right amount of torque/leverage in child laryngoscopy to prevent fulcruming and breaking teeth.

Figure 24:
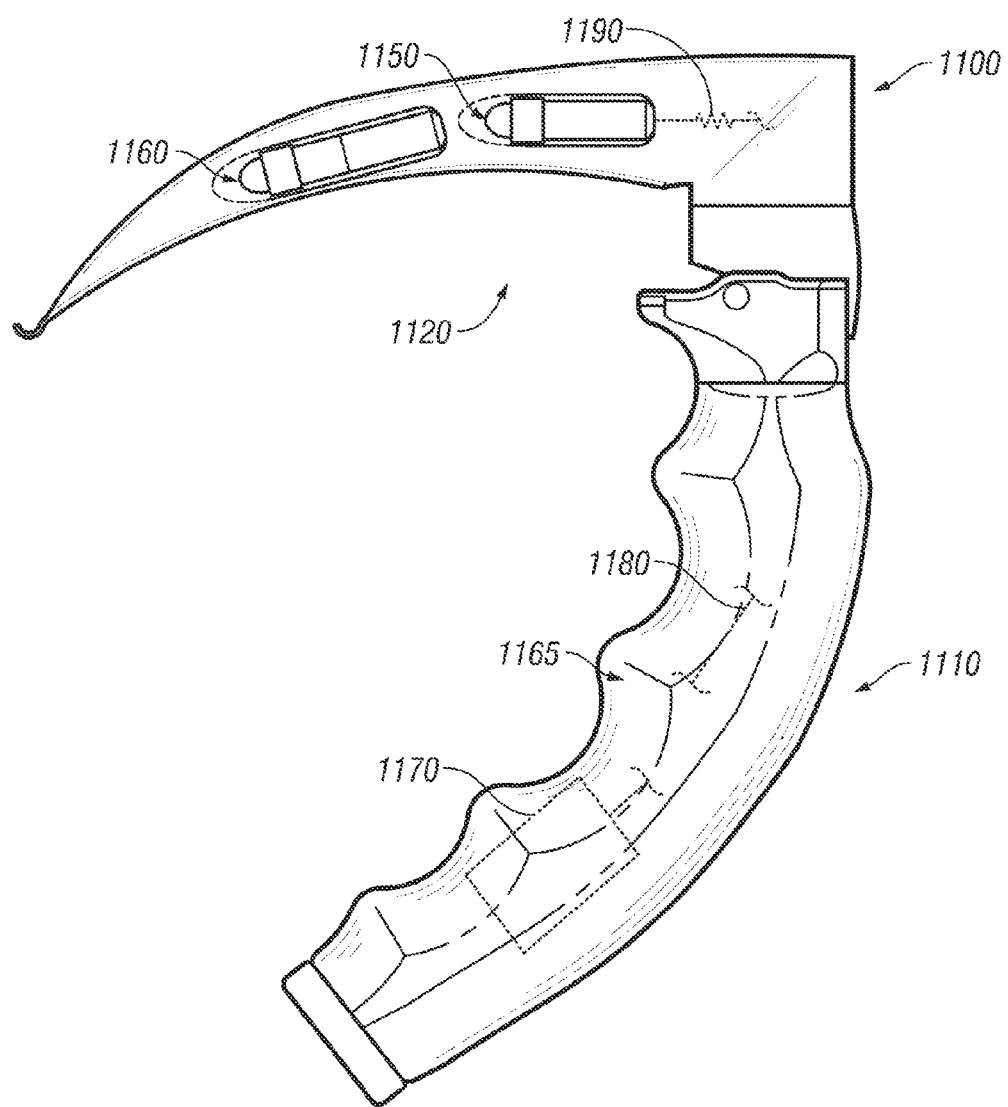
FIG. 24 is a front elevational view of another embodiment of a laryngoscope.
Figure 25:
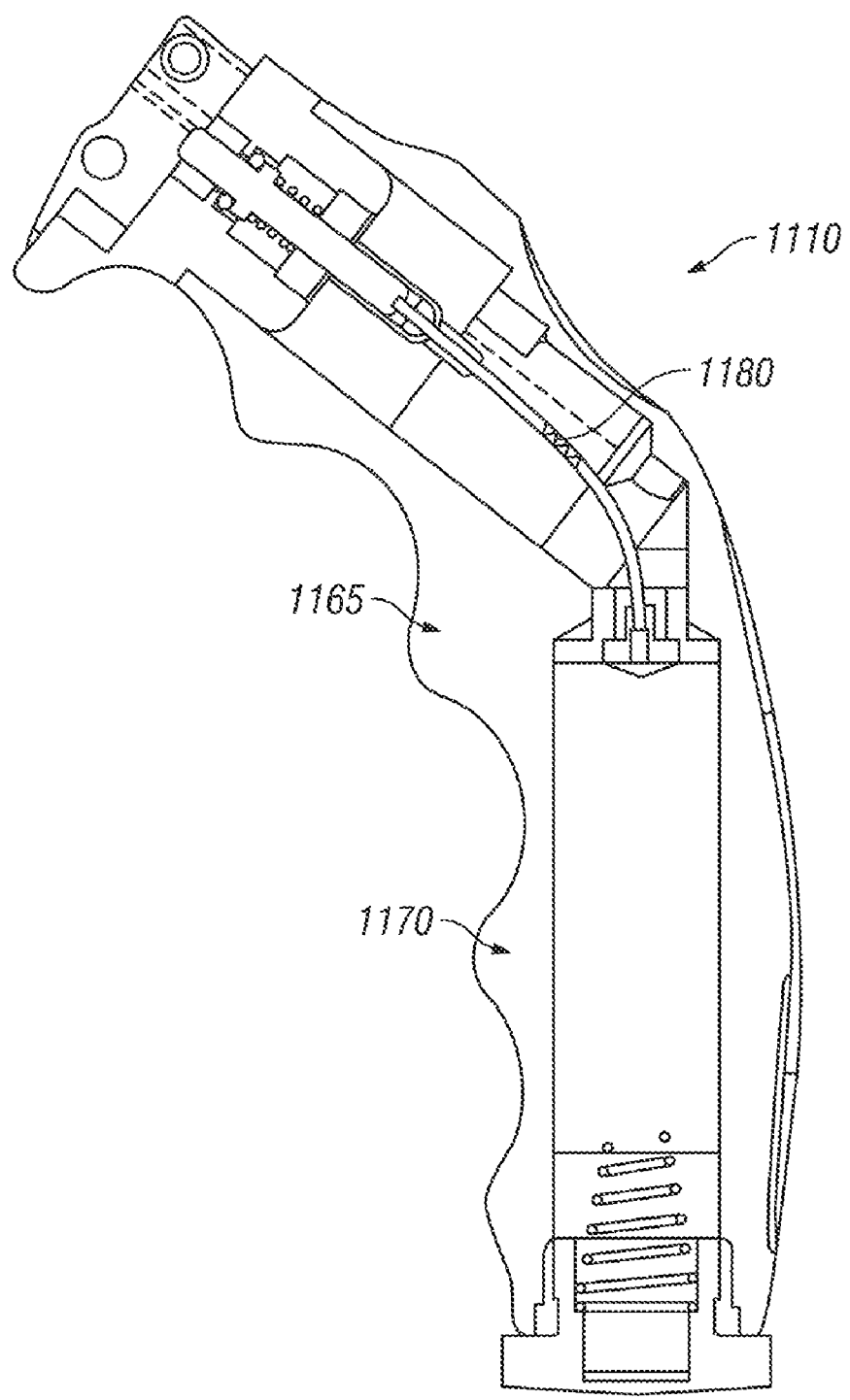
FIG. 25 is a cross-sectional view of the handle of the laryngoscope illustrated in FIG. 24.

With reference to FIGS. 24 and 25, another embodiment of a laryngoscope 1100 similar to that shown in FIGS. 17-23 will be described. The above descriptions of the laryngoscopes, blades, handles and light sources are in incorporated herein. The laryngoscope 1100 includes a handle 1110 and a blade 1120 that carries a proximal white light source 1150 and a distal black light source 1160. The handle 1110 and the blade 1120 include an electrical circuit 1165 that includes a power source 1170, a resistor 1180, a resistor 1190, the proximal white light source 1150, and the distal black light source 1160.

In the embodiment shown, the white light source 1150 is a cool white LED, with a mcd rating of 100-10,000 millicandela (mcd). In the embodiment shown, the resistor 1190 is a 150 ohm resistor behind the white light source to provide 5 ma at 2.9 volts. This brightness of the white light source 1150 of the proximal white light source 1150 is bright enough to provide general illumination (e.g., of the interior of the mouth and back of the patient's throat) while not being so bright as to overtake the effects of the distal black light source 1160.

In the embodiment shown, the distal black light source 1160 emits electromagnetic radiation including a wavelength in the range of 300 to 450 nm. In a more preferred embodiment, the distal black light source 1160 emits electromagnetic radiation including a wavelength in the range of 385 to 395 nm. In a most preferred embodiment, the distal black light source 1160 emits electromagnetic radiation including a wavelength at 395 nm. The electromagnetic radiation works with the body to help illuminate "vocal cords" or "vocal folds".

The combination of the black light source 1160 and white light source 1150 as shown and described herein increases visualization of airway anatomy during laryngoscopy procedures. An advantage of locating the black light source 1160 distally of the white light source 1150 is that, in use, the proximal white light source 1150 provides general illumination (e.g., of the interior of the mouth and back of the patient's throat) while the distal black light source 1160, which is disposed closer to the patient's vocal cords and the glottis, provides directed black light illumination of the patient's vocal cords and the glottis, prompting the visible effects of fluorescence and phosphorescence with respect to the patient's vocal cords and the glottis.

White incandescent light used in laryngoscopy in the past caused glare, excessive reflectivity, and less differentiation of tissues during procedures. The black light emitted from the black light source 1160, and especially locating it distally of the white light source 1150 as shown/described, causes vocal cords to naturally phosphoresce, clearly identifying pathway to the trachea. The black light and white light combination lighting produces "near-3D optimization of viewing area, causing airway structures to stand out via precision-shadowing effect. The black light and white light wavelength mix dramatically improves discrimination of tissues, field of view, reduces glare and creates better depth perception in the airway.

In the embodiment shown, the resistor 1180 disposed in the handle 1110 is a 13 ohm resistor and the power source 1170 is a 4.5 volt power source (e.g., alkaline battery) to provide the distal black light source 1160 at 49-50 ma at 3.6 volts.

Figure 26:
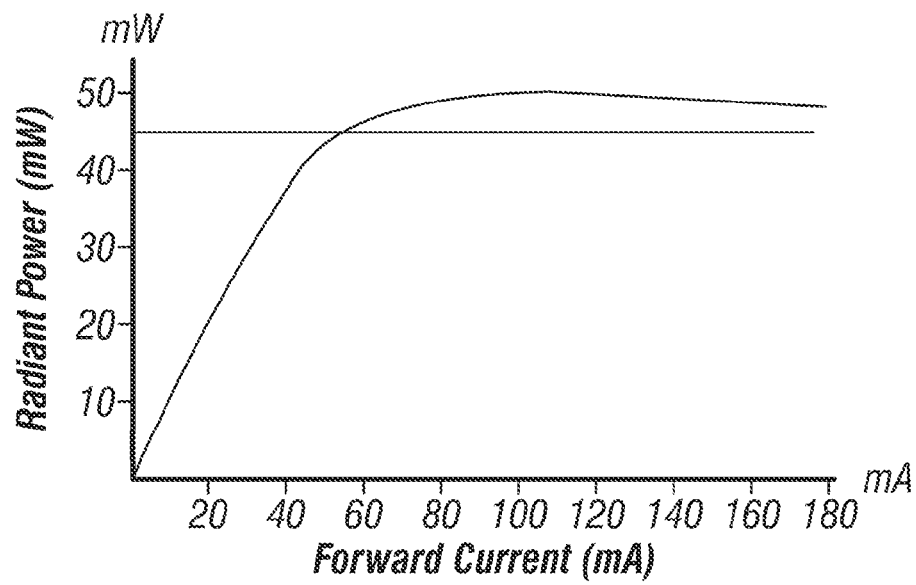
FIG. 26 is an exemplary graph of Radiant Power versus Forward Current for the black light source of the laryngoscope shown in FIG. 24.
Figure 27:
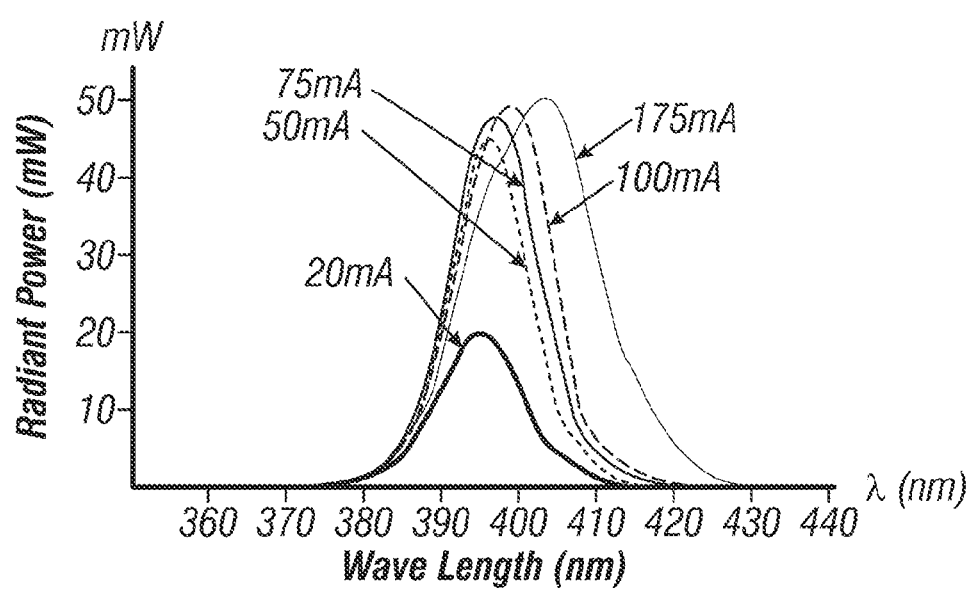
FIG. 27 is an exemplary graph of Radiant Power versus Wave Length for the black light source of the laryngoscope shown in FIG. 24.
Figure 28:
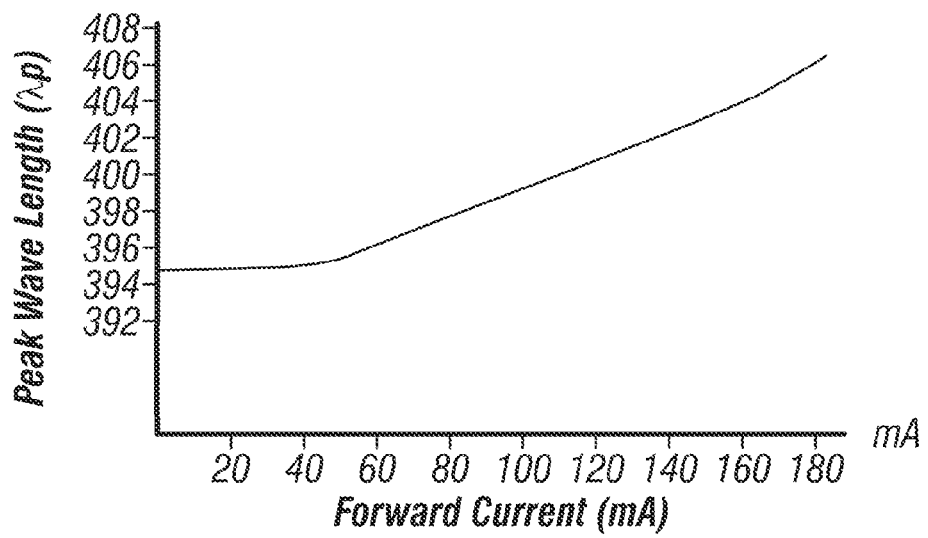
FIG. 28 is an exemplary graph of Peak Wave Length versus Forward Current for the black light source of the laryngoscope shown in FIG. 24.
Figure 29:
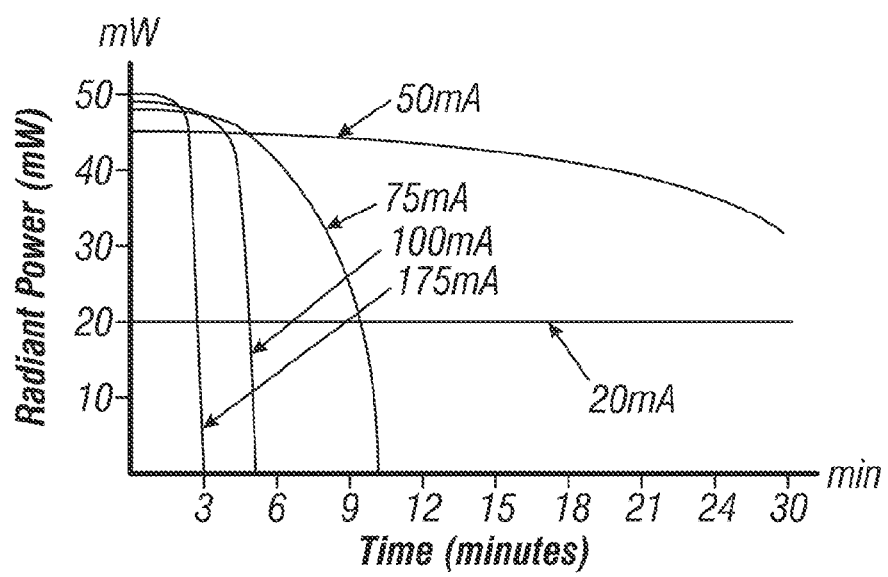
FIG. 29 is an exemplary graph of Radiant Power versus Time for the black light source of the laryngoscope shown in FIG. 24.

FIG. 26 is an exemplary graph of Radiant Power versus Forward Current, FIG. 27 is an exemplary graph of Radiant Power versus Wave Length, FIG. 28 is an exemplary graph of Peak Wave Length versus Forward Current, and FIG. 29 is an exemplary graph of Radiant Power versus Time for the distal black light source 1160 of the laryngoscope 1000 shown in FIG. 24. The above voltage, current, resistor, radiant power, and wave length values for the distal black light source 1160 are obtained from the graphs shown in FIGS. 26-29.

In alternative embodiments, values for voltage, current, resistor, radiant power, wave length, and/or other values than those described and/or shown herein may be used.

Figure 30:
FIG. 30 is an embodiment of an introducer (e.g., endotracheal tube introducer) that may be used with a black light source such as the black light source of the laryngoscopes described and shown herein.

FIG. 30 illustrates an embodiment of an introducer 1200 (e.g., endotracheal tube polyethylene introducer) that may be used with a black light source such as, but not limited to, the black light source 160, 1160 of the laryngoscopes described and shown herein. The introducer 1200 includes a distal portion 1210, an intermediate portion 1220, and a proximal portion 1230. Opposite ends of the introducer 1200 are smooth and, in the embodiment shown, the introducer 1200 has a length of 50-70 cm. One or more of the distal portion 1210, the intermediate portion 1220, and/or the proximal portion 1230 include a fluorescent/phosphorescent color/coating or other color/substance that is enhanced by the black light or that reacts to the black light emitted by the black light source 160, 1160. Thus, the entire introducer 1200 or portion(s) of the introducer 1200 includes a fluorescent/phosphorescent color/coating or other color/substance that is enhanced by or reacts to the black light source 160, 1160 for increased visualization of placement of the introducer 1200 (e.g., endotracheal tube introducer) during the medical procedure (e.g., intubation). The introducer 1200 can be used for, but not by way of limitation, successful orotracheal intubation and endotracheal intubation. The fluorescent/phosphorescent coating on the introducer 1200 causes the introducer 1200 to naturally phosphoresce under black light, clearly identifying introducer tracking through the vocal cords into the trachea.

In alternative embodiments, other types of insertions other than those described/shown herein include a fluorescent/phosphorescent color/coating or other color/substance that is enhanced by or reacts to the black light source 160, 1160 for increased visualization of placement of the insertion during the medical procedure.

In a further embodiment, a camera, scope, or other imaging/viewing device is used with the black light source 160, 1160 for increased visualization during a medical procedure.

Figure 31:
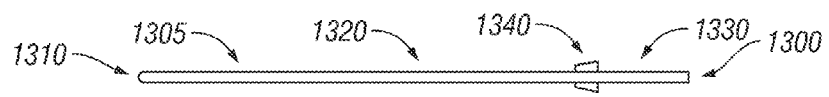
FIG. 31 is an embodiment of a stylet (e.g., endotracheal tube stylet) that may be used with a black light source such as the black light source of the laryngoscopes described and shown herein.
Figure 32A:
FIGS. 32A and 32B are side elevational/end views of a stylet body of the stylet shown in FIG. 31.
Figure 32B:
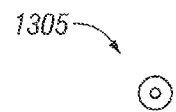

FIG. 31 illustrates an embodiment of a stylet 1300 (e.g., endotracheal tube stylet) that may be used with a black light source such as, but not limited to, the black light source 160, 1160 of the laryngoscopes described and shown herein. The stylet 1300 includes a stylet body 1305 (See also FIGS. 32A, 32B) made of a malleable, coated wire that holds a formed shape to facilitate safe intubation. The stylet body 1305 includes a distal portion 1310, an intermediate portion 1320, and a proximal portion 1330, and a plug connector 1340 slidably attached to the stylet body 1300. In the embodiment shown, the stylet 1300 has a length of 32 cm and a 6-French size.

Figure 33A:
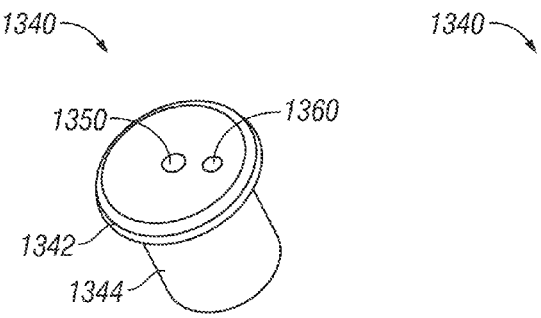
FIGS. 33A, 33B, 33C are top perspective, bottom perspective, and cross-sectional views of the plug connector of the stylet shown in FIG. 31.
Figure 33B:
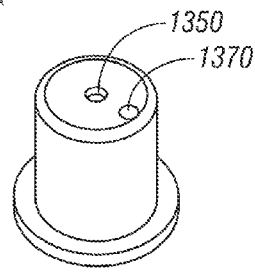
Figure 33C:
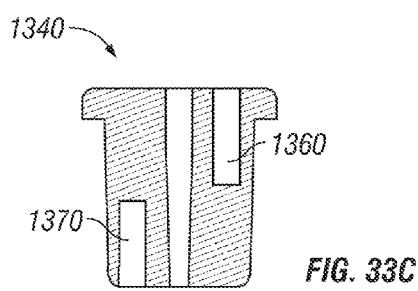
Figure 34:
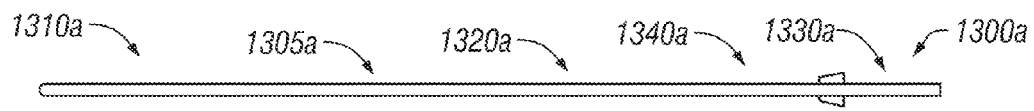
FIG. 34 is a further embodiment of a stylet (e.g., endotracheal tube stylet) that may be used with a black light source such as the black light source of the laryngoscopes described and shown herein.
Figure 35A:
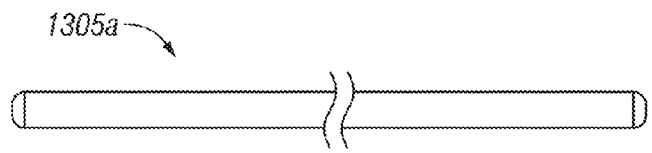
FIGS. 35A and 35B are side elevational/end views of a stylet body of the stylet shown in FIG. 34.
Figure 35B:
Figure 36A:
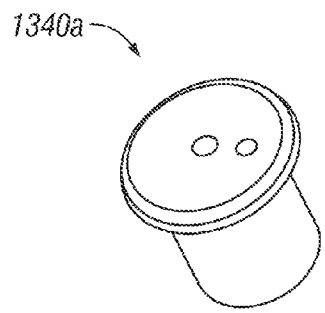
FIGS. 36A, 36B, 36C are top perspective, bottom perspective, and cross-sectional views of the plug connector of the stylet shown in FIG. 31.
Figure 36B:
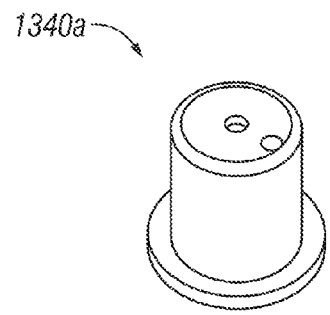
Figure 36C:
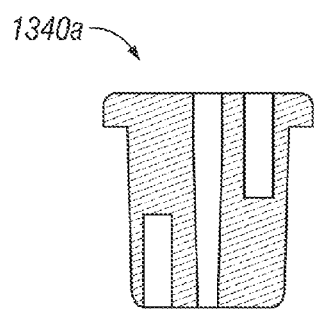

An embodiment of the plug connector 1340 is shown in more detail in FIGS. 33A, 33B, 33C. The plug connector 1340 includes an upper circular flange portion 1342 having an outer diameter and a lower cylindrical plug portion 1344 having an outer diameter that is less than the outer diameter of the upper circular flange portion 1342. The central cylindrical hole/bore 1350 extends through the plug connector 1340 and slidably receives the stylet body 1305. An upper hole/bore 1360 extends into an upper part of the plug connector 1240 and a lower hole/bore 1370 extends into the lower part of the plug connector 1240.

One or more of the distal portion 1310, the intermediate portion 1320, and/or the proximal portion 1330 include a fluorescent/phosphorescent color/coating or other color/substance that is enhanced by the black light or that reacts to the black light emitted by the black light source 160, 1160. Thus, the entire stylet 1300 or portion(s) of the stylet 1300 includes a fluorescent/phosphorescent color/coating or other color/substance that is enhanced by or reacts to the black light source 160, 1160 for increased visualization of placement of the stylet 1300 (or stylet 1300 and endotracheal intubation tube) during the medical procedure (e.g., intubation). The fluorescent/phosphorescent coating on the stylet 1300 causes the stylet 1300 to naturally phosphoresce under black light, clearly identifying stylet/intubation tube tracking through the vocal cords into the trachea.

FIGS. 34-36C disclose another embodiment of a stylet 1300*a* that is similar to the stylet 1300 described above except that it is a larger size (45 cm length, 8 French). Elements of the stylet 1300*a* that are similar to the elements of the stylet 1300 are identified with the same reference number, but with an "a" suffix.

FIGS. 37A and 37B illustrate an embodiment of a movable, protective cuff sheath 1400 that covers a distal endotracheal tube cuff 1410 (FIG. 37A) including an expandable body (e.g., balloon) 1430 during insertion of an endotracheal tube 1420 (e.g., during intubation) and moves to a retracted position (FIG. 37B) once the endotracheal tube 1420 is in position to expand the expandable body 1430. The movable protective cuff sheath 1400 reduces the profile and visibility of the distal endotracheal tube cuff 1410 during intubation. The movable, protective sheath covering the expandable body 1430 (e.g., pre-inflated balloon) reduces the profile of the expandable body 1430/cuff 1410 and aids physical visibility down the airway during intubation. The movable, protective cuff sheath 1400 and/or distal endotracheal tube cuff 1410 includes a fluorescent/phosphorescent color/coating or other color/substance that is enhanced by or reacts to the black light source 160, 1160 to aid in visibility and positioning of the cuff 1410.

FIGS. 38A and 38B illustrate an embodiment of a low-profile, low-visibility distal endotracheal tube cuff 1510 to reduce profile and visibility during intubation. In one or more embodiments, the low-profile, low-visibility distal endotracheal tube cuff 1510 includes one or more of a low-profile expandable body material 1530 (e.g., lower-profile, more-compliant balloon material utilized that will lay flat against body 1540 of tube 1550 in non-inflated state), a low-profile expandable body (e.g., balloon) packing configuration, and/or an indented tube body 1540 in the balloon cuff region (e.g., addition of indentation of tube body or smaller diameter indented section 1550 versus larger diameter outer tube section 1560 to enable further profile reduction of the pre-inflated balloon) to reduce the cuff profile and aid physical visibility down the airway during intubation procedures. The expandable body material 1530 includes a diameter/dimension D2 that is less than the diameter/dimension D1 of the outer tube section 1560 in the collapsed condition shown in FIG. 38A, and includes a diameter/dimension D3 that is greater than the diameter/dimension D1 of the outer tube section 1560 in the expanded condition shown in FIG. 38B (the expandable body material 1530 is expanded to secure the cuff 1510 in position in passageway). The expandable body material 1530 includes a fluorescent/phosphorescent color/coating or other color/substance that is enhanced by or reacts to the black light source 160, 1160 to aid in visibility and positioning of the cuff 1510.

Compared to current ET tube designs, which include distal cuffs that, even in their non-inflated states, have a wide profile which impedes visibility of the vocal cords and surrounding anatomy during intubation, the low-profile, low-visibility distal endotracheal tube cuff 1510 reduces the cuff profile and aids physical visibility down the airway during intubation. The fluorescent/phosphorescent color/coating on the expandable body material 1530 is enhanced by or reacts to the black light source 160, 1160 to aid in visibility and positioning of the cuff 1510.

Figure 50A:
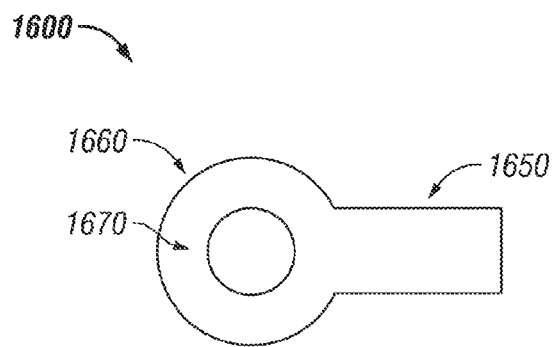
FIGS. 50A, 50B, and 50C are side-elevational views of an embodiment of a removable sheath for a cuff of an endotracheal tube.
Figure 50B:
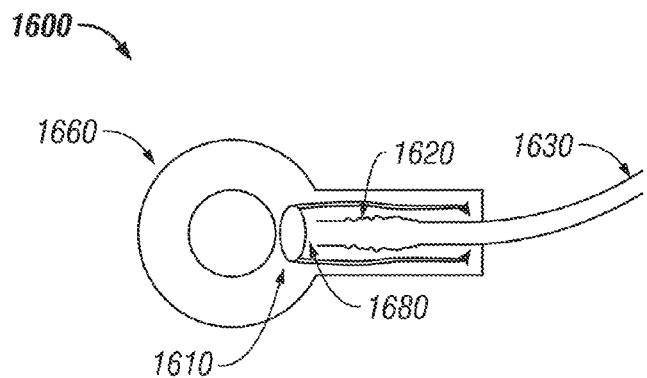
Figure 50C:
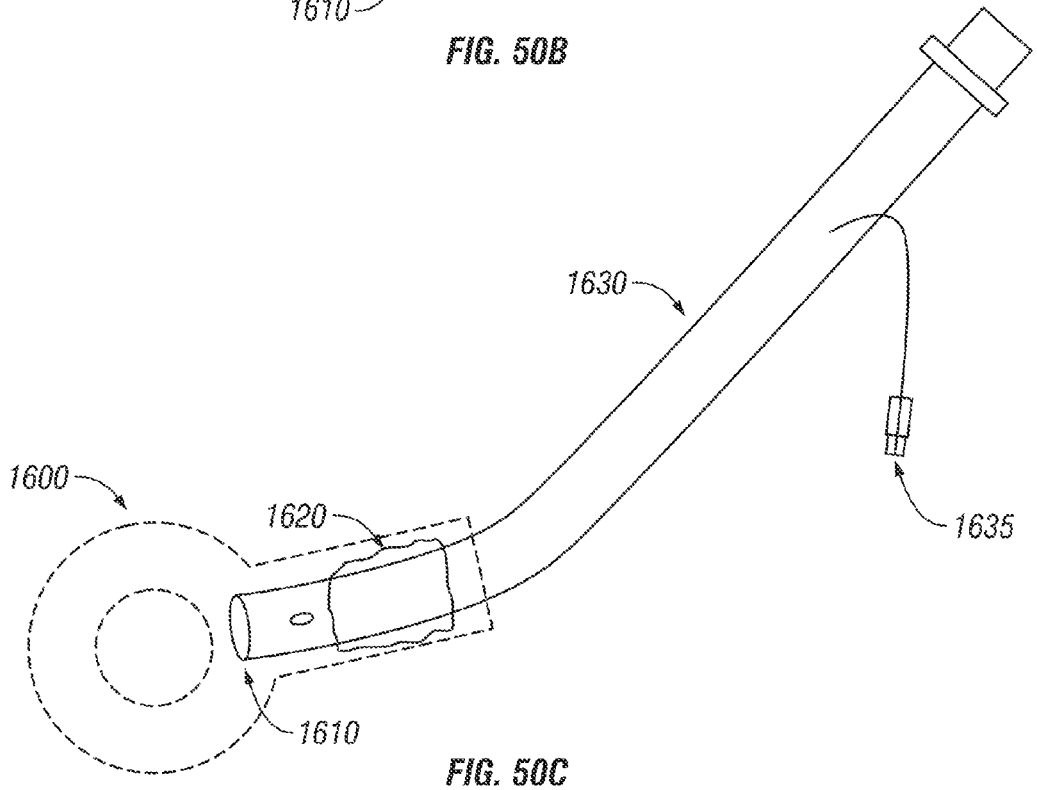

With reference to FIGS. 50A-C, an embodiment of a removable sheath 1600 for an endotracheal tube cuff 1610, which includes an expandable body (e.g., balloon) 1620, will be described. The endotracheal tube cuff 1610 and expandable body 1620 are disposed at a distal portion of an endotracheal tube 1630. The endotracheal tube 1630 includes an inflation mechanism 1635 for inflating (e.g., 10-12 cc of air) the expandable body 1620. The removable sheath 1600 includes a substantially tubular portion 1650 and a finger portion 1660 with a finger hole 1670 to receive a finger of a user for removing the substantially tubular portion 1650 of the sheath 1600 from the endotracheal tube cuff 1610. The purpose of the removable sheath 1600 is to protect the expandable body 1620 of the cuff 1610 before use, to eliminate the need for pre-use inflation/testing/checking of the expandable body 1620, and, in one embodiment (e.g., FIG. 50B), as a possible site for a reservoir 1680 (e.g., lidocaine jelly reservoir, which may be popped opened/closed) for peruse applications of gels or medicine (e.g., lidocaine jelly or similar substance for lubrication of tube/cuff/expandable body) to the tube/cuff/expandable body.

FIGS. 39A-39G disclose another embodiment of laryngoscope handle that is especially advantageous when used in endotracheal intubation of children.

FIGS. 40A-49F disclose further embodiment of laryngoscope blades including proximal white light source and a distal black light source. The above descriptions of the laryngoscopes, blades, handles and light sources are in incorporated herein.

FIGS. 40A-40F disclose an embodiment of a Size 00 Miller laryngoscope blade.

FIGS. 41A-41F disclose an embodiment of a Size 0 Miller laryngoscope blade.

FIGS. 42A-42G disclose an embodiment of a Size 1 Miller laryngoscope blade.

FIGS. 43A-43F disclose an embodiment of a Size 2 Miller laryngoscope blade.

FIGS. 44A-44G disclose an embodiment of a Size 3 Miller laryngoscope blade.

FIGS. 45A-45G disclose an embodiment of a Size 4 Miller laryngoscope blade.

FIGS. 46A-46F disclose an embodiment of a Size 1 Macintosh laryngoscope blade.

FIGS. 47A-47F disclose an embodiment of a Size 2 Macintosh laryngoscope blade.

FIGS. 48A-48F disclose an embodiment of a Size 3 Macintosh laryngoscope blade.

FIGS. 49A-49F disclose an embodiment of a Size 4 Macintosh laryngoscope blade.

The above figures may depict exemplary configurations for the invention, which is done to aid in understanding the features and functionality that can be included in the invention. The invention is not restricted to the illustrated architectures or configurations, but can be implemented using a variety of alternative architectures and configurations. Additionally, although the invention is described above in terms of various exemplary embodiments and implementations, it should be understood that the various features and functionality described in one or more of the individual embodiments with which they are described, but instead can be applied, alone or in some combination, to one or more of the other embodiments of the invention, whether or not such embodiments are described and whether or not such features are presented as being a part of a described embodiment. Thus the breadth and scope of the present invention, especially in the following claims, should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; and adjectives such as "conventional," "traditional," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

We claim:

1. A laryngoscope blade for use in viewing the vocal cords of a patient in performance of an endotracheal intubation, comprising:
   a laryngoscope blade portion connectable to a laryngoscope handle to lift the patient's tongue and mandible for viewing the vocal cords and aid in insertion of an endotracheal tube, the laryngoscope blade portion includes a proximal portion and a distal portion;
   a white light source carried by the laryngoscope blade portion;
   a black light source carried by the laryngoscope blade portion to prompt visible effects of fluorescence and phosphorescence with respect to the patient's vocal cords for viewing the vocal cords and passing of the endotracheal tube there between during endotracheal intubation, the black light source located closer to the distal portion and the white light source located closer to the proximal portion, and the black light source emitting electromagnetic radiation having a wavelength in the range of 300 to 450 nm.

2. The laryngoscope blade of claim 1, wherein the black light source emits electromagnetic radiation having a wavelength in the range of 385 to 395 nm.

3. The laryngoscope blade of claim 1, wherein the white light source is a cool white LED with a mcd rating of 100-10,000 millicandela (mcd).

4. The laryngoscope blade of claim 1, further including an electrical circuit including the white light source and a 150 ohm resistor associated with the white light source to provide 5 ma at 2.9 volts.

5. The laryngoscope blade of claim 1, further including an electrical circuit including the black light source and a 13 ohm resistor so that the distal black light source is at 49-50 ma at 3.6 volts.

6. The laryngoscope blade of claim 1, further including an electrical circuit including a 4.5 volt power source.

7. An endotracheal intubation system for performing an endotracheal intubation, comprising:
    a laryngoscope including the laryngoscope blade of claim 1; and
    an endotracheal tube insertable into the patient's mouth, between the patient's vocal cords into the patient's larynx, and into the patient's trachea for opening the patient's airway, the endotracheal tube includes a distal portion and an expandable body near the distal portion, the distal portion includes a dimension, and the expandable body includes a dimension less than the dimension of the distal portion of the expandable body during intubation and a dimension greater than the dimension of the distal portion of the expandable body to secure the endotracheal tube in place in the trachea.

8. The endotracheal intubation system of claim 7, wherein the distal portion includes a recessed section that carries the expandable body, and the expandable body is recessed in the recessed section so that the expandable body includes a dimension less than the dimension of the distal portion of the expandable body during intubation and so that the expandable body expands to a dimension outside of the recessed section, greater than the dimension of the distal portion, to secure the endotracheal tube in place in the trachea.

9. The endotracheal intubation system of claim 7, wherein the distal portion includes a movable sheath that covers the expandable body during intubation and is movable to uncover the expandable body so that the expandable body is expandable to a dimension greater than the dimension of the distal portion, to secure the endotracheal tube in place in the trachea.

10. The endotracheal intubation system of claim 7, wherein the distal portion includes at least one of a fluorescent and phosphorescent material that is at least one of enhanced by and reacts to the black light source.

11. An endotracheal intubation system for performing an endotracheal intubation, comprising:
    a laryngoscope including the laryngoscope blade of claim 1;
    an endotracheal tube insertable into the patient's mouth, between the patient's vocal cords into the patient's larynx, and into the patient's trachea for opening the patient's airway; and
    a stylet for the endotracheal tube, the stylet including at least one of a fluorescent and phosphorescent material that is at least one of enhanced by and reacts to the black light source.

12. An endotracheal intubation system for performing an endotracheal intubation, comprising:
    a laryngoscope including the laryngoscope blade of claim 1;
    an endotracheal tube insertable into the patient's mouth, between the patient's vocal cords into the patient's larynx, and into the patient's trachea for opening the patient's airway; and
    an endotracheal tube introducer including at least one of a fluorescent and phosphorescent material that is at least one of enhanced by and reacts to the black light source.

13. An endotracheal intubation system for performing an endotracheal intubation, comprising:
    a laryngoscope including the laryngoscope blade of claim 1;
    an endotracheal tube insertable into the patient's mouth, between the patient's vocal cords into the patient's larynx, and into the patient's trachea for opening the patient's airway, the endotracheal tube includes a distal portion and an expandable body near the distal portion; and
    a removable sheath to cover the distal portion of the endotracheal tube and protect the expandable body, the removable sheath removable prior to insertion of the endotracheal tube into the patient's mouth.

14. The endotracheal intubation system of claim 13, wherein the removable sheath includes a substantially tubular portion that covers the distal portion of the endotracheal tube and protects the expandable body.

15. The endotracheal intubation system of claim 13, wherein the removable sheath includes a finger portion engageable by a user's finger to facilitate removal of the removable sheath from the distal portion of the endotracheal tube.

16. The endotracheal intubation system of claim 15, wherein the finger portion includes a finger hole engageable by a user's finger to facilitate removal of the removable sheath from the distal portion of the endotracheal tube.

17. The endotracheal intubation system of claim 13, wherein the removable sheath carries a lubricant for lubricating the distal portion and the expandable body of the endotracheal tube.

* * * * *